(12) United States Patent
Barry et al.

(10) Patent No.: US 9,453,036 B2
(45) Date of Patent: Sep. 27, 2016

(54) GROUP 11 MONO-METALLIC PRECURSOR COMPOUNDS AND USE THEREOF IN METAL DEPOSITION

(75) Inventors: Sean Barry, Ottawa (CA); Jason Coyle, Ottawa (CA); Timothy James Clark, Kingston (CA); Jeffrey J.M. Hastie, Kingston (CA)

(73) Assignee: GreenCentre Canada, Kingston, Ontario (CA), part interest ( * ) Notice: Subject to any disclaimer, the term of this patent is extended or adjusted under 35 U.S.C. 154(b) by 424 days.

(21) Appl. No.: 13/468,601

(22) Filed: May 10, 2012

(65) Prior Publication Data

US 2012/0323008 A1 Dec. 20, 2012

Related U.S. Application Data

(63) Continuation of application No. PCT/CA2012/050296, filed on May 4, 2012.

(60) Provisional application No. 61/485,912, filed on May 13, 2011, provisional application No. 61/552,169, filed on Oct. 27, 2011.

(51) Int. Cl.
| | | |
|---|---|---|
| C07F 1/00 | (2006.01) | |
| C07F 1/08 | (2006.01) | |
| C07F 1/10 | (2006.01) | |
| C07F 7/10 | (2006.01) | |
| C23C 16/18 | (2006.01) | |
| C23C 16/455 | (2006.01) | |

(52) U.S. Cl.
CPC .................. *C07F 7/10* (2013.01); *C07F 1/005* (2013.01); *C07F 1/08* (2013.01); *C23C 16/18* (2013.01); *C23C 16/45553* (2013.01)

(58) Field of Classification Search
CPC ............. C07F 1/005; C07F 1/08; C07F 1/10
See application file for complete search history.

(56) References Cited

U.S. PATENT DOCUMENTS

2009/0004385 A1    1/2009 Blackwell et al.

FOREIGN PATENT DOCUMENTS

| | | |
|---|---|---|
| JP | 2006-161162 | 6/2006 |
| JP | 2007-297347 | 11/2007 |
| JP | 2009-532579 | 9/2009 |
| WO | WO-2004/046417 | 11/2003 |
| WO | WO-2006/012294 | 2/2006 |
| WO | WO-2007/142700 | 12/2006 |
| WO | WO-2008/085426 | 12/2007 |

OTHER PUBLICATIONS

Vicente et al. "New Neutral and Anionic Alkynylgold(I) Complexes via New Synthetic Methods. Crystal and Molecular Structures of [(PPh3)2N][Au(C≡CCH2OH)2], [Au(C≡CSiMe3)(CNtBu)], and [Au(C≡Cr)Pr'3] (R' = Cyclohexyl, R = CH2Cl, CH2Br; R' = Ph, R = SiMe3, tBu)" Organometallics, 1997, vol. 16, pp. 5628-5636.*
Vicente et al. "New Carbenegold(I) Complexes Synthesized by the "Acac Method"" Organometallics, 2003, vol. 22, pp. 4327-4333.*
Alder et al. CAS Accession No. 1999:163969.*
Coyle, J.P. et al., "Synthesis and Thermal Chemistry of Copper (I) Guanidinates", Inorganic Chemistry, 47, (2008), 683-689.
Lin, J.C.Y. et al., "Coinage Metal—N-Heterocyclic Carbene Complexes", Chem. Rev., 109, (2009), 3561-3598.
Herrmann, W.A. et al., "Synthesis, structure and Catalytic application of palladium (II) complexes bearing N-heterocyclic carbenes and phosphines", Journal of Organometallic Chemistry, 617-618, (2001), 616-628.
Tsuda, T. et al., "Preparation and Characterization of Copper (I) Amides", Inorganic Chemistry, 20, (1981), 2728-2730.
Gaillard, S. et al., "N-Heterocyclic Carbene Gold(I) and Copper(I) Complexes in C-H Bond Activation", Accounts of Chemical Research, vol. 45, No. 6, (2012), 778-787.
Goj, L.A. et al., Cleavage of X-H Bonds (X= N, O or C) by Copper(I) Alkyl Complexes to Form Monomeric Two-Coordinate Copper(I) Systems, Inorganic Chemistry, 44, (2005), 8647-8649.
Goj, L.A. et al., "Chemistry Surrounding Monomeric Copper(I) Methyl, Phenyl, Anilido, Ethoxide, and Phenoxide Complexes Supported by N-Heterocyclic Carbene Ligands: Reactivity Consistent with Both Early and Late Transition Metal Systems", Inorganic Chemistry, 45, (2006), 9032-9045.
Mankad, N.P. et al., "Synthesis, Structure, and Akyne Reactivity of a Dimeric (Carbene)copper(I) Hydride", Organometallics, 23, (2004), 3369-3371.
Kuhn, N. et al., "Synthesis of Imidazol-2-ylidenes by Reduction of Imidazole-2(3H)-thiones", Synthesis, (1993), 561-562.
Coyle, J.P. et al., "Heteroleptic Copper (I) Compounds as Volatile Precursors for Metal Deposition", Chemical Society of Canada Conference May 30-Jun. 3, 2009, Hamilton, Ontario, Canada (abstract).
Diez-Gonzalez S et al: "N-heterocyclic carbenes in late transition metal catalysis", 1,3 Chemical Reviews, American Chemical Society, US, vol. 109, No. 8, Aug. 12, 2009.
Extended European Search Report and European Search Opinion for EP 12785682.1 mailed Dec. 12, 2014.
Office Action for JP 2014-510625 dated Mar. 22, 2016. (with English Translation).

* cited by examiner

*Primary Examiner* — Joseph Kosack
(74) *Attorney, Agent, or Firm* — Foley & Lardner LLP

(57) ABSTRACT

The present application provides precursor compounds useful for deposition of a group 11 metal on a substrate, for example, a microelectronic device substrate, as well as methods of synthesizing such precursor compounds. The precursor compounds provided are mono-metallic compounds comprising a diaminocarbene (DAC) having the general formula: "DAC-M-X", where the diaminocarbene is an optionally substituted, saturated N-heterocyclic diaminocarbene (sNHC) or an optionally substituted acyclic diaminocarbene, M is a group 11 metal, such as copper, silver or gold; and X is an anionic ligand. Also provided are methods of synthesizing the precursor compounds, metal deposition methods utilizing such precursor compounds, and to composite materials, such as, e.g., microelectronic device structures, and products formed by use of such precursors and deposition methods.

41 Claims, 37 Drawing Sheets

MW: 350.13 g/mol
m.p.: > -35 °C
% Cu: 18.15

MW: 378.18 g/mol
% Cu: 16.80

MW: 378.18 g/mol
liquid at RT
% Cu: 16.80

MW: 392.21 g/mol
% Cu: 16.20

MW: 511.60 g/mol
mp.: 77-79 °C
% Au: 38.50

GROUP 11 MONO-METALLIC PRECURSOR COMPOUNDS AND USE THEREOF IN METAL DEPOSITION

RELATED APPLICATIONS

This application claims priority to PCT International Application Number PCT/CA2012/050296, filed May 4, 2012, which claims priority to U.S. Provisional Patent Application No. 61/485,912, filed May 13, 2011 and U.S. Provisional Patent Application No. 61,/552,169, filed Oct. 27, 2011. This application claims the benefit of U.S. Provisional Patent Application No. 61/485,912, flied May 13, 2011, and U.S. Provisional Patent Application No. 61/552, 169, filed Oct. 27, 2011. the contents of the foregoing applications are hereby incorporated herein by reference in their entireties.

FIELD OF THE INVENTION

The present invention relates to precursor compounds useful for deposition of a group 11 metal on a substrate, for example, a microelectronic device substrate, as well as to methods of synthesizing such precursor compounds and to corresponding deposition methods of utilizing such precursors, and to composite materials, such as, microelectronic device structures, and products formed by use of such precursors and deposition methods, also including specialty optics, thin-films in batteries and other applications, sensors, catalyst substrates, and other surfaces requiring fine coatings.

BACKGROUND OF THE INVENTION

Microfabrication processes are used in the fabrication of structures of micrometre sizes and smaller. The earliest microfabrication processes were used for integrated circuit manufacture (or semiconductor device fabrication), however, recently these processes have been applied, for example, in microelectromechanical systems (MEMS) and subfields, such as microfluidics/lab-on-a-chip, optical MEMS, etc. The miniaturization of devices presents challenges in fabrication technologies.

While microfabrication is a collection of technologies used in manufacturing micro- and nanodevices, most microfabrication processes include thin film deposition. The purpose and material used in these thin films varies depending on the type of device. Commonly, electronic devices require thin films which are conductors (metal).

Copper is often used in semiconductor device manufacturing. As the use of copper has permeated the marketplace because of its relatively low cost and processing properties, semiconductor manufacturers continue to look for ways to improve copper deposition techniques. Several processing methods have been developed to manufacture copper interconnects as feature sizes have decreased. Each processing method may increase the likelihood of errors such as copper diffusion across boundary regions, copper crystalline structure deformation, and dewetting. Physical vapour deposition (PVD), chemical vapour deposition (CVD), atomic layer deposition (ALD), chemical mechanical polishing (CMP), electrochemical plating (ECP), electrochemical mechanical polishing (ECMP), and other methods of depositing and removing copper layers utilize mechanical, electrical, or chemical methods to manipulate the copper that forms the interconnects.

Physical vapour deposition (PVD) or sputtering has been adopted as a preferred method for depositing conductor films used in semiconductor manufacturing. This has been primarily driven by the low cost, simple sputtering approach of PVD whereby relatively pure elemental or compound materials can be deposited at relatively low substrate temperatures. However, as device length scales have decreased, the step coverage limitations of PVD have increasingly become an issue since it is inherently a line-of-sight process. Step coverage refers to the difference in deposited film thickness in different parts of a micro- or nanostructure. Ideally, there is no difference in deposited film thickness throughout the structure. This is difficult or impossible to achieve using a line-of-sight process such as PVD, which limits the total number of atoms or molecules that can be delivered into a trench or via (resulting in thinner films in trenches or vias than in the rest of the structure). Consequently, PVD is unable to deposit thin continuous films of adequate thickness to coat the sides and bottoms of high aspect ratio trenches and vias.

In addition, miniaturization of devices has led to a desire for thinner seed layers, which require greater flatness and uniformity in order to plate evenly. Copper resistivity increases sharply in films less than 10 nm in thickness, leading to uneven plating. Medium/high-density plasma and ionized PVD sources have been developed in an attempt to provide film uniformity even in the more aggressive device structures. However, these sources are still not adequate and are now of such complexity that cost and reliability have become serious concerns.

CVD processes offer improved step coverage (i.e., improved film uniformity) since CVD processes can be tailored to provide conformal films. Conformality ensures the deposited films match the shape of the underlying substrate, and the film thickness inside the feature, such as a trench or via, is uniform and equivalent to the thickness outside the feature. Unfortunately, CVD requires comparatively high deposition temperatures, suffers from high impurity concentrations, which impact film integrity, and is more expensive than PVD due to long nucleation times and poor precursor gas utilization efficiency.

Atomic layer deposition (ALD) has been proposed as an alternative method to CVD for depositing conformal, ultra-thin films at comparatively lower temperatures. ALD is similar to CVD except that the substrate is sequentially exposed to one reactant at a time, or one dose of a reactant at a time. Conceptually, it is a simple process: a first reactant is introduced to a heated substrate whereby it forms a monolayer on the surface of the substrate. Excess reactant is pumped out (e.g., evacuated). Next a second reactant is introduced and reacts with the existing monolayer to form a monolayer of a desired reaction product through a "self-limiting surface reaction". The process is self-limiting since the deposition reaction halts once the initially adsorbed (physisorbed or chemisorbed) monolayer of the first reactant has fully reacted with the second reactant. Finally, the excess second reactant is evacuated. This sequence comprises one deposition cycle. The desired film thickness is obtained by repeating deposition cycles as necessary to reach the desired film thickness. As is apparent, the sequential nature of ALD precursor deposition, reaction and alternate purging one atomic/molecular layer at a time has the disadvantage of being slower than some other deposition techniques. However it is this cycle of building up highly uniform monolayers one at a time that allows ALD to produce films of a surface uniformity, smoothness and thinness that is impossible to achieve with other techniques. This makes ALD uniquely valuable in demanding coating applications.

In practice, ALD is complicated by painstaking process optimisation wherein: 1) at least one of the reactants sufficiently adsorbs to a monolayer and 2) surface deposition reaction can occur with adequate growth rate and film purity. If the substrate temperature needed for the deposition reaction is too high, desorption or decomposition of the first adsorbed reactant occurs, thereby preventing the layer-by-layer growth process. High substrate temperatures can also lead to mobility of the coating material which may agglomerate and ruin the film flatness or the coating material can become less uniformly dispersed or become dewetted, especially at boundary regions of a substrate structure. If the temperature is too low, the deposition reaction may be incomplete (i.e., very slow), not occur at all, or lead to poor film quality (e.g., high resistivity in the case of metals and/or high impurity content). Low temperatures may also give rise to insufficient activation of the precursor to form a monolayer, or condensation of a multilayer of precursor molecules. Since ALD processes largely rely on the thermal reactivity of precursors (i.e., reactants), selection of those that fit this temperature window becomes difficult and sometimes unattainable. Due to the strict process optimisation requirements, ALD has been typically limited to the deposition of semiconducting or insulating materials as opposed to metals. Until recently ALD of metals has been confined to the use of metal halide precursors. However, halides (e.g., Cl, F, Br) are corrosive and can create reliability issues in metal interconnects.

As a result of its low resistivity, low contact resistance, and ability to enhance device performance through the reduction of resistor-capacitor time delays, copper metallization has been adopted by many semiconductor device manufacturers for production of microelectronic chips, thin-film recording heads and packaging components.

There remains a need for precursors of copper and other metals that have sufficient volatility and thermal stability to be useful in ALD.

SUMMARY OF THE INVENTION

It is an object of the present invention to provide group 11 mono-metallic precursor compounds and methods and systems of use thereof in metal deposition and methods of synthesis thereof.

In accordance with one aspect, there is provided a compound of Formula I:

DAC-M-X      I wherein
  DAC is a diaminocarbene that is an optionally substituted, saturated N-heterocyclic diaminocarbene (sNHC) or an optionally substituted acyclic diaminocarbene;
  M is a metal, for example a group 11 metal, bound to the DAC component at the carbenic atom; and
  X is an anionic ligand,
  and wherein DAC and X do not comprise an aryl or heteroaryl group, and M is bound to a non-halogenic atom of X.

In accordance with one embodiment, there is provided a compound of Formula Ia:

       Ia wherein
  sNHC is a saturated N-heterocyclic diaminocarbene that is optionally substituted; and M and X are as defined above,
  and wherein the compound does not comprise an aryl or heteroaryl group, and M is bound to a non-halogenic atom of X.

In an alternative embodiment, the DAC is an acyclic diaminocarbene; and M and X are as defined above.

In accordance with another aspect, there is provided a compound of Formula IIa:

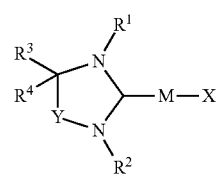

IIa wherein
  X is an anionic ligand;
  M is a metal, for example a group 11 metal, such as, copper, silver or gold;
  Y is $CR^5R^6$, $(CR^5R^6)_2$, or $NR^9$;
  $R^1$ and $R^2$ are each independently H, or an optionally substituted, branched, straight or cyclic aliphatic group, wherein $R^1$ and $R^2$ do not comprise a halo substituent;
  $R^3$, $R^4$, $R^5$ and $R^6$ are each independently H, or an optionally substituted, branched, straight or cyclic aliphatic group; and
  $R^9$ is absent or H, or an optionally substituted, branched, straight or cyclic aliphatic group, wherein, when $R^9$ is absent, the bond between N and the adjacent C is a double bond and $R^3$ or $R^4$ is absent, and wherein the compound does not comprise an aryl or heteroaryl group,
  and M is bound to a non-halogenic atom of X.

In accordance with certain embodiments, an aliphatic group is a $C_1$ to $C_{12}$ alkyl or heteroalkyl or a $C_3$ to $C_{12}$ cycloalkyl or cyclic heteroalkyl.

In accordance with another aspect, there is provided a compound of Formula IIb:

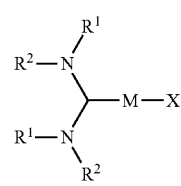

IIb wherein
  X is an anionic ligand;
  M is a metal, for example, a group 11 metal, such as, copper, silver or gold; and
  each $R^1$ and $R^2$ is independently H, or an optionally substituted, branched, straight or cyclic aliphatic group, wherein $R^1$ and $R^2$ do not comprise a halo substituent,
  and wherein the compound does not comprise an aryl or heteroaryl group and M is bound to a non-halogenic atom of X.

It should be understood that in the compound of Formula IIb, the two $R^1$ substituents can be different from one another and from each of the two $R^2$ substituents. Similarly, it should be understood that the two $R^2$ substituents can be different from one another and from each of the two $R^1$ substituents. Specifically, the structure of Formula IIb encompasses compounds having four different substituents at the two nitrogens.

A process for depositing a metal film on a substrate, comprising chemical vapour deposition (CVD), atomic layer deposition (ALD), plasma enhanced chemical vapour deposition (PE-CVD) or plasma enhanced atomic layer deposition (PE-ALD) using a compound of Formula I:

DAC-M-X       I wherein
    DAC is a diaminocarbene that is an optionally substituted, saturated N-heterocyclic diaminocarbene (sNHC) or an optionally substituted acyclic diaminocarbene;
    M is a group 11 metal, such as copper, silver or gold, bound to the DAC component at the carbenic atom; and
    X is an anionic ligand,
and wherein DAC and X do not comprise an aryl or heteroaryl group, and M is bound to a non-halogenic atom of X.

In accordance with another aspect, there is provided a process for forming a thin film comprising a metal, said process comprising the steps: exposing a substrate to vapour comprising a precursor compound of Formula I:

DAC-M-X       I wherein
    DAC is a diaminocarbene that is an optionally substituted, saturated N-heterocyclic diaminocarbene (sNHC) or an optionally substituted acyclic diaminocarbene;
    M is a group 11 metal bound to the sNHC component at the carbenic atom; and
    X is an anionic ligand,
    and wherein the compound does not comprise an aryl or heteroaryl group, and M is bound to a non-halogenic atom of X,
under conditions that permit adsorption of the precursor compound to form a monolayer on the substrate; purging excess precursor compound; exposing the adsorbed precursor monolayer formed in the first step to a second precursor compound to reduce the precursor monolayer to form a metal layer; and repeating the steps until the thin film reaches a desired thickness.

In accordance with another aspect, there is provided a process for forming a thin film comprising a metal, comprising: exposing a substrate to vapour comprising a precursor compound and a reactive gas to form a metal film on the surface of the substrate, wherein the precursor compound is a compound of Formula I:

DAC-M-X       I wherein
    DAC is a diaminocarbene that is an optionally substituted, saturated N-heterocyclic diaminocarbene (sNHC) or an optionally substituted acyclic diaminocarbene;
    M is a group 11 metal bound to the sNHC component at the carbenic atom; and
    X is an anionic ligand,
and wherein the compound does not comprise an aryl or heteroaryl group, and M is bound to a non-halogenic atom of X. Optionally, the precursor and the reactive gas are introduced in a stepwise process. In one embodiment of the present invention, the reactive gas is plasma.

In accordance with another aspect, there is provided a process for forming a group 11 metal-containing film on a substrate comprising: volatilizing a group 11 mono-metallic precursor compound to form a precursor vapour; and contacting the substrate with the precursor vapour to form the group 11 metal-containing film on said substrate,
wherein the precursor is a compound of Formula I:

DAC-M-X       I wherein
    DAC is a diaminocarbene that is an optionally substituted, saturated N-heterocyclic diaminocarbene (sNHC) or an optionally substituted acyclic diaminocarbene;
    M is a group 11 metal bound to the sNHC component at the carbenic atom; and
    X is an anionic ligand,
and wherein the compound does not comprise an aryl or heteroaryl group, and M is bound to a non-halogenic atom of X.

In accordance with another aspect, there is provided a system for use in metal deposition to form a thin film on a substrate, comprising a compound of Formula I:

DAC-M-X       I wherein
    DAC is a diaminocarbene that is an optionally substituted, saturated N-heterocyclic diaminocarbene (sNHC) or an optionally substituted acyclic diaminocarbene;
    M is a group 11 metal bound to the sNHC component at the carbenic atom; and
    X is an anionic ligand,
and wherein the compound does not comprise an aryl or heteroaryl group, and M is bound to a non-halogenic atom of X.

In accordance with another aspect, there is provided an ALD precursor formulation comprising a group 11 mono-metallic precursor compound of Formula I:

DAC-M-X       I wherein
    DAC is a diaminocarbene that is an optionally substituted, saturated N-heterocyclic diaminocarbene (sNHC) or an optionally substituted acyclic diaminocarbene;
    M is a group 11 metal bound to the sNHC component at the carbenic atom; and
    X is an anionic ligand,
and wherein the compound does not comprise an aryl or heteroaryl group, and M is bound to a non-halogenic atom of X.

In accordance with another aspect, there is provided a method of synthesizing a metal precursor compound of Formula Ia sNHC-M-X       Ia wherein
    sNHC is a saturated N-heterocyclic diaminocarbene that is optionally substituted;

M is a metal, for example, a group 11 metal, bound to the sNHC component at the carbenic atom; and X is an anionic ligand, said method comprising:

reacting an sNHC metal halide with a salt of the anionic ligand such that a bond is formed between M and a non-halogenic atom of X.

In accordance with one embodiment, the method of synthesis comprises reacting a metal halide of Formula IV or Formula IVa:

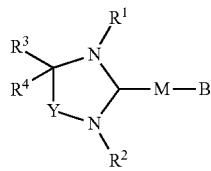

IV

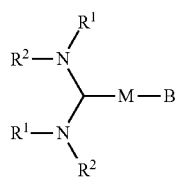

IVa wherein B is a halide;

M is a metal, for example a group 11 metal, such as, copper, silver or gold;

Y is $CR^5R^6$, $(CR^5R^6)_2$, or $NR^5$;

$R^1$ and $R^2$ are each independently H, or an optionally substituted branched, straight or cyclic aliphatic group, wherein $R^1$ and $R^2$ do not comprise any halide atoms; and $R^3$, $R^4$, $R^5$ and $R^6$ are each independently H, or an optionally substituted, branched, straight or cyclic aliphatic group;

with a salt of the anionic ligand X to produce a compound of Formula IIa or Formula IIb, respectively:

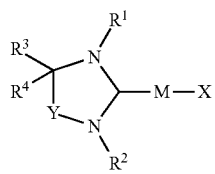

IIa

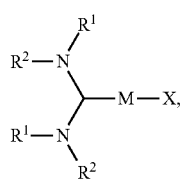

IIb wherein the precursor compound does not comprise an aryl or heteroaryl group, and M is bound to a non-halogenic atom of X.

It should be understood that the two $R^1$ substituents can be different from one another and from each of the two $R^2$ substituents. Similarly, it should be understood that the two $R^2$ substituents can be different from one another and from each of the two $R^1$ substituents. Specifically, the structure of Formula IVa encompasses compounds having four different substituents at the two nitrogens.

BRIEF DESCRIPTION OF THE DRAWINGS

For a better understanding of the present invention, as well as other aspects and further features thereof, reference is made to the following description which is to be used in conjunction with the accompanying drawings, where.

DETAILED DESCRIPTION

Figure 1:
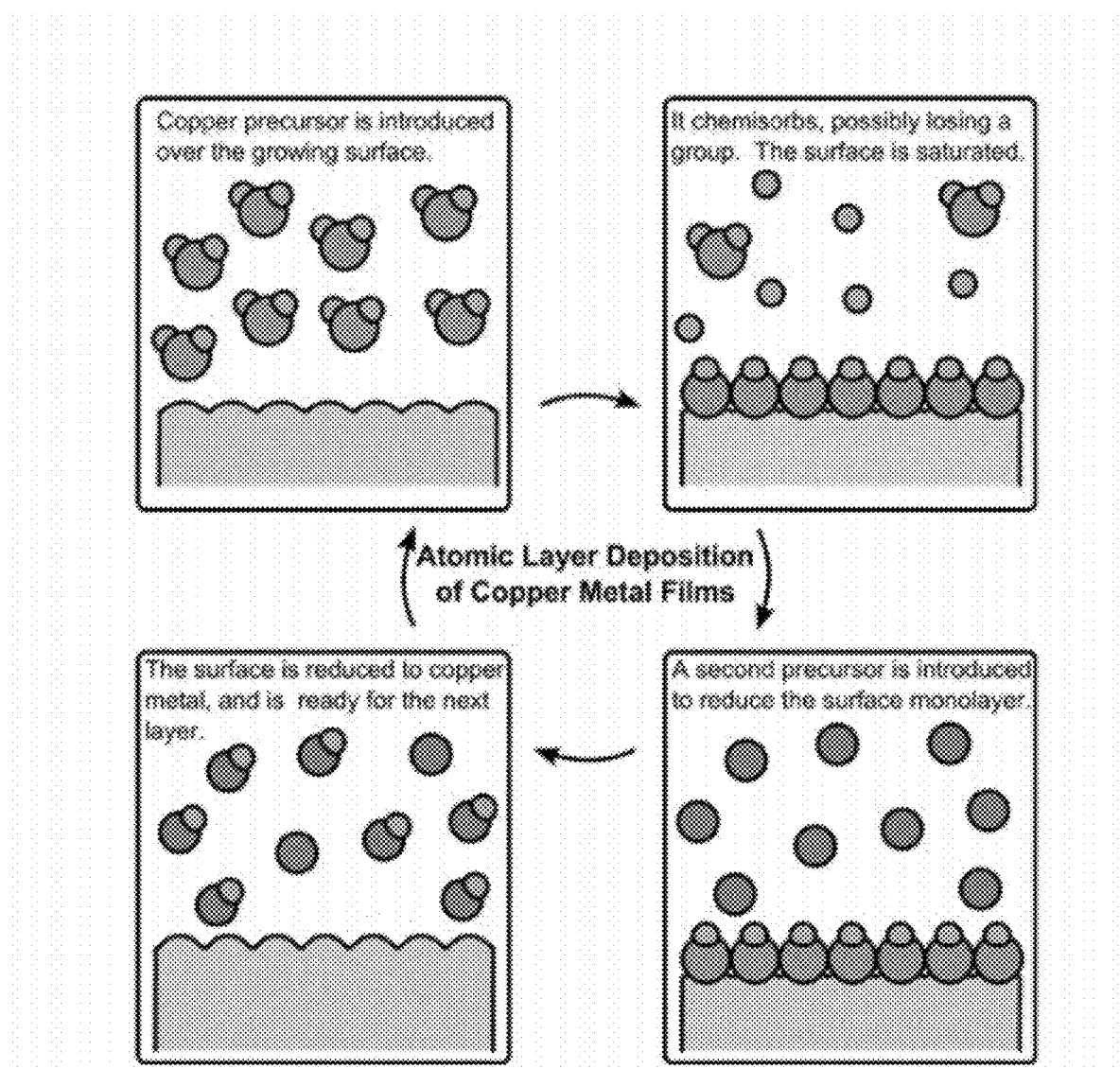
FIG. 1 is a pictorial overview of an atomic layer deposition process.

Unless defined otherwise, all technical and scientific terms used herein have the same meaning as commonly understood by one of ordinary skill in the art to which this invention belongs.

Unless the context clearly indicates otherwise, as used herein plural forms of the terms herein are to be construed as including the singular form and vice versa.

The terms "comprises" and "comprising" as used herein will be understood to mean that the list following is non-exhaustive and may or may not include any other additional suitable items, for example one or more further feature(s), component(s) and/or ingredient(s) as appropriate.

As used herein, "aliphatic" refers to hydrocarbon moieties that are linear, branched or cyclic, may be alkyl, alkenyl or alkynyl, may be substituted or unsubstituted and may include one or more heteroatoms. "Alkenyl" means a hydrocarbon moiety that is linear, branched or cyclic and comprises at least one carbon to carbon double bond. "Alkynyl" means a hydrocarbon moiety that is linear, branched or cyclic and comprises at least one carbon to carbon triple bond. "Aryl" means a moiety including a substituted or unsubstituted aromatic ring, including heteroaryl moieties and moieties with more than one conjugated aromatic ring; optionally it may also include one or more non-aromatic ring. "$C_5$ to $C_g$ Aryl" means a moiety including a substituted or unsubstituted aromatic ring having from 5 to 8 carbon atoms in one or more conjugated aromatic rings. Examples of aryl moieties include phenyl.

As used herein, the term "aliphatic" includes "short chain aliphatic" or "lower aliphatic," which refers to $C_1$ to $C_4$ aliphatic, and "long chain aliphatic" or "higher aliphatic," which refers to $C_5$ to $C_{12}$ aliphatic.

"Heteroaryl" means a moiety including a substituted or unsubstituted aromatic ring having from 4 to 8 carbon atoms and at least one heteroatom in one or more conjugated aromatic rings. As used herein, "heteroatom" refers to non-carbon and non-hydrogen atoms, such as, for example, O, S, and N. Examples of heteroaryl moieties include pyridyl, furanyl and thienyl.

"Alkylene" means a divalent alkyl radical, e.g., —$C_fH_{2f}$— wherein f is an integer. "Alkenylene" means a divalent alkenyl radical, e.g., —CHCH—.

"Substituted" means having one or more substituent moieties whose presence does not interfere with the desired function or reactivity. Examples of substituents include alkyl, alkenyl, alkynyl, cycloalkyl (non-aromatic ring), Si(alkyl)$_3$, Si(alkoxy)$_3$, alkoxyl, amino, alkylamino, alkenylamino, amide, amidine, guanidine, hydroxyl, thioether, alkylcarbonyl, alkylcarbonyloxy, alkoxycarbonyloxy, carbonate, alkoxycarbonyl, aminocarbonyl, alkylthiocarbonyl, phosphate, phosphate ester, phosphonato, phosphinato, cyano, halo, acylamino, imino, sulfhydryl, alkylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, and cycloalkyl (non-aromatic ring).

As used herein, the term "unsubstituted" refers to any open valence of an atom being occupied by hydrogen. Also, if an occupant of an open valence position on an atom is not specified then it is hydrogen.

As used herein, the terms "deposition process" and "vapour deposition process" refer to a process in which a metal layer is formed on one or more surfaces of a substrate from vaporized precursor composition(s) including one or more metal-containing compounds. The metal-containing compounds are vaporized and directed to and/or contacted with one or more surfaces of a substrate (e.g., semiconductor substrate or substrate assembly) placed in a deposition chamber. Typically, the substrate is heated. These metal-containing compounds form a non-volatile, thin, uniform, metal-containing layer on the surface(s) of the substrate. As used herein, a "vapour deposition process" can be a chemical vapour deposition processes (including pulsed chemical vapour deposition processes) or an atomic layer deposition process.

As used herein, the term "chemical vapour deposition" or "CVD" refers to a vapour deposition process wherein the desired layer is deposited on the substrate from vaporized metal-containing compounds (and any reaction gases used) within a deposition chamber with no effort made to separate the reaction components.

As used herein, the term "atomic layer deposition" or "ALD" as used herein refers to a vapour deposition process in which deposition cycles, preferably a plurality of consecutive deposition cycles, are conducted in a process chamber (i.e., a deposition chamber). Typically, during each cycle the precursor is chemisorbed to a deposition surface (e.g., a substrate assembly surface or a previously deposited underlying surface such as material from a previous ALD cycle), forming a monolayer or sub-monolayer that does not readily react with additional precursor (i.e., a self-limiting reaction). Thereafter, if necessary, a reactant (e.g., another precursor or reaction gas) may be introduced into the process chamber for use in converting the chemisorbed precursor to the desired material on the deposition surface. Typically, this reactant is capable of reaction with the already chemisorbed precursor. Further, purging steps may also be utilized during each cycle to remove excess precursor from the process chamber and/or remove excess reactant and/or reaction by-products from the process chamber after conversion of the chemisorbed precursor.

As compared to the one step CVD process, the longer duration multi-cycle ALD process provides improved control of layer thickness and composition by self-limiting layer growth, and minimizes detrimental gas phase reactions by separation of the reaction components. The self-limiting nature of ALD provides a method of depositing a film on a wide variety of reactive surfaces, including surfaces with irregular topographies, with better step coverage than is available with CVD or with other "line of sight" deposition methods such as evaporation or physical vapour deposition (PVD or sputtering).

As used herein, the term "bubbler" is used to refer to a component of a metal deposition system that is a container in which a solid or liquid precursor is converted to its vapour form using heat and an inert gas bubbled into the container and through the precursor. The bubbler typically includes an inlet tube at the bottom of the container through which the inert gas is introduced into the chamber. The mixture of the inert gas and the precursor vapour exit the bubbler into the deposition chamber.

As used herein, the term "carbene" is a molecule comprising a neutral carbon atom with a valence of two, and two valence electrons available for formation of a dative bond (i.e., with a metal fragment or complex). An "N-heterocyclic carbene" or "NHC" is a type of diaminocarbene in which the carbenic carbon is part of a nitrogen-containing heterocycle, such as an imidazole.

As used herein, the term "dative bond" refers to a coordinate covalent bond in which the shared electrons come from one of the atoms only.

As used herein, the terms "saturated N-heterocyclic carbene", "saturated N-heterocyclic diaminocarbene", "saturated NHC", and "sNHC" refer to diamino heterocyclic carbenes in which the carbenic carbon connects the two nitrogen atoms. The remaining carbon atoms in the heterocycle are saturated (i.e., they are connected via single bonds). Typically, the sNHC is a five membered or a six membered heterocycle.

As used herein, the term "acyclic carbene" or "acyclic diaminocarbene" refers to non-cyclic diamino carbenes in which the carbenic carbon connects the two nitrogen atoms.

As used herein, the term "group 11 metal" refers to the transition metals in group 11 of the periodic table, which are copper (Cu), silver (Ag) and gold (Au). Although roentgenium (Rg) belongs to this group of elements based on its electronic configuration, it is a short-lived transactinide and, therefore, not included within the term "group 11 metals" as used herein.

The term "anionic ligand" as used herein, refers to an anionic ligand bound to a metal centre. As described herein, the anionic ligand in the precursor compounds does not comprise a halogen atom directly bound to the metal centre. Preferably, the anionic ligand is a nitrogen-containing, two coordinate, negatively charged ligand. The anionic ligand can be, for example, amide (—$NR_2$), heterocycle (such as, e.g., piperidine, pyrrolidine), cyclopentadiene, alkoxide, alkyl, hydride, hydroxide, diketonate, diketiminate, amidinate, or guanidinate. Preferably, the anionic ligand does not comprise a halogen atom at any position.

The term "amide" as used herein, refers to the anion $NR_2$ or —$NR_2$, where each R is independently an optionally substituted linear, branched or cyclic aliphatic group, an optionally substituted linear or straight alkylsilyl, or the two R groups together with the amide nitrogen form an optionally substituted heterocycle.

As used herein, and as would be understood by a worker skilled in the art, the term "sccm" is an acronym for Standard Cubic Centimetres per Minute, which is a unit of fluid flow (e.g., gas flow) at standard temperature and pressure.

As used herein, the abbreviation "Cu(tmhd)$_2$" refers to copper bis-(2,2,6,6-tetramethyl-3,5-heptadionate).

Precursor Compounds

Atomic layer deposition (ALD) is intrinsically different from chemical vapour deposition (CVD), which means that precursor compounds include particular characteristics in order to be useful in ALD. In CVD, the precursor compounds react together at the substrate surface to produce the target film, or a precursor compound reacts with itself at the substrate surface to produce the target film (i.e., single source CVD). In contrast, precursor compounds useful in ALD react with the substrate surface to produce a chemically active, adsorbed monolayer. It is then this monolayer that subsequently reacts with a second precursor compound to form the target film (see FIG. 1). Thus, the design and function of a precursor compound for ALD is fundamentally different from the design and function of a precursor compound useful in CVD.

ALD precursor compounds are generally designed around the following five principles:
1. The precursor compound must form a self-limiting monolayer with the substrate: the precursor compound needs to react at the growing surface sufficiently to adsorb and form a single monolayer of a surface species; the precursor compound cannot react entirely to form the target film, or else step-wise growth is not possible.
2. The precursor compound must be sufficiently volatile to vaporise effectively and permit uniform vapour delivery during ALD: factors that can contribute to sufficient volatility include, but are not limited to, molecular weight (low molecular weight can increase volatility), asymmetry, steric bulk (low steric bulk can increase volatility), and intermolecular interactions (low intermolecular interactions can increase volatility).
3. The precursor compound should be liquid at the process temperature since precursors need to volatilise at a steady rate. The surface area of solid material varies as volatilisation occurs, which causes changes in particle size and accumulation of impurities at the surface. Consequently, the kinetics of volatilisation change during volatilisation. However, liquids have a continuously refreshed and unchanging surface area, which allows a steady kinetics of evaporation.
4. The precursor compound must be sufficiently thermally stable to permit controlled, stepwise growth of the film and to resist decomposition while being heated over extended periods of time: if the precursor compounds decompose, for example, in the source container or during the deposition process, this can greatly increase impurity level or cause non-self-limiting growth.
5. The precursor compound must be chemically reactive: the precursor needs to be sufficiently reactive to chemisorb to form a monolayer on a substrate and to react with the subsequent precursor to form a target film.

CVD precursors are generally designed following principles 2-4 above. However CVD precursors are designed to continuously react to form the target film; they do not stop reacting following formation of a monolayer. This difference in chemical reactivity is the most important factor that differentiates an ALD precursor from a CVD precursor.

A precursor compound useful in an ALD process will ideally include some or all of the following characteristics: it will be a solid or liquid at room temperature to facilitate handling; it will be a liquid at process temperature with sufficient volatility to vaporize effectively to permit uniform vapour delivery; it will be thermally stable to permit controlled, stepwise growth of the film and to resist decomposition in inlet devices while being heated over extended periods of time; it will form a monolayer at a range of temperatures to allow processes to be developed over a wide range of reaction conditions; and it will react effectively with its subsequent precursor.

The mono-metallic precursor compounds described herein are highly volatile and highly thermally stable. In order for a precursor compound to be considered "highly volatile", it will achieve a vapour pressure of at least about 1 torr at 160° C. In order for a precursor compound to be considered "highly thermally stable", it remains stable at the required process temperature for extended periods (preferably 1 or more days, 2 or more days, 1 or more weeks, or 2 or more weeks) and will remain stable for those periods of time at temperatures up to at least about 100° C., 150° C., 200° C., 300° C., 350° C. or 400° C. As would be readily appreciated by a worker skilled in the art, the stability of the precursor compound can change depending on its physical state. For example, when the precursor is in a liquid state (as it usually is in the bubbler used for ALD), then the precursor compound will remain stable for extended periods of time at temperatures up to at least about 100° C., 150° C. or 200° C.

In accordance with one embodiment, the precursor compound will exhibit less than about 2% decomposition (by weight), or less than about 1% decomposition (by weight) following 1 week at about 10° C. above ALD source temperature.

The mono-metallic precursor compounds described herein have been developed to be useful in ALD, however, it should be readily apparent that these compounds may also be useful in other metal deposition processes, such as CVD.

In accordance with one aspect, there is provided a mono-metallic precursor compound comprising a diaminocarbene (DAC) having the general formula of Formula I:

DAC-M-X    I where M is a metal; and X is an anionic ligand, and where the DAC is a diaminocarbene that is an optionally substituted, saturated N-heterocyclic diaminocarbene (sNHC) or an optionally substituted acyclic diaminocarbene. In a preferred embodiment, M is a group 11 metal, such as copper, silver or gold.

In accordance with one aspect, there is provided a mono-metallic precursor compound comprising an sNHC having the general formula of Formula I:

sNHC-M-X    Ia where M is metal; and X is an anionic ligand. In a preferred embodiment, M is a group 11 metal, such as copper, silver or gold.

As defined above, the DAC component of the precursor compound is a diaminocarbene having a carbenic atom bridging two nitrogen atoms. The metal is bound to the DAC at the carbenic atom via a dative bond. Also, M is bound to X at a non-halogenic atom of the anionic ligand, in order to avoid contamination by halogen during metal deposition. In a specific embodiment, the anionic ligand does not include a halogen atom at any position.

The precursor compound defined above does not comprise any aryl or heteroaryl group.

In one embodiment of the group 11 mono-metallic precursor compound is a compound of Formula IIa:

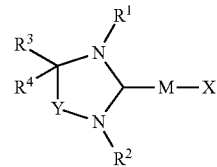

IIa

X is an anionic ligand;
M is a metal, for example a group 11 metal, such as, copper, silver or gold;
Y is $CR^5R^6$, $(CR^5R^6)_2$, or $NR^9$;
$R^1$ and $R^2$ are each independently H, or an optionally substituted, branched, straight or cyclic aliphatic group, wherein $R^1$ and $R^2$ do not comprise a halo substituent;
$R^3$, $R^4$, $R^5$ and $R^6$ are each independently H, or an optionally substituted, branched, straight or cyclic aliphatic group; and
$R^9$ is absent or H, or an optionally substituted, branched, straight or cyclic aliphatic group, wherein, when $R^9$ is absent, the bond between N and the adjacent C is a double bond and $R^3$ or $R^4$ is absent,
and wherein the compound does not comprise an aryl or heteroaryl group, and M is bound to a non-halogenic atom of X. In a preferred embodiment, M is a group 11 metal, such as copper, silver or gold.

In accordance with another aspect, there is provided a compound of Formula IIb:

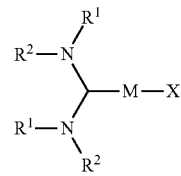

IIb wherein
X is an anionic ligand;
M is a metal, for example, a group 11 metal, such as, copper, silver or gold; and
each $R^1$ and $R^2$ is independently H, or an optionally substituted, branched, straight or cyclic aliphatic group, wherein $R^1$ and $R^2$ do not comprise a halo substituent, and wherein the compound does not comprise an aryl or heteroaryl group and M is bound to a non-halogenic atom of X.

It should be understood that in the compound of Formula IIb, the two $R^1$ substituents can be different from one another and from each of the two $R^2$ substituents. Similarly, it should be understood that the two $R^2$ substituents can be different from one another and from each of the two $R^1$ substituents. Specifically, the structure of Formula IIb encompasses compounds having four different substituents at the two nitrogens.

In accordance with a specific embodiment, M is Cu(I), Ag(I) or Au(I). In accordance with a more specific embodiment, M is Cu(I).

In accordance with a specific embodiment, X is:

where $R^7$ and $R^8$ are each independently an optionally substituted linear, branched or cyclic aliphatic group, an optionally substituted linear or straight $C_1$ to $C_{12}$ alkylsilyl, or $R^7$ and $R^8$ together with the amide nitrogen form an optionally substituted heterocycle.

In accordance with certain embodiments, $R^1$, $R^2$, $R^3$, $R^4$, $R^5$ and $R^6$ are each independently H, an optionally substituted $C_1$ to $C_{12}$ alkyl or heteroalkyl or an optionally substituted $C_3$ to $C_{12}$ cycloalkyl or cyclic heteroalkyl. In alternative embodiments, $R^1$, $R^2$, $R^3$, $R^4$, $R^5$ and $R^6$ are each independently H, an optionally substituted $C_1$ to $C_6$ alkyl or heteroalkyl or an optionally substituted $C_3$ to $C_8$ cycloalkyl or cyclic heteroalkyl.

In accordance with a particular embodiment, $R^1$ and $R^2$ are each independently H, an optionally substituted branched or straight $C_1$ to $C_{12}$ alkyl or heteroalkyl, wherein $R^1$ and $R^2$ do not comprise any halide atoms.

In accordance with another particular embodiment the anionic ligand X is selected such that there are no metal-oxygen bonds (e.g., Cu—O) within the mono-metallic precursor compound. In a related embodiment, the mono-metallic precursor compound does not form metal oxide films when used in ALD. Alternatively, if the absence of oxygen is not required, the anionic ligand X can be an oxygen containing ligand, such as an alkoxide, bound to the metal via the oxygen atom.

In accordance with another embodiment, the precursor compound does not include any oxygen atoms. For example, the presence of oxygen anywhere in the precursor can lead to oxidation of oxidizable layers, such as the tantalum nitride barrier layer often used in semiconductor manufacture. Similarly, the reactive gas should not contain oxygen when the metal deposition substrate includes an oxidizable layer, such as a tantalum nitride barrier layer.

Another consideration in selection of an anionic ligand is the presence of hydrogen atoms in the ligand at a position beta to the metal atom. The presence of β-hydrogen atoms can result in decomposition of the precursor compound via elimination of the ligand with concomitant formation of unstable metal hydrides.

Metal hydrides are commonly unstable and very reactive. β-Hydrogen eliminations occurring in a precursor source container would deplete the precursor as well as create unwanted reactive species. β-Hydrogen elimination at the deposition surface would lead to non self-limiting behaviour, i.e., CVD growth. This can be avoided by not having β-hydrogens in the anionic ligand or by designing the anionic ligand so that any β-hydrogens are not accessible to the metal center (i.e., there is no reaction pathway for the β-hydrogen to form a intermediate bond that would lead to β-hydride transfer).

As described above, decreasing steric bulk can increase volatility of a precursor compound because of a concomitant decrease in molecular weight. Accordingly, steric bulk is one consideration for selection of the anionic ligand and the substituents on the sNHC. Although decreasing steric bulk can increase volatility of the precursor compound, care must be taken to maintain sufficient steric bulk to avoid formation of dimeric complexes.

Specific examples of group 11 mono-metallic precursor compounds are shown below:

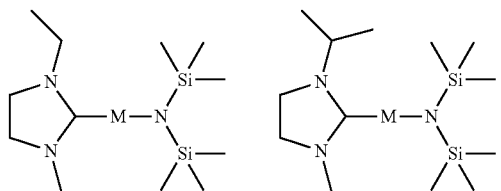

1a, M = Cu
1b, M = Ag
1c, M = Au

2a, M = Cu
2b, M = Ag
2c, M = Au

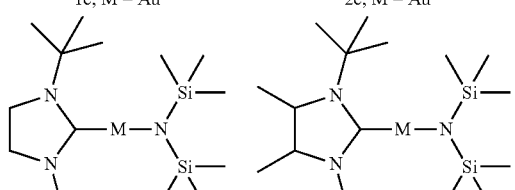

3a, M = Cu
3b, M = Ag
3c, M = Au

4a, M = Cu
4b, M = Ag
4c, M = Au

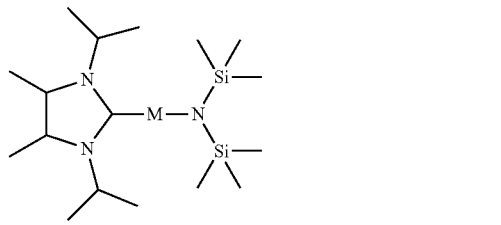

5a, M = Cu
5b, M = Ag
5c, M = Au

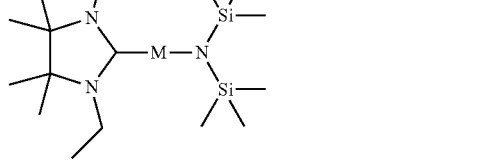

6a, M = Cu
6b, M = Ag
6c, M = Au

-continued

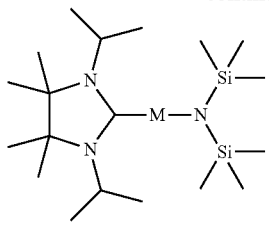

7a, M = Cu
7b, M = Ag
7c, M = Au

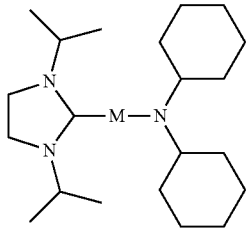

8a, M = Cu
8b, M = Ag
8c, M = Au

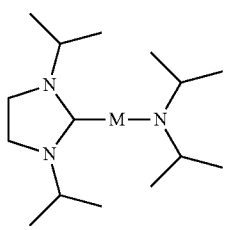

9a, M = Cu
9b, M = Ag
9c, M = Au

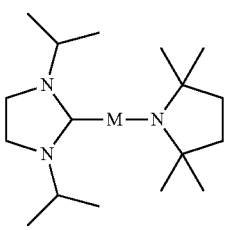

10a, M = Cu
10b, M = Ag
10c, M = Au

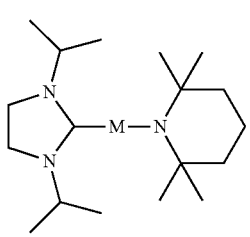

11a, M = Cu
11b, M = Ag
11c, M = Au

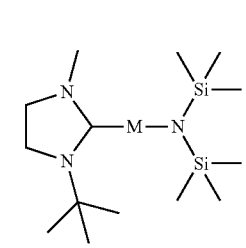

12a, M = Cu
12b, M = Ag
12c, M = Au

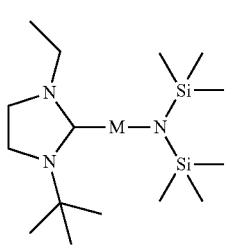

13a, M = Cu
13b, M = Ag
13c, M = Au

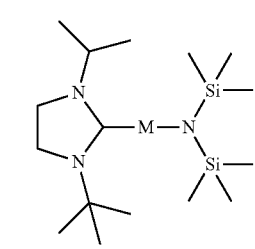

14a, M = Cu
14b, M = Ag
14c, M = Au

-continued

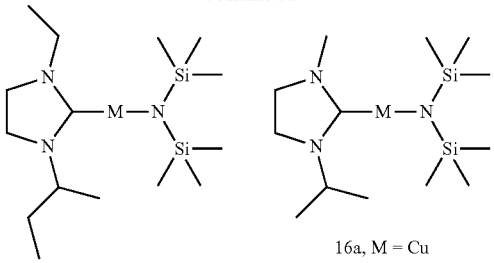

15a, M = Cu
15b, M = Ag
15c, M = Au

16a, M = Cu
16b, M = Ag
16c, M = Au

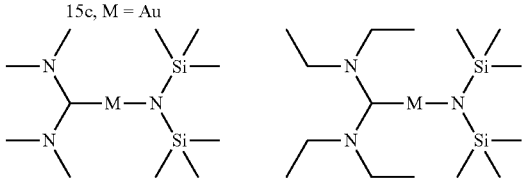

17a, M = Cu
17b, M = Ag
17c, M = Au

18a, M = Cu
18b, M = Ag
18c, M = Au

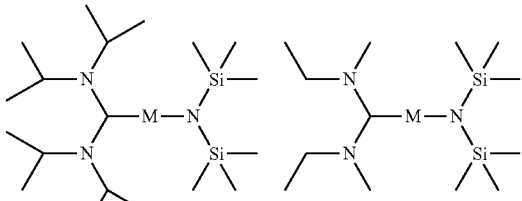

19a, M = Cu
19b, M = Ag
19c, M = Au

20a, M = Cu
20b, M = Ag
20c, M = Au

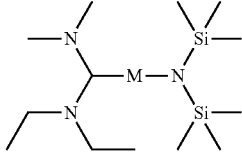

21a, M = Cu
21b, M = Ag
21c, M = Au

Compounds 1a, b, c to 21a, b, c, are useful as precursor compounds in ALD. In some instances, compounds 1a, b, c to 21a, b, c may also be useful in CVD.

U.S. Patent Publication No. 2009/0004385, which is herein incorporated by reference in its entirety, discloses a limited number of compounds having the general structure:

NHC—Cu—Y where the NHC is an imidazol-2-ylidene, the Cu is bound to the NHC at the carbenic atom and Y is an anionic ligand. The disclosed compounds all include an unsaturated NHC. These compounds are purported to be useful as copper precursors in chemical phase deposition, such as ALD.

Interestingly, however, the present inventors have found that a compound having the structure of Formula III (1,3-diisopropyl-4,5-dimethyl-imidazol-2-ylidene copper hexamethyldisilazide), shown below, which comprises an unsaturated NHC, was unsuccessful as a copper precursor in ALD.

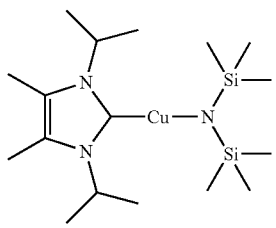

III

As detailed in the Examples below, the compound 2a was used to successfully deposit a copper thin film on a substrate in an ALD process. Compound 2a was volatilised at 90° C. and deposited copper by plasma-enhanced ALD at 225° C. using $H_2$ (20 sccm) in Ar (140 sccm) as the plasma supply gas. The growth rate for the films was about 0.21 Å/cycle. A saturation curve was generated (FIG. 22), which confirmed that this process undergoes self-limited (i.e., ALD) growth.

Copper metal deposition was attempted using the compound of Formula III, which is an unsaturated analogue of compound 2a, under conditions similar to those successfully employed with compound 2a. With the compound of Formula III used as the precursor, copper metal could not be repeatably deposited. During the process, spots of copper as well as spots of non-conductive, apparently transparent material were commonly co-deposited. This led to the conclusion that this precursor did not produce a stable, self-limiting monolayer. Rather it may have undergone thermal decomposition to produce a film that incorporated copper as well as a large amount of impurities from the ligand system.

Figure 3:
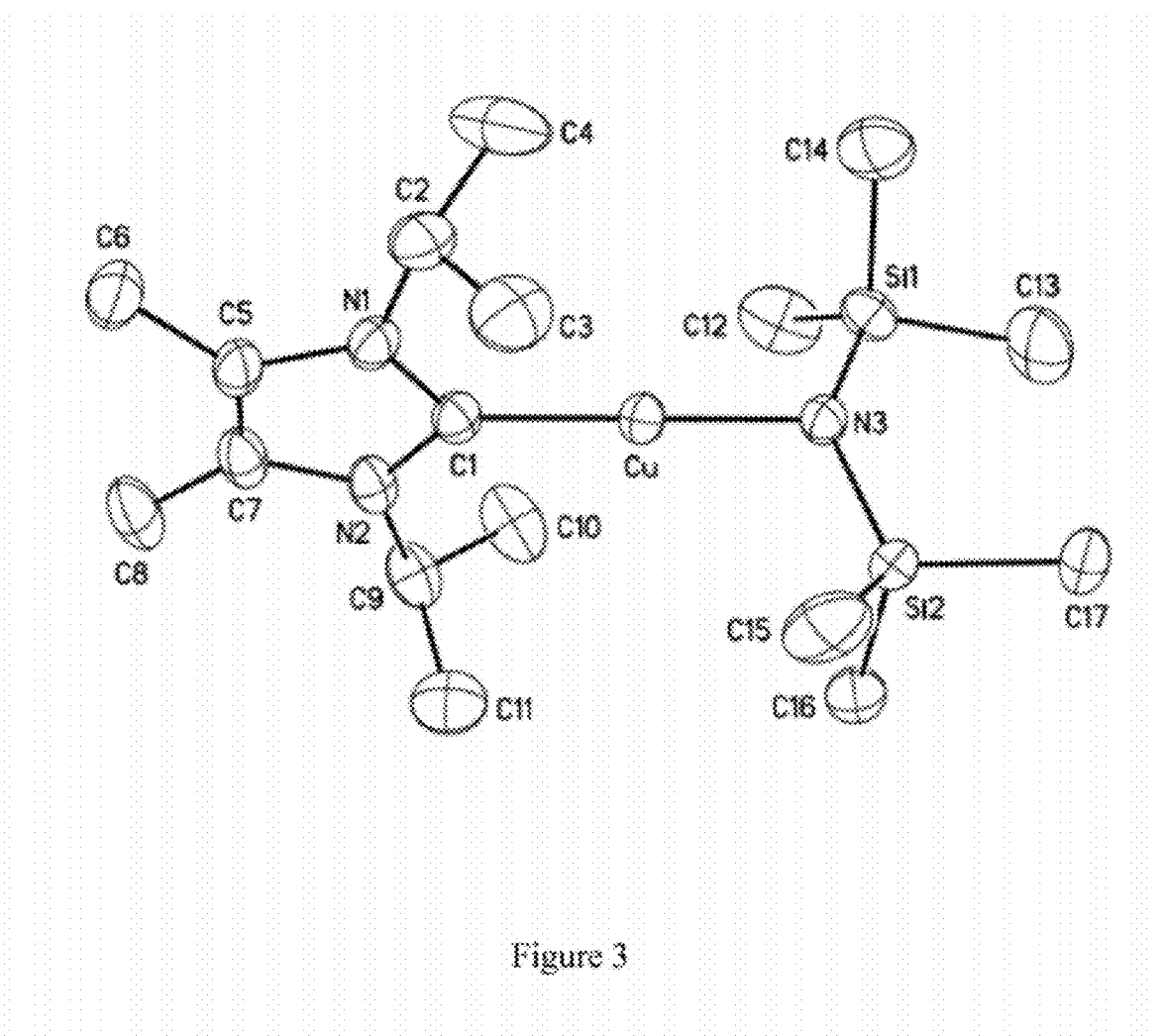
FIG. 3 is an ORTEP drawing of the X-ray crystal structure of 1,3-diisopropyl-4,5-dimethyl-imidazol-2-ylidene copper hexamethyldisilazide.

Without wishing to be bound by theory, the suitability of the precursor compounds of Formulae Ia and IIa for ALD may be due to the saturated and sterically accessible backbone of the sNHC. Alternatively, or in addition, the poor results obtained using the compound of Formula III in ALD may result from intermolecular stacking of molecules of the compound of Formula III resulting in reduced accessibility and/or reactivity. As shown in FIG. 3, the unsaturated N-heterocyclic carbene in the compound of Formula III is planar, which likely results in intermolecular stacking (sometimes referred to as π-stacking although the interactions between the N-heterocyclic carbene may not be limited to π-π interactions), thus reducing the reactivity of the compound and its suitability for ALD. The sNHC-containing mono-metallic precursor compounds described herein are designed such that they do not comprise any aryl or heteroaryl functional groups in order to avoid such intermolecular stacking International PCT Publication No. WO 2006/012294, which is herein incorporated by reference in its entirety, discloses a broad class of main group and transition metal chemical vapour deposition precursors that incorporate nucleophilic stable carbene ligands. Within the broad class of carbene ligands, WO 2006/012294 generically identified sNHCs without identifying any specific sNHC ligands as being made or tested in precursor compounds. The purported precursors disclosed in WO 2006/012294 were suggested to be useful in CVD only. Nowhere in WO 2006/012294 is there any teaching or discussion relating to ALD.

The mono-metallic precursor compounds of Formula I, Ia, IIa and IIb, as described herein, have now been found to be effective precursors in ALD of a metal to a substrate, for example, deposition of a thin film of copper to a substrate.

As described above, there are five principles used in designing ALD precursors. The identification of precursors having sufficient volatility and thermal stability can be achieved by various means. A specific example of a useful technique is thermogravimetric ("TG") analysis.

TG analysis measures the amount and rate of change in the mass of a sample as a function of temperature ("Δm/ΔT") or time ("Δm/Δt") in a controlled atmosphere. As used in the present application, the measurements are used primarily to determine the thermal stabilities of precursor compounds, as well as their volatility.

TG analysis measurements provide valuable information that can be used to select precursor compounds useful in ALD and to predict precursor performance. In a typical TG analysis, a precursor compound under study is subjected to increasing temperatures with mass measurements obtained at set time intervals.

A TG graph can be used to demonstrate the volatility of a potential precursor compound. In a TG graph, a volatile compound will produce a curve demonstrating a slow onset of weight loss followed by a rapid drop off. A low residual mass (e.g., <2%) following a TG experiment, is a definite indicator of compound volatility. A residual mass that is >2%, but less than the metal content of the complex is indicative of, at least, partial volatility of a metal-containing species during the experiment.

A TG graph can also be used to demonstrate the thermal stability of a potential precursor compound. A single featured weight loss curve that is characteristic of volatility and has a residual mass of <2% is an indicator that the compound was thermally stable within the temperature range and time span of the weight loss event.

TG analyses performed using sNHC-containing mono-metallic precursor compounds as described herein and an unsaturated analog thereof, have shown that the sNHC-containing compounds have superior volatility and thermal stability in comparison to an unsaturated analog. Details of these analyses are provided in the Examples below.

Synthesis

The DAC precursor compounds can be prepared using a variety of synthetic methods. The synthetic reactions shown in the below scheme and described herein, are illustrative only. Other synthetic routes can be employed, as would be within the abilities of a worker skilled in the art, based on the disclosure herein.

In accordance with one embodiment, the metal precursor compounds can be prepared using a method that employs salt metathesis. A specific example of such a synthetic method is depicted in the scheme below:

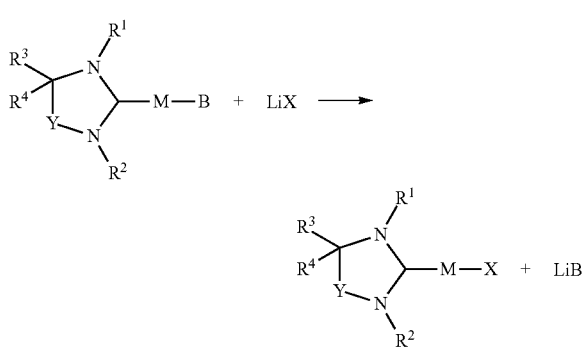

where X is a anionic ligand;
M is a group 11 metal, for example, copper, silver or gold;
B is a halide, such as a chloride, bromide or iodide;
Y is $CR^5R^6$, $(CR^5R^6)_2$, or $NR^S$;

$R^1$ and $R^2$ are each independently H, or an optionally substituted linear, branched or cyclic aliphatic group, wherein $R^1$ and $R^2$ do not comprise any halide atoms; and $R^3$, $R^4$, $R^5$ and $R^6$ are each independently H, or an optionally substituted linear, branched or cyclic aliphatic group.

In one embodiment, $R^1$, $R^2$, $R^3$, $R^4$, $R^5$ and $R^6$ are each independently H, a $C_1$ to $C_{12}$ alkyl or heteroalkyl, or a $C_3$ to $C_{12}$ cycloalkyl or cyclic heteroalkyl.

As would be appreciated by a worker skilled in the art, although the above method includes the use of a lithium salt, the method can also be performed using a different salt of the anionic ligand, such as a sodium or potassium salt.

The carbene metal halide compound can be provided as an isolated starting material or an unisolated intermediate. In either option the carbene metal halide can be synthesized by treating a carbene salt, such as a carbene halide salt, with a group 11 metal halide, such as CuCl, under basic conditions.

In accordance with another embodiment, the compounds can be synthesized by a method including the step of cleaving a metal oligomer, or metal dimer, with a saturated NHC.

Alternatively, the mono-metallic precursor compounds can be prepared using a synthetic route analogous to the method used in U.S. Patent Publication No. 2009/0004385 to prepare copper precursors that contain an unsaturated NHC.

In another alternative, the mono-metallic precursor compounds can be prepared using a methane elimination and ligand exchange as described in *Inorg. Chem.*, 2006, 45(22), 9032-9045.

In an alternative approach, the starting materials are sNHC.HCl, CuCl, and two equivalents of base to make the final complex. In this approach, the base would be the amide salt.

Figure 4:
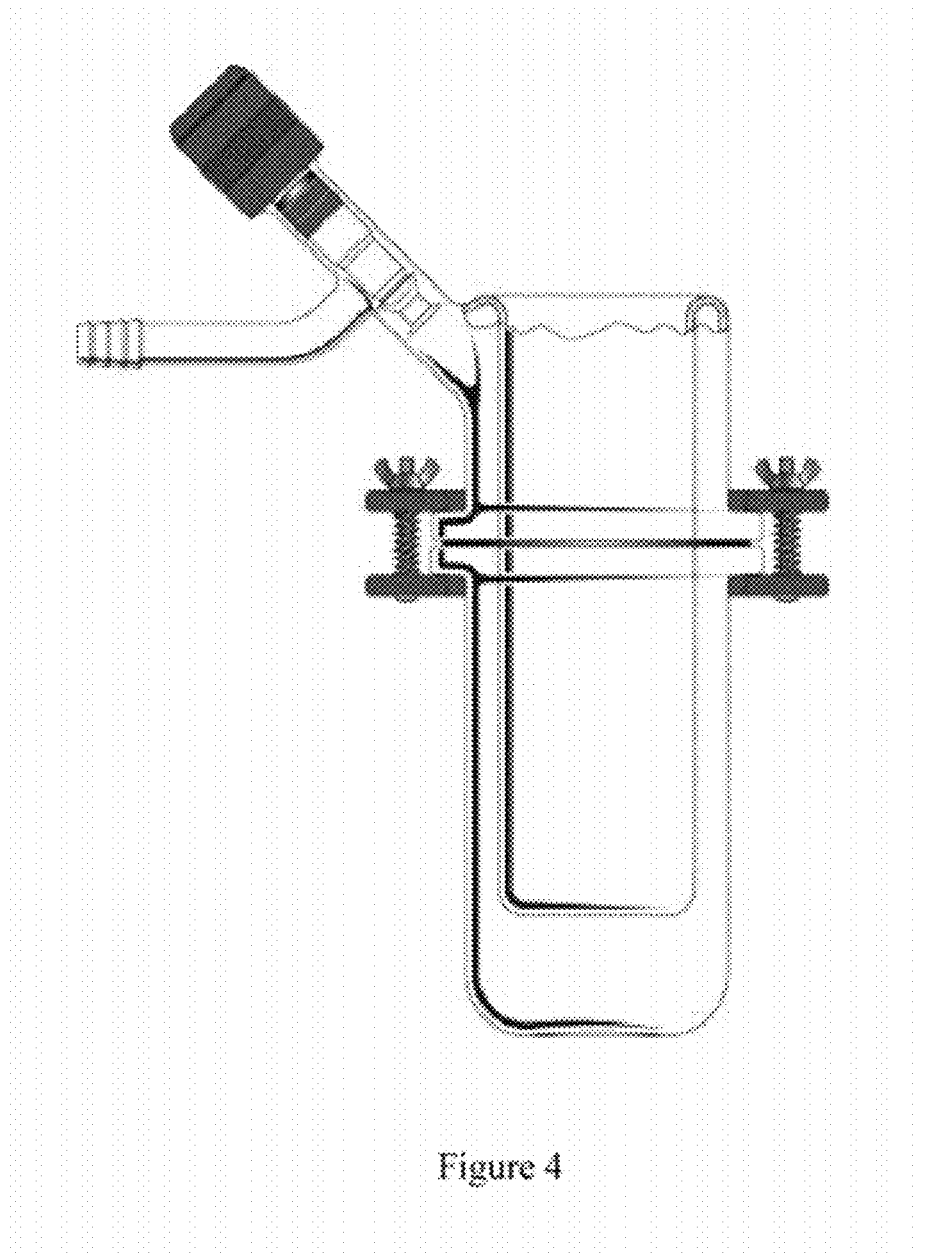
FIGS. 4-6 are depictions of sublimation apparatuses.
Figure 5:
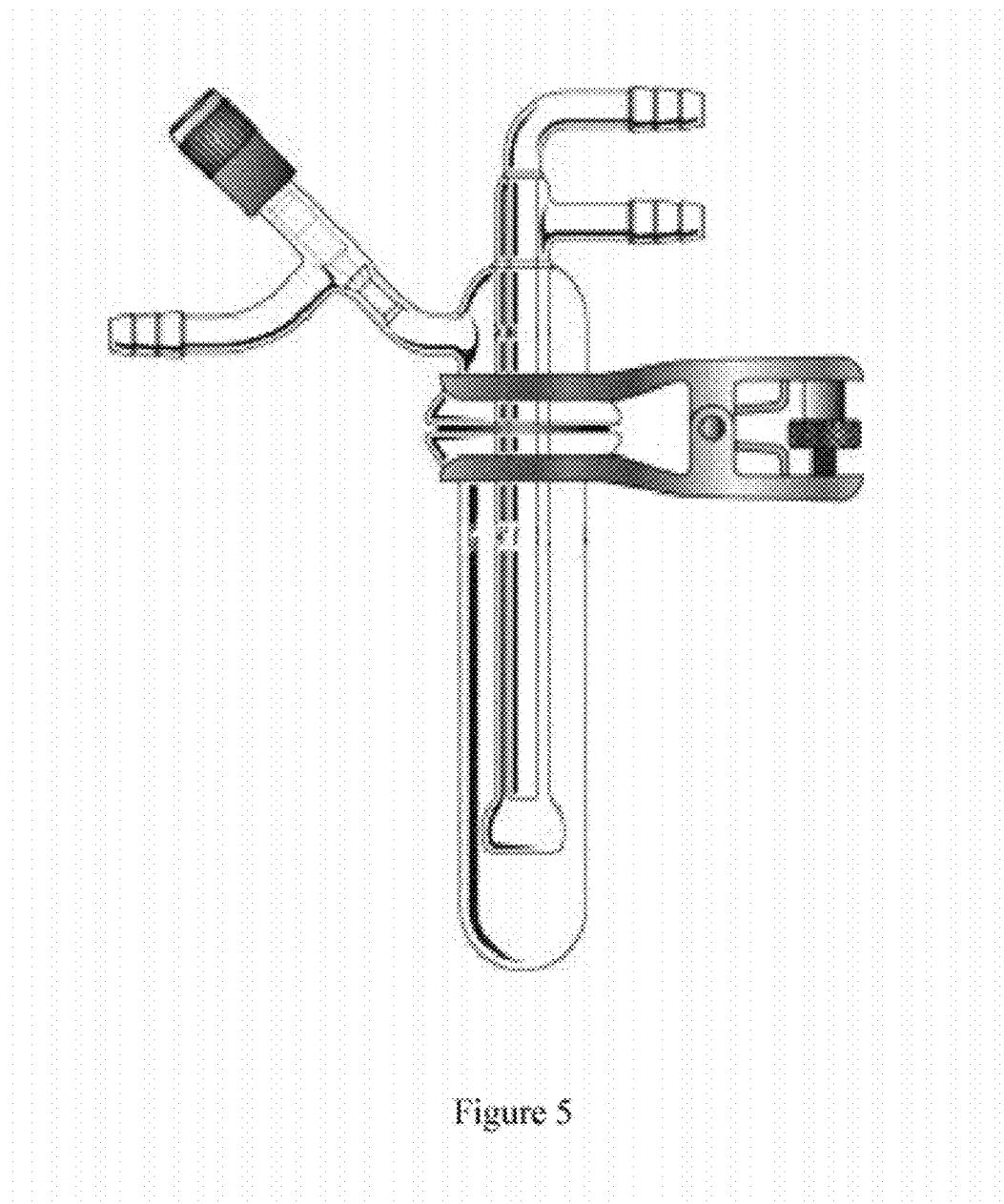
Figure 6:
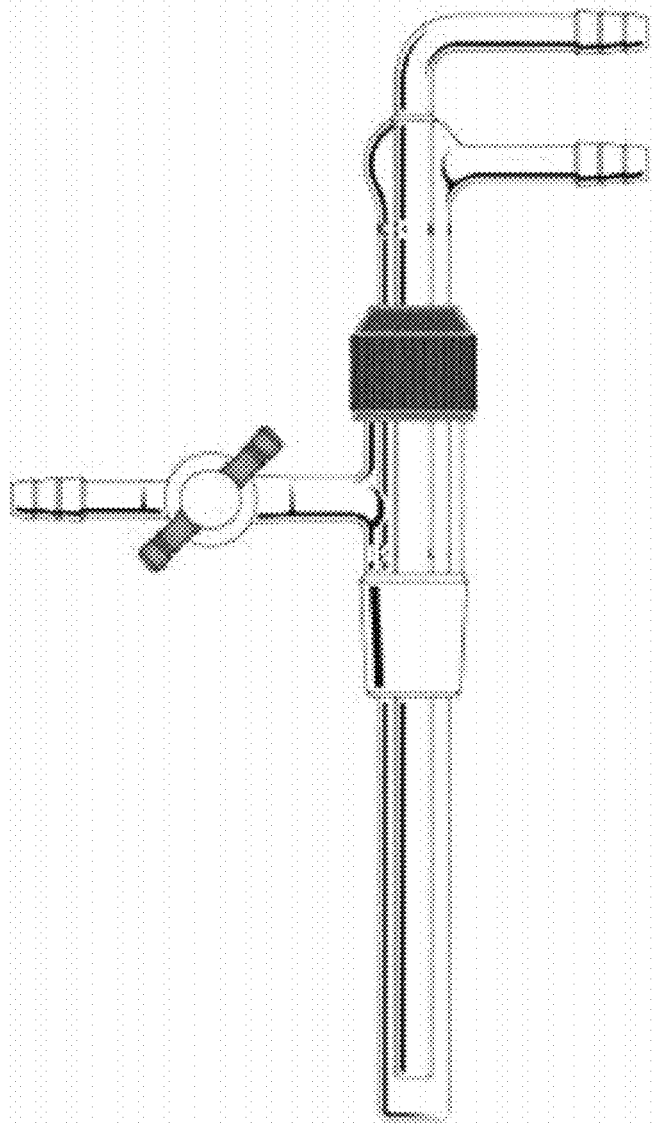

Following synthesis, the precursor compounds can be purified if the product of the synthetic method is not sufficiently pure to be used in ALD. For example, the precursor compounds can be purified by recrystallization, distillation, sublimation in a sublimation apparatus, or any combination thereof. Examples of suitable sublimation apparatuses are depicted in FIGS. 4-6. In accordance with one embodiment, the precursor compounds are sufficiently pure to be used in ALD, for example, to produce a film of at least about 95% purity. In accordance with a specific embodiment, the precursor compounds are at least 95% pure. Preferably, the precursor compounds are at least 98% pure. More preferably, the precursor compounds are 99.98% pure (e.g., when prepared as electronic grade chemicals).

Metal Deposition

The DAC metal precursor compounds disclosed herein are useful in deposition of metal thin films by any deposition methods known to those of skill in the art. Examples of suitable deposition techniques include, without limitation chemical vapour deposition (CVD), plasma enhanced chemical vapour deposition (PE-CVD), atomic layer deposition (ALD), plasma enhanced atomic layer deposition (PE-ALD) and the like. Accordingly, another aspect provides a method and system for deposition of a thin film of metal on a substrate using a DAC metal precursor compound.

In an embodiment, a first precursor is introduced into a reactor in vapour form. The precursor in vapour form can be produced by vaporizing a liquid precursor solution, through a conventional vaporization step such as direct vaporization, distillation, or by bubbling an inert gas (e.g. $N_2$, He, Ar, etc.) into the precursor solution and providing the inert gas plus precursor mixture as a precursor vapour solution to the reactor. Bubbling with an inert gas can also remove any dissolved oxygen present in the precursor solution. In other alternatives, the precursor is introduced into the reactor via liquid injection or an aerosol-assisted bubbler.

The reactor can be any enclosure or chamber within a device in which deposition methods take place such as without limitation, a cold-wall type reactor, a hot-wall type reactor, a single-wafer reactor, a multi-wafer reactor, or other types of deposition systems, under conditions suitable to cause the precursors to react and form the layers. Specific, non-limiting, example of reactors suitable for ALD using an DAC metal precursor are the F-120 ALD reactor (ASM Microchemistry Ltd., Finland; for thermal ALD) and the TFS 200 ALD reactor (BENEQ, Finland; for plasma ALD) and the SUNALE™ R-200 ALD reactor (Picosun, Finland; for plasma ALD).

Generally, the reactor contains one or more substrates onto which the thin films will be deposited. The one or more substrates can be any suitable substrate used, for example, in semiconductor, photovoltaic, flat panel, or LCD-TFT device manufacturing, or non-electronic applications such as optics, catalysis, sensors and so on. Alternatively, a thin film/substrate composite material is useful in microelectromechanical systems (MEMS), such as sensors, thermal actuators, voltaic actuators, accelerometers, microfluidic devices, etc.

Examples of suitable substrates include without limitation, glass, TaN, TiN, sapphire, indium tin oxide (ITO), $SiO_2$, silicon, silicon nitride, silicon oxy nitride, silicon oxycarbide, fused silica, polymeric materials, tungsten, tantalum, ruthenium, other metals, organic materials or combinations thereof. The substrate can also have one or more layers of differing materials already deposited upon it from a previous manufacturing step. Optionally, the surface of the substrate is cleaned, using standard methods, prior to the film deposition process.

In some embodiments, in addition to the first precursor, a reactant gas or a secondary precursor, can be introduced into the reactor at the appropriate time. In some of these embodiments, the reactant gas can be an oxidizing gas such as one of oxygen, ozone, water, hydrogen peroxide, nitric oxide, nitrogen dioxide, radical species of these, as well as mixtures of any two or more of these. In some other of these embodiments, the reactant gas can be a reducing agent such as one of hydrogen, a forming gas (i.e., ~5% hydrogen, ~95% nitrogen mixture) ammonia, a silane, a borane, an amino borane, an alane, formic acid, a hydrazine (e.g., dimethylhydrazine), a radical species of thereof, or a mixture of any two or more of these reducing agents.

In an alternative embodiment, the reactant gas can be a formic acid/hydrazine combination (Knisley, T. J., et al., *Chem. Mater.*, 2011, 23, 4417-4419) or ethyl iodide (Au, Y., Lin, Y., and Gordon, R. G., *J. Elect. Soc.*, 2011, 158(5), D248-D253). When ethyl iodide is employed as the reactant gas, the method is useful for bottom-up filling. Bottom-up filling of features with high aspect ratios is an improvement for CVD to fill features without seams or voids. It has been shown that pre-treatment of suitable substrates with ethyl iodide vapour leads to accelerated film growth for copper CVD processes using copper(I) diketonates and copper(I) amidinates. Without wishing to be bound by theory, it is thought that dissociated iodine atoms on the surface weaken the copper ligand bond and ease the reduction to copper metal by a reducing agent. When an ethyl iodide pre-treatment step is used to fill features of high aspect ratios, growth at the bottom of the feature continuously accelerates as the surface area decreases and the iodine atom concentration increases there by allowing for bottom-up filling and eliminating seems and voids in the feature.

In some embodiments, and depending on what type of film is desired to be deposited, a second metal-containing precursor can be introduced into the reactor. Such a second metal-containing precursor can comprise a metal source, such as, but not limited to, copper, silver, gold, praseodymium, manganese, ruthenium, titanium, tantalum, bismuth, zirconium, hafnium, lead, niobium, magnesium, aluminum, tungsten, lanthanum, or mixtures of these, which is the same or different as the metal in the first precursor. In embodiments where a second metal-containing precursor is utilized, the resultant film deposited on the substrate can contain at least two different metal types in separate layers of a multilayer film, where the first metal-containing precursor, the second metal-containing precursor, or both, is a DAC metal containing precursor as described herein. Alternatively, in embodiments where a second metal-containing precursor is used, the film deposited on the substrate comprises at least two different metals within one or more layers of a multilayer film.

The first precursor and any optional reactants or precursors can be introduced sequentially (as in ALD) or simultaneously (as in CVD) into the reaction chamber. In some embodiments, the reaction chamber is purged with an inert gas between the introduction of the precursor and the introduction of the reactant. In some embodiments, the reactant can be excited species contained in a plasma. One of skill in the art would generally recognize methods and apparatus suitable for plasma reaction with an ALD or CVD precursor.

Depending on the particular process parameters, deposition can take place for a varying length of time. Generally, deposition can be allowed to continue as long as desired or necessary to produce a film with the necessary properties. Typical film thicknesses may vary from several angstroms to several hundreds of microns, depending on the specific deposition process. The deposition process can be performed as many times as necessary to obtain the desired film properties or thickness.

In some embodiments, the temperature and the pressure within the reactor are held at conditions suitable for ALD or CVD depositions. For instance, the pressure in the reactor may be held between about 1 Pa and about $10^5$ Pa, or preferably between about 25 Pa and $10^3$ Pa, as required per the deposition parameters. Likewise, the temperature in the reactor may be held between about 50° C. and about 500° C., preferably between about 50° C. and about 400° C.

In some embodiments, the precursor vapour solution and the reaction gas, can be pulsed sequentially or simultaneously (e.g., pulsed CVD) into the reactor. Each pulse of precursor can last for a time period ranging from about 0.01 seconds to about 10 seconds, alternatively from about 0.3 seconds to about 8 seconds, alternatively from about 1 seconds to about 6 seconds. In another embodiment, the reaction gas may also be pulsed into the reactor. In such embodiments, the pulse of each gas may last for a time period ranging from about 0.01 seconds to about 10 seconds, alternatively from about 0.3 seconds to about 8 seconds, alternatively from about 1 seconds to about 6 seconds.

As described above, ALD is an alternative method to CVD for depositing conformal, ultra-thin films at comparatively lower temperatures. ALD is similar to CVD except that the substrate is sequentially exposed to one reactant at a time, or one dose of a reactant at a time. This means that the films are expected to be more uniform and more readily controlled when manufactured using ALD rather than CVD.

ALD is described in Finnish patent publications 52,359 and 57,975 and in U.S. Pat. Nos. 4,058,430 and 4,389,973. Apparatuses suited to implement these methods are disclosed in U.S. Pat. Nos. 5,855,680, 6,511,539, and 6,820,570, Finnish Patent No. 100,409 Material Science Report 4(7)(1989), p. 261, and Tyhjiotekniikka (Finnish publication for vacuum techniques), ISBN 951-794-422-5, pp. 253-261, which are incorporated herein by reference in their entirety. A basic ALD apparatus includes a reactant chamber, a substrate holder, a gas flow system including gas inlets for providing reactants to a substrate surface and an exhaust system for removing used gases. Apparatuses for ALD are commercially available.

Thermal ALD of metals relies on thermally-activated reactions between two precursors: a metal-containing precursor compound and a reactant precursor, such as a reducing agent. This method may be preferred in situations in which a clean process is required and/or where specialized equipment is not available. FIG. 1 provides a general schematic of a thermal deposition process using a copper precursor compound and a reducing agent.

In one example of thermal ALD using, for example, an ASM F-120 reactor, a small amount of precursor (0.3-0.5 g) is loaded into an open-topped precursor boat. This boat is inserted into the source tube of the reactor. Another source tube is fitted with hydrogen gas using a vacuum flange, and the flow is controlled to about 10 sccm with a mass flow controller. In a specific example, a 5 cm×5 cm silicon substrate (with its native oxide intact) is submitted to the deposition zone, and the entire apparatus is brought down to roughing pump vacuum. The precursor boat is heated to 90° C., and the substrate is heated to 225° C. Generally, there is a uniform ramp of temperature between the precursor boat and the deposition zone to prevent condensation of the precursor in the apparatus. Nitrogen gas, or another inert gas, is used in a continual purge of about 100 sccm to purge the reactor, and through controlling the valving, this purge gas is also used as a carrier gas for the precursor and a reducing gas, such as hydrogen. The valving can be programmed to deliver a pulse of precursor for 2 seconds, with a purge of 2 seconds. This can be followed by a pulse of hydrogen for 2 seconds, followed by a purge of 2 seconds. In a typical experiment, this pulse sequence (i.e., the ALD cycle) is repeated for anywhere between 300 and 3000 times.

Figure 2:
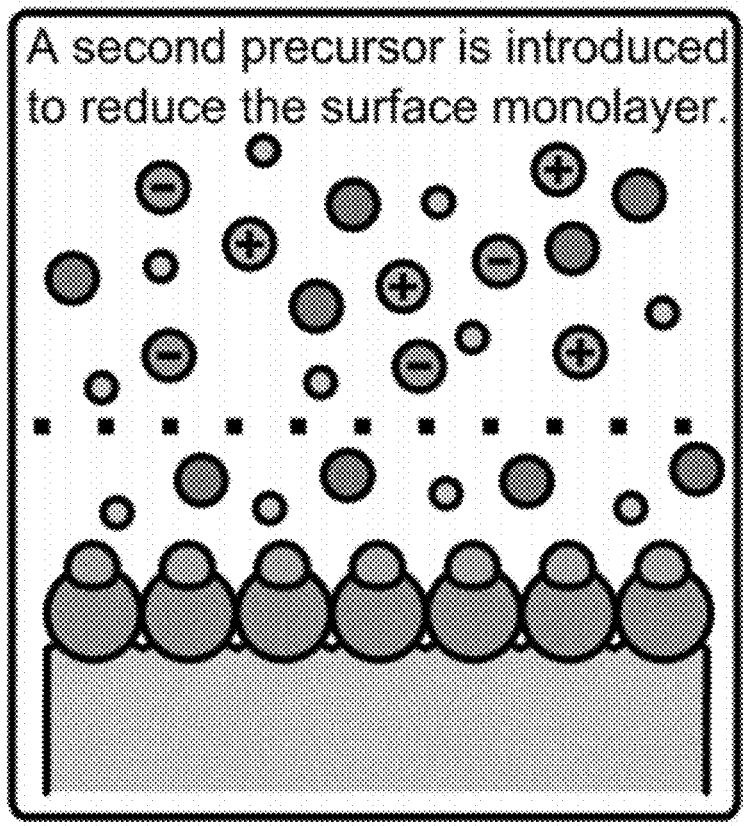
FIG. 2 is a schematic representation of a step in plasma ALD in which a second precursor/reactant is introduced to reduce the surface monolayer.

An alternative to thermal ALD is plasma-enhanced ALD (PE-ALD). It is generally known in substrate deposition processes to employ excited species, particularly radicals, to react with and/or decompose chemical species at the substrate surface to form the deposited layer. In PE-ALD, the reactant precursor is a plasma, which contains radicals, ions, electrons and photons. Radical enhanced plasma ALD is a subset of PE-ALD, which includes the step of screening out the ions (which can lead to undesired effects) leaving the radicals to reduce the surface monolayer. FIG. 2 provides a schematic of radical enhanced plasma ALD.

In one example of PE-ALD in, for example, a BENEQ TFS 200 reactor, a small amount of precursor (0.3-0.5 g) is loaded into an open-topped precursor boat. This boat is inserted into the source tube of the reactor. Through internal valving, a pressure of about 140 sccm nitrogen, or other inert gas, is used as the carrier gas for the precursor, while the reactor is purged with 330 sccm of nitrogen. A flow of 20 sccm $H_2$ in 140 sccm nitrogen is used as the plasma source. In a specific example, a silicon substrate with its native oxide intact is introduced on a wafer plate through a load lock. The precursor boat is heated to, for example, about 90° C., and the substrate is heated to, for example, about 225° C. Selection of the appropriate heating temperatures of the precursor boat and the substrate can be made by any person skilled in the art, based, at least in part, on the nature of the precursor and/or substrate. Generally, there is a uniform ramp of temperature between the precursor boat and the deposition zone to prevent condensation of the precursor in the apparatus. Preferably, the plasma employs screens to prevent ions from reaching the substrate. It should be noted that, in this example, the reaction chamber always has about 160 sccm of $H_2/N_2$ flowing through it, and this gas is not pulsed. The valving is programmed to deliver a 1 second pulse of precursor followed by 3 seconds of purging with nitrogen. The plasma pulse is controlled by the plasma generator, which is programmed to deliver a 6 second pulse of hydrogen plasma after the precursor purge, followed by 3 seconds of purging. Typically, this pulse sequence (i.e., the ALD cycle) was repeated for anywhere between 300 and 3000 times.

In one embodiment of the present invention, there is provided a metal deposition process that combines ALD and CVD processes, for example, in the manufacture of a product having layers of different metals.

Also provided herein are systems and compositions comprising a mono-metallic DAC precursor compound. In specific embodiments the mono-metallic DAC precursor compound is in an air-tight container, such as a flame sealed ampule, or a vial, or tube having a cap that is removably attached to the vial or tube to produce an air-tight seal. In an alternative embodiment, the mono-metallic precursor compound is conveniently packaged in a bubbler configured for use with an ALD tool. Optionally, the DAC precursor compound is packaged under an inert atmosphere (such as, e.g., nitrogen or argon gas). In an alternative embodiment, the DAC precursor compound is in a composition comprising a desiccant, an anti-oxidant or an additive for inhibiting spontaneous decomposition of the DAC precursor compound.

To gain a better understanding of the invention described herein, the following example is set forth. It should be understood that these examples are for illustrative purposes only. Therefore, they should not limit the scope of this invention in any way.

EXAMPLES

Example 1

Reference Example—ALD studies using 1,3-diisopropyl-4,5-dimethyl-imidazol-2-ylidene copper(I) hexamethyldisilazide 1,3-Diisopropyl-4,5-dimethyl-imidazol-2-ylidene copper (I) hexamethyldisilazide (compound of Formula III) was tested as an ALD precursor. In this example, the thermal ALD tests were performed using a SUNALE™ R series ALD (Picosun, Finland).

In each test, a small amount of the compound was loaded into an open-topped precursor boat. This boat was inserted into the source tube of the reactor and the ALD test was performed as detailed below.

Test 1:
Test 1 was performed using the following conditions:

| | |
|---|---|
| Reducing gas: | Forming gas, 5% hydrogen in nitrogen |
| Temperatures: | 110° C. source temperature |
| | 200° C. reactor temperature |
| Pulse sequence: 300 cycles of: | 0.5 second of precursor flow |
| | 5 seconds of nitrogen purge |
| | 4 seconds of forming gas |
| | 10 seconds of nitrogen purge |
| Substrate: Si wafer with 50 nm of $Al_2O_3$ | |

No change in the appearance of the substrate was observed after completion of the test, which indicated that no copper film formed on the substrate.

Test 2:
Test 2 was performed using the following conditions:

| | |
|---|---|
| Reducing gas: | Forming gas, 5% hydrogen in nitrogen |
| Temperatures: | 120° C. source temperature |
| | 300° C. reactor temperature |
| Pulse sequence: 300 cycles of: | 1 seconds of precursor flow |
| | 5 seconds of nitrogen purge |
| | 4 seconds of forming gas |
| | 10 seconds of nitrogen purge |
| Substrate: Si wafer with 50 nm of $Al_2O_3$ | |

No change in the appearance of the substrate was observed after completion of the test, which again indicated that no copper film formed on the substrate.

Test 3:
Test 3 was performed using the following conditions:

| | |
|---|---|
| Reducing gas: | Forming gas, 5% hydrogen in nitrogen |
| Temperatures: | 120° C. source temperature |
| | 350° C. reactor temperature |
| Pulse sequence: 300 cycles of: | 2 seconds of precursor flow |
| | 5 seconds of nitrogen purge |
| | 4 seconds of forming gas |
| | 10 seconds of nitrogen purge |
| Substrate: Si wafer with 50 nm of $Al_2O_3$ | |

No change in the appearance of the substrate was observed after completion of the test, which again indicated that no copper film formed on the substrate.

Test 4:
Test 4 was performed using the following conditions:

| | |
|---|---|
| Reducing gas: | Forming gas, 5% hydrogen in nitrogen |
| Temperatures: | 130° C. source temperature |
| | 400° C. reactor temperature |
| Pulse sequence: 300 cycles of: | 2 seconds of precursor flow |
| | 5 seconds of nitrogen purge |
| | 4 seconds of forming gas |
| | 10 seconds of nitrogen purge |
| Substrate: Si wafer with 50 nm of $Al_2O_3$ | |

No change in the appearance of the substrate was observed after completion of the test, which again indicated that no copper film formed on the substrate.

Test 5:
Test 5 was performed using the following conditions:

| | |
|---|---|
| Reducing gas: | Forming gas, 5% hydrogen in nitrogen |
| Temperatures: | 160° C. source temperature |
| | 450° C. reactor temperature |

-continued

| Pulse sequence: 300 cycles of: | 2 seconds of precursor flow |
| --- | --- |
| | 5 seconds of nitrogen purge |
| | 4 seconds of forming gas |
| | 10 seconds of nitrogen purge |
| Substrate: Si wafer with 50 nm of $Al_2O_3$ | |

No change in the appearance of the substrate was observed after completion of the test, which again indicated that no copper film formed on the substrate.

Test 6:

Test 6 was performed using the following conditions:

| Reactant gas: | $H_2O$ |
| --- | --- |
| Temperatures: | 160° C. source temperature |
| | 300° C. reactor temperature |
| Pulse sequence: 400 cycles of: | 1.5 seconds of precursor flow |
| | 5 seconds of nitrogen purge |
| | 0.4 seconds of water |
| | 10 seconds of nitrogen purge |
| Substrate: Si wafer with 50 nm of $Al_2O_3$ | |

A slight brown film was observed on the substrate after completion of the test. Copper was detected in the brown film using X-ray photoelectron spectroscopy.

These tests demonstrated that the 1,3-diisopropyl-4,5-dimethylimidazol-2-ylidene copper(I) hexamethyldisilazide was not successful as an ALD precursor. The fact that a copper-containing film was generated using water as a reactant gas suggests that the first five tests failed as a result of a lack of surface reactivity of the unsaturated compound monolayer with hydrogen.

Example 2

Synthesis of Mono-metallic Precursor Compounds with symmetrically substituted sNHC A. Synthesis of symmetrical sNHC-containing precursor compounds Targeted symmetrically substituted precursor compounds 1a, 2a and 3a, were synthesized using a process comprising salt metathesis. Details of the synthetic steps, from the diamine starting materials are provided below.

Materials and Methods

All manipulations involving a copper-containing reagent or product were performed in an MBraun Labmaster™ 130 Dry box (mBraun, Stratham, N.H., U.S.A.) under a nitrogen atmosphere. NMR spectra were recorded on a 400 MHz Bruker AMX spectrometer. NMR spectra that were measured in $CDCl_3$ were referenced against TMS. NMR spectra measured in $C_6D_6$ or DMSO-$d_6$ were referenced against residual protonated solvent. N,N'-ditertbutyl-ethylenediamine, N,N'-diisopropyl-ethylenediamine, and N,N'-diethyl-ethylenediamine, triethyl orthoformate were purchased from Alfa Aesar (VWR, Mississauga, Ontario, Canada). Sodium tert-butoxide, copper(I) chloride, formic acid were purchased from Sigma Aldrich Inc. (Oakville, Ontario, Canada). Hydrochloric acid (11.6 M) was obtained from Anachemia Canada Inc. (Montreal, Quebec, Canada) and was diluted as necessary. The diethyl ether adduct of lithium hexamethyldisilazide was prepared according to Lappert et al. JACS 1983, 105, 302.

Acetone, diethyl ether, and toluene were purchased from Calcdon Laboratories Ltd. (Georgetown, Ontario, Canada) as reagent grade. Diethyl ether and toluene were purified from an MBraun Solvent Purifier System, and stored over 3A molecular sieves Anhydrous tetrahydrofuran and anhydrous pentane were purchased from Sigma Aldrich Inc. (Oakville, Ontario, Canada) and used as received.

Synthesis of N,N'-dialkyl ethylenediamines

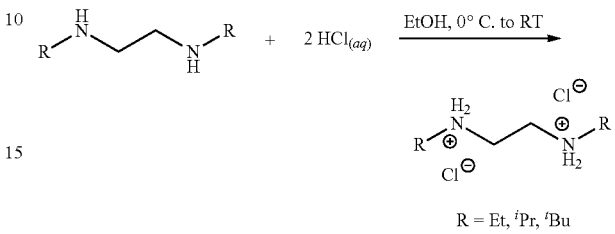

N,N'-diethyl-ethylenediamine dihydrochloride: N,N'-diethyl-ethylenediamine (4.71 g, 40.5 mmol) was dissolved in 60 ml of ethanol and cooled in an ice bath. Seven millilitres of 11.6 M $HCl_{(aq)}$ was diluted to 20 mL with ethanol and added dropwise to a stirring solution of the diamine in ethanol. After the addition of $HCl_{(aq)}$, the solution was removed from the ice bath and stirred for 30 minutes while warming to room temperature ("RT"). Volatiles were evaporated under a flow of air leaving a colourless solid. This solid was washed with acetone and then with diethyl ether and dried in air to afford a quantitative yield. $^1$H NMR (DMSO-$d_6$): δ 9.44 (s, 4H), δ 3.25 (sept, 4H), δ 2.97 (q, 4H), δ 1.22 (t, 6H).

N,N'-diisopropylethylenediamine dihydrochloride: The same general procedure used to synthesize N,N'-diethyl-ethylenediamine dihydrochloride was used to synthesize N,N'-diisopropylethylenediamine dihydrochloride.

N,N'-diisopropylethylenediamine (13.32 g, 92.3 mmol) was dissolved in 100 ml of ethanol. Next, 31.2 mL of 6 M $HCl_{(aq)}$ was added dropwise to a stirring solution of the diamine in ethanol. The resulting solid was obtained, washed with acetone and dried in an oven at 90° C. (19.67 g, 98%). $^1$H NMR (DMSO-$d_6$): δ 9.46 (s, 4H), δ 3.35 (s, 4H), δ 3.28 (sept, 2H), δ 1.26 (d, 12H).

N,N'-ditertbutyl-ethylenediamine dihydrochloride: The same general procedure detailed above for synthesizing N,N'-diethyl-ethylenediamine dihydrochloride was used to synthesize N,N'-ditertbutyl-ethylenediamine dihydrochloride.

N,N'-ditertbutyl-ethylenediamine (7.026 g, 40.78 mmol) was dissolved in 100 ml of ethanol. Next, 30 mL of 3 M $HCl_{(aq)}$ was added dropwise a stirring solution of the diamine in ethanol. Volatiles were evaporated under a flow of air leaving a colourless solid. The yield was quantitative. The NMR data of the isolated solid matched with the literature reference in Artensen et al. Tetrahedron 2005, 61, 9710.

Synthesis of 1,3-dialkyl-4,5-dihydro-imidazolium chloride salts

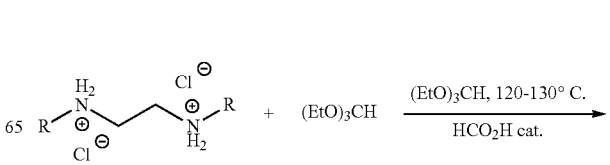

-continued

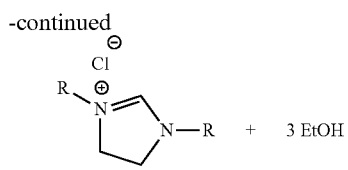

R = Et, $^i$Pr, $^t$Bu 1,3-Diethyl-4,5-dihydro-3H-imidazol-1-ium chloride: N,N'-diethyl-ethylenediamine dihydrochloride (7.67 g, 40.6 mmol) was suspended in 80 mL of triethyl orthoformate. 12 drops of formic acid were added and the suspension was refluxed with stirring at 130° C. for 24 hours. During reflux the suspension dissolved to give a clear solution. The solution was cooled to RT and the volatiles were removed in vacuo to afford a discoloured solid. The solid was dissolved in a minimum of acetone and 200 mL of diethylether ("Et$_2$O") was added to precipitate a solid. The solid was collected by filtration, washed with Et$_2$O, and dried under vacuum to afford 5.31 g, 80% yield, of a hygroscopic solid. $^1$H NMR (CDCl$_3$): δ 10.05 (s, 1H), δ 4.05 (s, 4H), δ 3.71 (q, 4H), δ 1.36 (t, 6H). $^{13}$C NMR (CDCl$_3$): δ 158.04, δ 47.82, δ 43.07, δ 12.98.

1,3-Diisopropyl-4,5-dihydro-3H-imidazol-1-ium chloride: The same general procedure used to synthesize 1,3-Diethyl-4,5-dihydro-3H-imidazol-1-ium chloride, except N,N'-diisopropylethylenediamine dihydrochloride (19.67 g, 90.5 mmol) was suspended in 180 mL of triethyl orthoformate and 20 drops of formic acid were added before reflux of the resulting suspension. Following removal of the volatiles from the reaction mixture, the product was dissolved in 50 mL of acetone and precipitated by addition of 200 mL of Et$_2$O (15 g, 88% yield). $^1$H NMR (CDCl$_3$): δ 10.16 (s, 1H), δ 4.33 (sept, 2H), δ 3.96 (s, 4H), δ 1.37 (d, 12H). $^{13}$C NMR (CDCl$_3$): δ 162.63, δ 50.05, δ 38.46, δ 21.76.

1,3-Ditertbutyl-4,5-dihydro-3H-imidazol-1-ium chloride: The same general procedure used to synthesize 1,3-Diethyl-4,5-dihydro-3H-imidazol-1-ium chloride was used to syntheszie 1,3-Ditertbutyl-4,5-dihydro-3H-imidazol-1-ium chloride, except N,N'-ditertbutyl-ethylenediamine dihydrochloride (5.00 g, 20.39 mmol) was suspended in 40 mL of triethyl orthoformate and 10 drops of formic acid were added before reflux of the resulting suspension. Reflux was maintained for 72 h. Volatiles were removed in vacuo to afford a discoloured solid (4.20 g, 94.2%). $^1$H NMR (DMSO-d$_6$): δ 8.19 (s, 1H), δ 3.93 (s, 4H), δ 1.36 (s, 18H). $^{13}$C NMR (CDCl$_3$): δ 154.20, δ 57.11, δ 45.22, δ 28.15.

Synthesis of 1,3-dialkyl-imidazolin-2-ylidene copper chloride salts

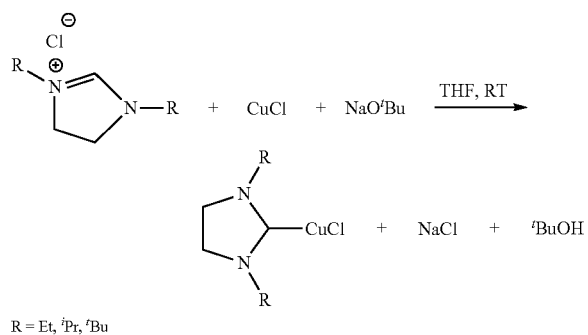

R = Et, $^i$Pr, $^t$Bu 1,3-diethyl-imidazolin-2-ylidene copper chloride: 1,3-Diethyl-4,5-dihydro-3H-imidazol-1-ium chloride (2.875 g, 17.7 mmol) was suspended in 50 mL of tetrahydrofuran ("THF"). CuCl (1.804 g, 18.2 mmol) was added and the resulting cloudy solution was stirred for 30 minutes. Sodium tert-butoxide (1.751 g, 18.2 mmol) was dissolved in 20 mL of THF and added dropwise to the stirring solution. Stirring was continued overnight. The cloudy solution was filtered through Celite™ to remove the NaCl precipitate. Volatiles of the clear filtrate were removed in vacuo until a light brown solid remained. The crude product was of sufficient purity to proceed without purification (3.78 g, 95.0%). $^1$H NMR (CDCl$_3$): δ 3.61 (q, 4H), δ 3.60 (s, 4H), δ 1.23 (t, 6H). $^{13}$C NMR (CDCl$_3$): δ 198.81, δ 47.93, δ 45.33, δ 14.10.

1,3-diisopropyl-4,5-dihydro-imidazolin-2-ylidene copper chloride: The same general procedure as above was used. 1,3-Diisopropyl-4,5-dihydro-3H-imidazol-1-ium chloride (4.404 g, 23.1 mmol) was suspended in 100 mL THF. CuCl (2.20, 22.2 mmol) and sodium tert-butoxide (2.260 g, 23.5 mmol) in 45 mL of THF were used. The solid was washed with pentane until the washings were colourless and then dried under vacuum (4.989 g, 88.3%). $^1$H NMR (CDCl$_3$): δ 4.39 (sept, 2H), δ 3.51 (s, 4H), δ 1.24 (d, 12H). $^{13}$C NMR (CDCl$_3$): δ 197.42, δ 51.80, δ 42.78, δ 21.15.

1,3-ditertbutyl-4,5-dihydro-imidazolin-2-ylidene copper chloride: 1,3-Ditertbutyl-4,5-dihydro-3H-imidazol-1-ium chloride (1.745 g, 7.98 mmol) was suspended in 30 mL of THF. Sodium tert-butoxide (0.766 g, 7.97 mmol) was dissolved in 20 mL of THF and added dropwise to the suspension and stirred for 30 min. CuCl (0.789, 7.97 mmol) was added and stirring continued overnight. The cloudy solution was filtered through Celite™ to remove the NaCl precipitate. Volatiles of the clear filtrate were removed in vacuo to afford a slightly pink solid (2.195 g, 97.8%). $^1$H NMR (CDCl$_3$): δ 3.54 (s, 4H), δ 1.53 (s, 18H). $^{13}$C NMR (CDCl$_3$): δ 197.58, δ 55.12, δ 45.63, δ 30.80.

Synthesis of 1,3-dialkyl-imidazolin-2-ylidene copper hexamethyldisilazide

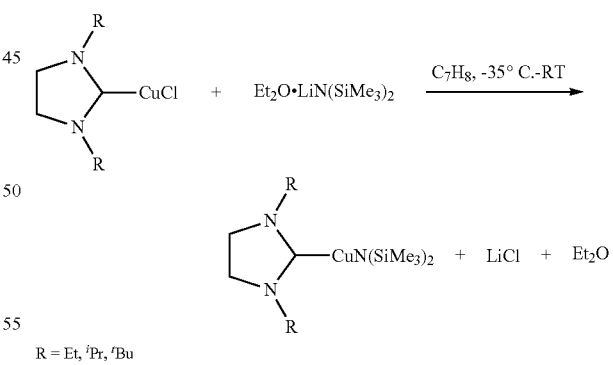

R = Et, $^i$Pr, $^t$Bu 1,3-diethyl-imidazolin-2-ylidene copper hexamethyldisilazide (1a): 1,3-diethyl-4,5-dihydro-imidazolin-2-ylidene copper chloride (0.938 g, 4.15 mmol) was dissolved in 40 mL of toluene in a flask. The flask was wrapped in aluminum foil and then cooled to −35° C. in a freezer. The diethyl ether adduct of lithium hexamethyldisilazide (1.006 g, 4.17 mmol) was dissolved in 20 mL of toluene and added dropwise to the −35° C. solution as it gradually warmed to room temperature. Stirring was continued overnight. The cloudy solution was filtered and then volatiles were removed from the clear filtrate under reduced pressure to afford a slightly discoloured liquid. This liquid was purified by distillation from 130 to 150° C. at 40 mtorr to obtain 1.287 g, 88%, of a colourless liquid. $^1$H NMR(C$_6$D$_6$): δ 3.23 (q, 4H), δ 2.37 (s, 4H), δ 0.76 (t, 6H), δ 0.58 (s, 18H). $^{13}$C NMR(C$_6$D$_6$): δ 201.26, δ 47.11, δ 44.81, δ 13.83, δ 7.22.

1,3-diisopropyl-imidazolin-2-ylidene copper hexamethyldisilazide (2a): The same reaction as above was used substituting 1,3-diisopropyl-4,5-dihydro-imidazolin-2-ylidene copper chloride (4.456 g, 17.52 mmol) dissolved in 130 mL of toluene and the diethyl ether adduct of lithium hexamethyldisilazide (4.248 g, 17.6 mmol) dissolved in 70 mL of toluene. Volatiles were removed to afford a solid which was purified by sublimation at 90° C. and 35 mtorr using a dry ice/acetone cold finger (6.322 g, 95%). $^1$H NMR(C$_6$D$_6$): δ 4.48 (sept, 2H), δ 2.48 (s, 4H), δ 0.80 (d, 12H), δ 0.57 (s, 18H). $^{13}$C NMR(C$_6$D$_6$): δ 200.39, δ 51.15, δ 41.86, δ 20.67, δ 7.21.

1,3-ditertbutyl-imidazolin-2-ylidene copper hexamethyldisilazide (3a):

The same reaction as above was used substituting 1,3-ditertbutyl-4,5-dihydro-imidazolin-2-ylidene copper chloride (0.489 g, 1.74 mmol) dissolved in 30 mL of toluene and the diethyl ether adduct of lithium hexamethyldisilazide (0.420 g, 1.74 mmol) dissolved in 10 mL of toluene. Volatiles were removed in vacuo to afford an off-white solid which was redissolved in 3 mL of pentane and held at −35° C. for 24 hours. The solution was decanted to afford colourless needle crystals (0.610 g, 86.4%). $^1$H NMR(C$_6$D$_6$): δ 2.56 (s, 4H), δ 1.32 (s, 18H), δ 0.56 (s, 18H). $^{13}$C NMR (C$_6$D$_6$): δ 201.50, δ 55.04, δ 45.24, δ 30.78, δ 6.87.

B: Modified Synthesis of sNHC-containing Precursor Compounds

The following procedure details a modified synthesis of the sNHC-containing precursor compounds. This process removes an additional isolation step (of the intermediate dialkylamine dihydrochloride) in making the starting 1,3-dialkyl-imidazolium salt prior to the addition of NaN(TMS)$_2$.

Step 1: Preparation of 1,3-dialkyl-imidazolium salts

In comparison to the procedure detailed above in Example 2, this procedure reduces the number of isolation steps by one (4 steps in the above synthesis; 3 in this sequence), and was found to improve upon the yield of the alkyl-imidazolium salt, 1,3-diisopropyl-4,5-dihydro-3H-imidazol-1-ium chloride (i.e., from about 78% to about 93%).

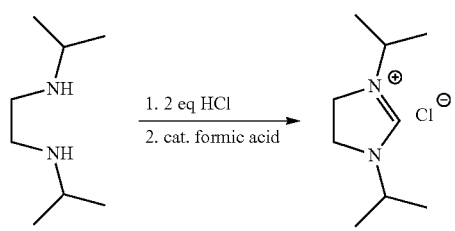

To a nitrogen purged flask was added 2.299 g (15.94 mmol) of N,N'-diisopropylethylenediamine, which was diluted in 35 mL of trimethyl orthoformate. The solution was cooled to 0° C. before 8 mL of HCl (4.0 M in 1,4-dioxane, 32.0 mmol) was added dropwise, resulting in a thick white slurry. Once the addition of HCl was finished the solution was gradually warmed to room temperature and stirred vigorously for 2 hours. After this time, 3 drops of formic acid were added to the suspension. A condenser was attached to the reaction flask, and the suspension was heated to 100° C. for a period of 16 hours. The slurry gradually dissolved in heated trimethyl orthoformate, resulting in a clear orange solution. After the 16 hour reaction period, the solution was cooled to room temperature.

To isolate the product, 150 mL of heptanes were added to the orange solution, causing a dark orange oil to separate from the solution. The top portion was decanted to isolate the orange oil. In order to precipitate the product from the oil, 30 mL of toluene was added and the mixture was concentrated under vacuum. Approximately 5 mL were removed before a solid material precipitated from solution. The remaining solvent was then decanted and the solid dried under vacuum, yielding 2.829 g (14.83 mmol, 93%), of the product, 1,3-diisopropyl-4,5-dihydro-3H-imidazol-1-ium chloride.

Step 2: Preparation of 1,3-dialkyl-imidazolin-2-ylidene copper chloride salts

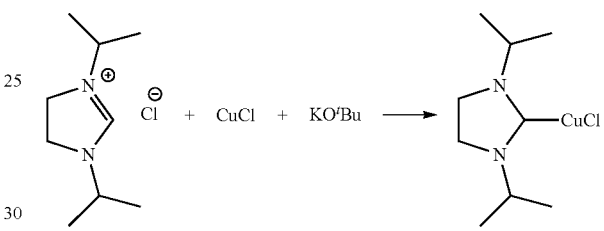

Under an inert atmosphere, 0.6613 g (3.47 mmol) of 1,3-diisopropyl-4,5-dihydro-3H-imidazol-1-ium chloride were added to a 250 mL round bottomed flask. To the same flask was added 0.378 g (3.81 mmol) of CuCl. The reagents were suspended in 50 mL of tetrahydrofuran and cooled to 0° C. A KO$^t$Bu solution (0.428 g, 3.81 mmol in 20 mL of THF) was added dropwise to the cooled solution of 1,3-diisopropyl-4,5-dihydro-3H-imidazol-1-ium chloride with CuCl, resulting in the formation of a green suspension. The suspension was kept cooled until the addition of base was completed. Once finished, the combined solution was gradually warmed to room temperature and stirred vigorously for 24 hours. The reaction was filtered over a layer of Celite to remove the insoluble material. The 1,3-diisopropyl-4,5-dihydro-imidazolin-2-ylidene copper chloride was then isolated by the addition of hexanes (approximately 2 volume equivalents of hexanes). The supernatant solution was decanted to isolate an off-white powder. The powder was pumped to dryness under vacuum to yield 0.705 g (2.77 mmol, 80%) of 1,3-diisopropyl-4,5-dihydro-imidazolin-2-ylidene copper chloride.

Step 3: Preparation of 1,3-dialkyl-imidazolin-2-ylidene copper hexamethyldisilazide

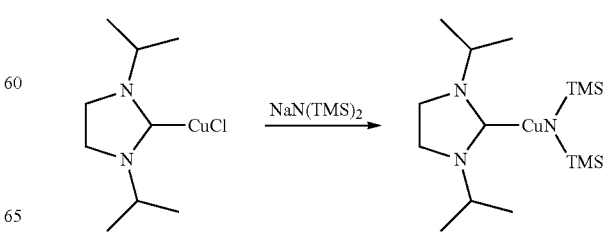

Under inert atmosphere, 9.0805 g (35.7 mmol) of 1,3-diisopropyl-4,5-dihydro-imidazolin-2-ylidene copper chloride was dissolved in 250 mL of dry toluene. In a separate flask, 6.55 g (35.7 mmol) of NaN(TMS)$_2$ were dissolved in 100 mL of dried toluene. The solution containing 1,3-diisopropyl-4,5-dihydro-imidazolin-2-ylidene copper chloride was cooled to 0° C. and then the amide solution was added dropwise over the course of one hour. The combined solution was gradually warmed to room temperature once the addition was completed, and the solution was stirred for 24 hours. The initially green coloured solution became a dark brown solution as the reaction proceeded. After 24 hours, the solution was filtered under inert atmosphere through a layer of Celite. The filtrate was clear and colourless, and collected in a nitrogen purged flask. The insoluble material was washed with 3×20 mL of toluene. The washings were combined with the filtrate. The solvent was removed from the combined washings and filtrate, yielding 11.3631 g (30 mmol, 84%) of product, 1,3-diisopropyl-imidazolin-2-ylidene copper hexamethyldisilazide (2a).

Example 3

Synthesis of Mono-metallic Precursor Compounds with Asymmetrically Substituted sNHC The targeted asymmetric carbene copper amide complexes 12a, 13a and 14a are depicted below,

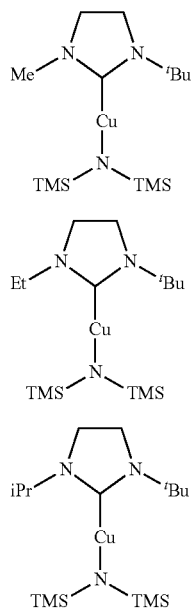

where TMS is a trimethylsilyl group. These compounds were prepared according to the procedure detailed below.

Materials and Methods

NMR spectra were recorded on a Varian 400-MR NMR spectrometer (Agilent, Mississauga, Ontario, Canada). All NMR spectra are referenced against residual protonated solvent. 2-(tert-butylamino)ethanol, methylamine, ethylamine, formic acid, and copper (I) chloride were obtained from Sigma Aldrich Inc. (Oakville, Ontario, Canada). Hydrochloric acid was obtained from Fisher Scientific (Ottawa, Ontario, Canada) and was diluted to 6M in water. Thionyl chloride, potassium tert-butoxide, and sodium bis(trimethylsilyl)amide were obtained from Alfa Aesar (VWR, Mississauga, Ontario, Canada).

Dichloromethane, acetone, and diethyl ether was obtained from Fisher Scientific. Anhydrous ethanol was obtained from Commercial Alcohols Inc (Brampton, Ontario, Canada). Tetrahydrofuran and toluene were obtained from EMD Chemicals (Gibbstown, N.J., USA) and purified using a VAC Solvent Purifier (Vacuum Atmospheres Company, Hawthorne, Calif., USA).

Synthesis of N-tert-butyl N'-alkyl ethylenediamines

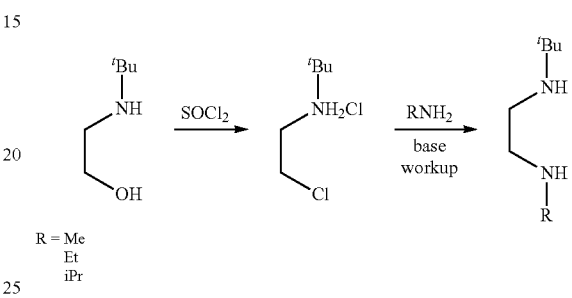

R = Me
Et
iPr

The diamines were synthesized according to a literature procedure (Morley, J. S. ICI LTD (1963) *Substituted Ethylenediamines*, GB919177 (A)) and characterized from data outlined by Denk. (Denk, M. K.; Hezarkhani, A.; Zheng, F. L. *Eur. J. Inorg. Chem.* 2007, 3527-3534). After isolation of the diammonium salts all manipulations were carried out under inert atmosphere (Nitrogen-99.99%, supplied by Air Liquide, Toronto, Ontario, Canada).

Synthesis of 1-tert-butyl-3-alkyl-imidazolium salts

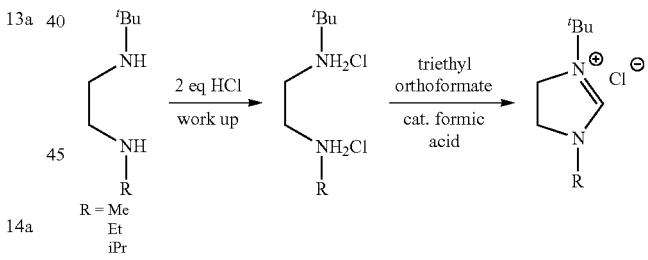

R = Me
Et
iPr

Asymmetric imidazolium salts have not been previously reported, however, a modified version of a literature procedure (Arentsen, K.; Caddick, S.; Cloke, G. N. *Tetrahedron*, 2005, 61, 9710-9715) was found to be useful in the synthesis of these intermediates (outlined in the scheme above).

3-(tert-butyl)-1-methyl-4,5-dihydro-imidazol-3-ium chloride: White solid, 25%. $^1$H NMR (CDCl$_3$): 10.26 ppm (s, 1H), 3.91 ppm (s, 4H), 3.45 ppm (s, 3H), 1.48 ppm (s, 9H).

3-(tert-butyl)-1-ethyl-4,5-dihydro-imidazol-3-ium chloride: White solid, 48%. $^1$H NMR (CDCl$_3$): 10.13 ppm (s, 1H), 3.89 ppm (s, 4H), 3.86 ppm (q, 2H), 1.30 ppm (s, 9H), 1.28 ppm (t, 3H). $^{13}$C NMR (CDCl$_3$): 157.2 ppm, 56.8 ppm, 47.4 ppm, 45.1 ppm, 43.2 ppm, 28.3 ppm, 13.1 ppm.

3-(tert-butyl)-1-isopropyl-4,5-dihydro-imidazol-3-ium chloride: White solid, 48%. $^1$H NMR (CDCl$_3$): 10.09 ppm (s, 1H), 4.73 ppm (m, 1H), 3.89 ppm (s, 4H), 1.33 ppm (s, 9H), 1.31 ppm (d, 6H).

Synthesis of 1-tert-butyl-3-alkyl-imidazolidin-2-ylidene copper (I) chloride compounds

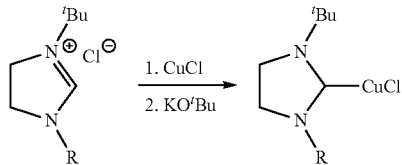

R = Me, Et, $^i$Pr 1-tert-Butyl-3-ethyl-imidazolidin-2-ylidene copper (I) chloride: 1.8816 g (9.87 mmol) of 3-tert-butyl-1-ethyl-4,5-dihydro-imidazol-3-ium chloride was combined with 0.9913 g (10.01 mmol) of CuCl in a 250 mL Schlenk flask, and dissolved in 100 mL of THF. In a separate flask was added 1.1106 g (9.90 mmol) of potassium tert-butoxide, which was dissolved in 50 mL of tetrahydrofuran. Each solution was stirred for 30 minutes before the potassium tert-butoxide solution was transferred dropwise via cannula to the CuCl/imidazolium chloride solution. The resultant mixture gradually became dark brown over the course of an hour. Mixing was continued at room temperature for 24 hours. The brown suspension was filtered through Celite™ over a medium porosity glass frit. The insoluble material was washed with 4×10 mL of THF. The washings were combined with the brown filtrate and the solvent was removed under vacuum, yielding a brown oil. A brown powder was isolated after diluting the oil in 20 mL of toluene followed by the addition of 30 mL of hexanes. The supernatant solution was decanted to yield 1.989 g (7.85 mmol, 80% yield) of 1-tent-Butyl-3-ethyl-imidazolidin-2-ylidene copper (I) chloride as a brown solid. $^1$H NMR($C_6D_6$): 3.25 ppm (q, 2H), 2.82 ppm (t, 3H), 2.63 ppm (t, 3H), 1.19 ppm (s, 9H), 0.77 ppm (t, 3H). $^{13}$C NMR($C_6D_6$): 198.5 ppm, 54.5 ppm, 46.7 ppm, 46.3 ppm, 41.7 ppm, 30.3 ppm, 13.9 ppm.

1-tert-Butyl-3-methyl-imidazolidin-2-ylidene copper (I) chloride: 1-tert-Butyl-3-methyl-imidazolidin-2-ylidene copper (I) chloride was synthesized from 3-(tert-butyl)-1-methyl-4,5-dihydro-imidazol-3-ium chloride using the same method as set out above for the 3-ethyl compound. The product was a white solid with a yield of 65.4%. $^1$H NMR($C_6D_6$): 3.65 ppm (t, 3H), 3.48 ppm (t, 3H), 3.26 ppm (s, 3H), 1.50 ppm (s, 9H). $^{13}$C NMR (CDCl$_3$): 198.7 ppm, 54.9 ppm, 50.3 ppm, 46.9 ppm, 38.8 ppm, 30.6 ppm.

1-tert-Butyl-3-isopropyl-imidazolidin-2-ylidene copper (I) chloride: 1-tert-Butyl-3-isopropyl-imidazolidin-2-ylidene copper (I) chloride was synthesized from 3-(tert-butyl)-1-isopropyl-4,5-dihydro-imidazol-3-ium chloride using the same method as set out above for 3-ethyl compound. The product was a white solid, with a yield of 92%. $^1$H NMR($C_6D_6$): 4.56 ppm (m, 1H), 3.59 ppm (t, 3H), 3.40 ppm (t, 3H), 1.46 ppm (s, 9H), 1.20 ppm (d, 6H).

Synthesis of bis(trimethylsilyl)amino-1-tert-butyl-3-alkyl-imidazolidin-2-ylidene copper (I)

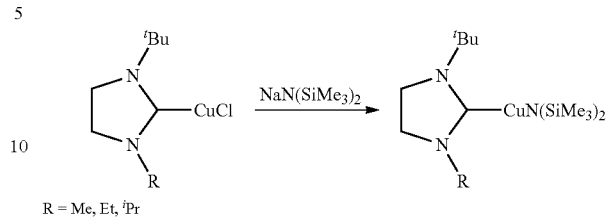

R = Me, Et, $^i$Pr 1-tert-butyl-3-ethyl-imidazolidin-2-ylidene copper (I) hexamethyldisilazide (13a): 0.906 g (3.58 mmol) of 1-tert-butyl-3-ethyl-imidazolidin-2-ylidene copper (I) chloride was dissolved in 60 mL of toluene and cooled to 0° C. In a separate flask was added 0.656 g (3.58 mmol) of sodium bis(trimethylsilyl)amide which was dissolved in 60 mL of toluene. The bis(trimethylsilyl)amide solution was added dropwise to the solution of the imidazolidin-2-ylidene copper chloride compound via cannula. The resultant mixture was gradually warmed to room temperature and stirred for 60 hours. The product suspension was filtered over a layer of Celite™ through a medium porosity glass frit. The insoluble fraction was washed with 3×15 mL of toluene. The washings were combined with the colourless filtrate, and the solvent was removed under vacuum affording 0.9513 g (2.52 mmol, 70.3% yield) of 13a as an amber oil. $^1$H NMR($C_6D_6$): 3.40 ppm (q, 2H), 2.54 ppm (t, 3H), 2.33 ppm (t, 3H), 1.21 ppm (s, 9H), 0.79 ppm (t, 3H), 0.56 ppm (s, 18H). $^{13}$C NMR($C_6D_6$): 201.0 ppm, 54.5 ppm, 46.3 ppm, 46.2 ppm, 45.9 ppm, 30.4 ppm, 13.8 ppm, 7.1 ppm.

1-tert-butyl-3-methyl-imidazolidin-2-ylidene copper (I) hexamethyldisilazide (12a): 1-tert-butyl-3-methyl-imidazolidin-2-ylidene copper (I) hexamethyldisilazide 12a was synthesized from 1-tert-Butyl-3-methyl-imidazolidin-2-ylidene copper (I) chloride using the same method as set out above for the synthesis of compound 13a. The reaction afforded 12a as a brown oil (44% yield). $^1$H NMR($C_6D_6$): 2.75 ppm (s, 3H), 2.53 ppm (t, 3H), 2.19 ppm (t, 3H), 1.20 ppm (s, 9H), 0.56 ppm (s, 18H). $^{13}$C NMR($C_6D_6$): 201.5 ppm, 54.5 ppm, 49.3 ppm, 46.2 ppm, 38.2 ppm, 30.4 ppm, 7.2 ppm.

1-tert-butyl-3-isopropyl-imidazolidin-2-ylidene copper (I) hexamethyldisilazide (14a)

1-tert-butyl-3-isopropyl-imidazolidin-2-ylidene copper (I) hexamethyldisilazide (14a) was synthesized from 1-tert-Butyl-3-isopropyl-imidazolidin-2-ylidene copper (I) chloride using the same method as set out above for the synthesis of compound 13a. The reaction afforded 14a as a colourless solid (86% yield). $^1$H NMR ($C_6D_6$): 4.78 ppm (m, 1H), 2.58 ppm (t, 3H), 2.42 ppm (t, 3H), 1.22 ppm (s, 9H), 0.81 ppm (d, 6H), 0.56 ppm (s, 18H). $^{13}$C NMR($C_6D_6$): 200.7 ppm, 54.5 ppm, 52.3 ppm, 45.3 ppm, 41.4 ppm, 30.3 ppm, 20.6 ppm, 7.1 ppm.

Example 4

X-Ray Structural Analysis of Metal Precursor Compounds

X-ray structural analysis was performed for compound 2c according to the following method.

Crystals of the compound were selected and mounted on plastic mesh using viscous oil flash-cooled to the data collection temperature. Data were collected on a Brüker-AXS APEX CCD diffractometer with graphite-monochromated Mo-Kα radiation (λ=0.71073 Å). Unit cell parameters were obtained from 60 data frames, 0.3° ω, from three different sections of Ewald sphere. The systematic absences in the data and the unit cell parameters were consistent to C2/c and Cc for 2c. In the non-unique systematic absence cases, the centrosymmetric space group option yielded chemically reasonable and computationally stable results of refinement. The data-sets were treated with SADABS absorption corrections based on redundant multiscan data (Sheldrick, G. M. 2008. Acta Cryst. A64, 112-122). The structure was solved using direct methods and refined with full-matrix, least-squares procedures on F2. The compound molecule is located on a two-fold rotation axis. All non-hydrogen atoms were refined with anisotropic displacement parameters. All hydrogen atoms were treated as idealized contributions. Atomic scattering factors are contained in the SHELXTL 6.12 program library (Sheldrick, G. M., 2008. Acta Cryst. A64, 112-122).

Figure 7:
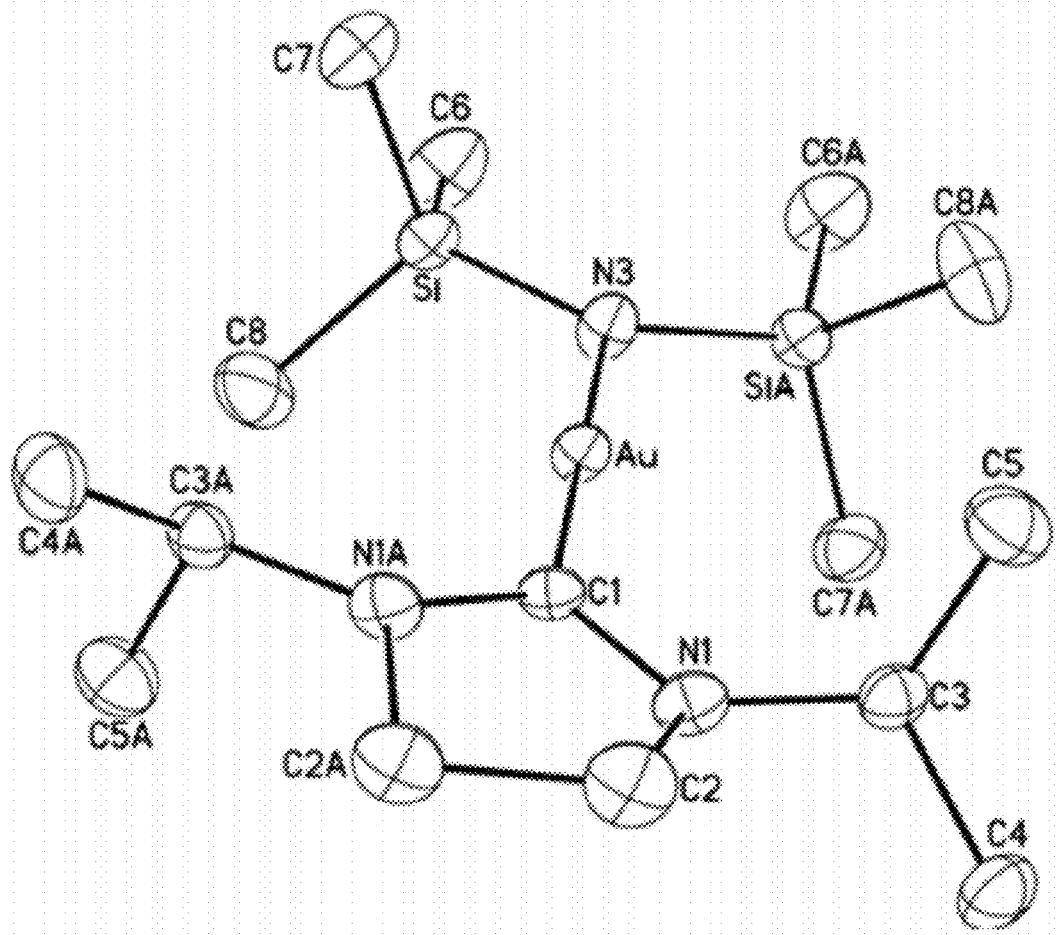
FIG. 7 is an ORTEP drawing of the X-ray crystal structure of 1,3-diisopropyl-imidazolin-2-ylidene gold hexamethyldisilazide (2c)

An ORTEP drawing of the X-ray structure is depicted in FIG. 7.

Example 5

Thermogravimetric Analysis of Metal Precursor Compounds

Vapour pressures of a variety of symmetrical and unsymmetrical copper precursor compounds were measured on a TA Instruments Q50 thermogravimetric (TG) analyser located in an MBraun Labmaster 130 Dry box under a nitrogen atmosphere. The TG was run in a stepped isotherm using the following sequence:
Ramp 40.00° C./min to 110.00° C.
Isothermal for 10.00 min
Ramp 40.00° C./min to 120.00° C.
Isothermal for 10.00 min
Ramp 40.00° C./min to 130.00° C.
Isothermal for 10.00 min
Ramp 40.00° C./min to 140.00° C.
Isothermal for 10.00 min
Ramp 40.00° C./min to 150.00° C.
Isothermal for 10.00 min
Ramp 40.00° C./min to 160.00° C.
Isothermal for 10.00 min
Ramp 40.00° C./min to 170.00° C.
Isothermal for 10 min
Ramp 40.00° C./min to 180.00° C.
Isothermal for 10 min
Ramp 40.00° C./min to 190.00° C.
Isothermal for 10.0 min
Ramp 40.00° C./min to 200.00° C.
Isothermal for 10.0 min
Ramp 10.00° C./min to 600.00° C.

The slope was determined for each isotherm interval, and if the data was linear for that interval, that was used as the "Δm/Δt" value for that temperature. The pressure was calculated using the Langmuir equation following the method of Umarji [G. V. Kunte, S. A. Shivashanker, A. M. Umarji Meas. Sci. Tech. 2008, 19, 025704] for estimation of vapour pressure. Benzoic acid was used as a standard to determine the a coefficient of the Langmuir equation (i.e., the Langmuir adsorption constant), and copper bis(2,2,6,6-tetramethyl-3,5-heptadionate) ("Cu(tmhd)$_2$") was used as a benchmark to demonstrate the method's validity.

Figure 8:
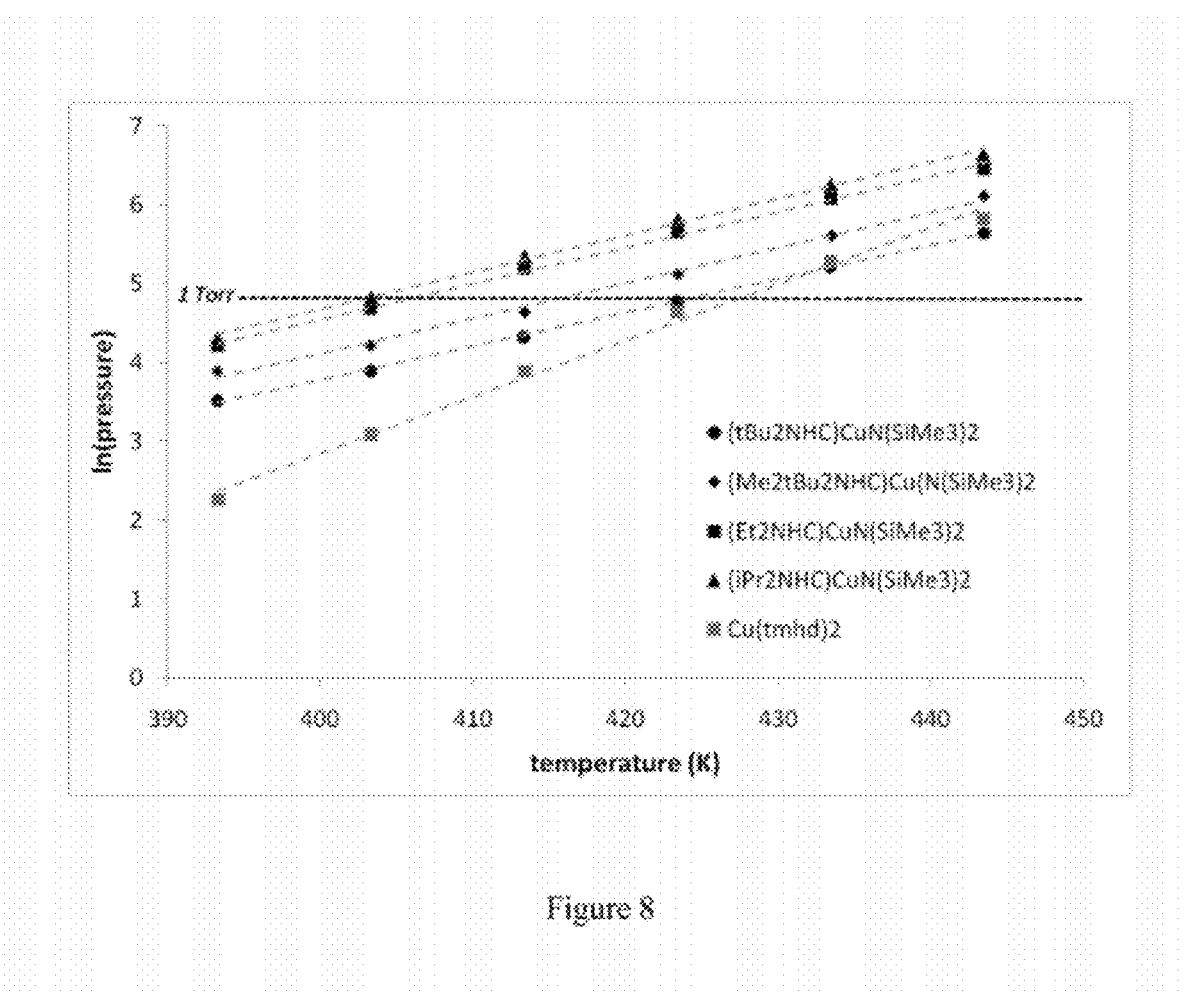
FIG. 8 is a graph of vapour pressure plots for four symmetrical copper precursor compounds in comparison to a control (copper bis-(2,2,6,6-tetramethyl-3,5-heptadionate)
Figure 9:
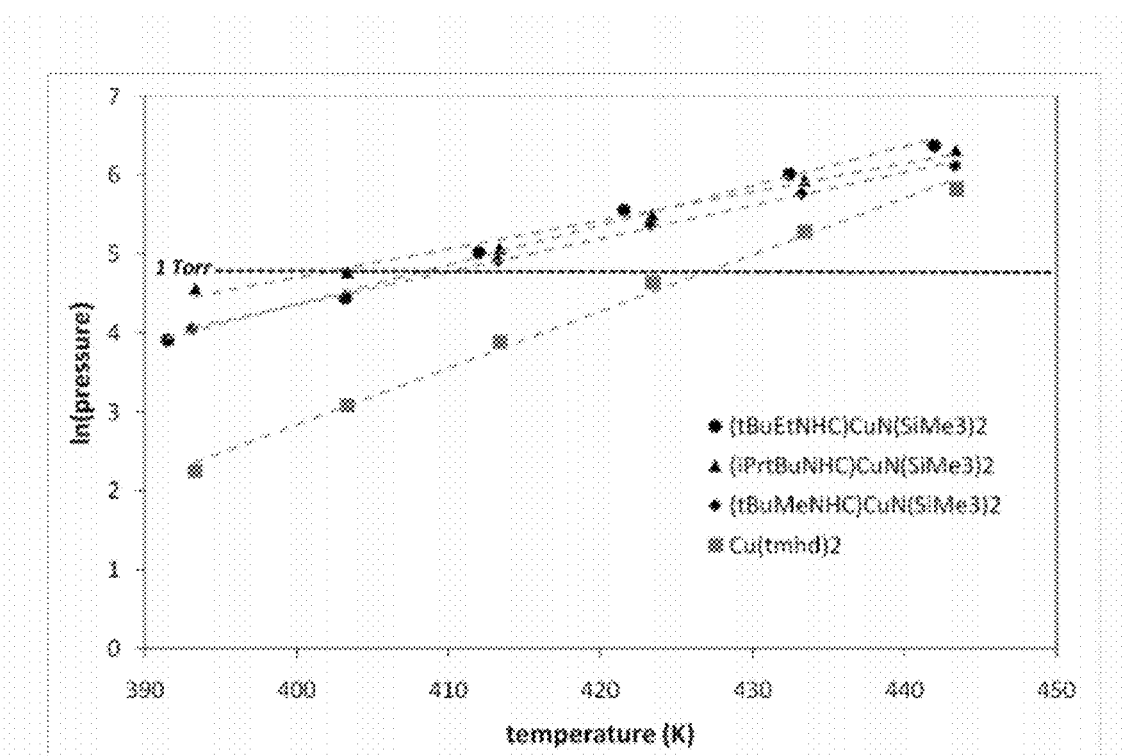
FIG. 9 is a graph of vapour pressure plots for three asymmetrical copper precursor compounds in comparison to a control (copper bis-(2,2,6,6-tetramethyl-3,5-heptadionate)

The results from vapour testing of four symmetrical copper precursor compounds and three unsymmetrical copper precursor compound are provided in the Table 1 and depicted in FIGS. 8 and 9. The compound, Cu(tmhd)$_2$, was used as a control as it is a known CVD precursor. The structure of Cu(tmhd)$_2$ is shown below:

TABLE 1

Vapour Testing of Symmetrical and Unsymmetrical Copper Precursor Compounds

| Compound | Temperature (° C.) for 1 Torr of Pressure |
|---|---|
| Cu(tmhd)$_2$ | 155 |
| Et$_2$-sNHC—Cu(I)—N(SiMe$_3$)$_2$ (1a) | 134 |
| $^i$Pr$_2$-sNHC—Cu(I)—N(SiMe$_3$)$_2$ (2a) | 131 |
| $^t$Bu$_2$-sNHC—Cu(I)—N(SiMe$_3$)$_2$ (3a) | 153 |
| Me$_2$$^t$Bu-sNHC—Cu(I)—N(SiMe$_3$)$_2$ (4a) | 144 |
| Me$^t$Bu-sNHC—Cu(I)—N(SiMe$_3$)$_2$ (12a) | 140 |
| Et$^t$Bu-sNHC—Cu(I)—N(SiMe$_3$)$_2$ (13a) | 137 |
| $^i$Pr$^t$Bu-sNHC—Cu(I)—N(SiMe$_3$)$_2$ (14a) | 132 |

In similar studies performed using similar copper-containing compounds that include an unsaturated NHC, the present inventors found that the unsaturated NHC compounds tested decomposed during the most basic thermogravimetric analysis (i.e., as temperature was increased 10° C. per minute up to 400° C.).

In contrast, the results provided herein, demonstrate good thermal stability and volatility for the copper precursor compounds that include the sNHC. In addition, the copper precursor compounds tested were found to have vapour pressure properties superior to those of Cu(tmhd)$_2$. First, the slopes of the vapour pressure lines are more shallow for the copper precursor compounds described herein than for Cu(tmhd)$_2$, which indicates that these compounds have higher vapour pressures at lower temperatures than Cu(tmhd)$_2$. Furthermore, all of the sNHC precursor compounds tested volatised to 1 Torr of pressure at a lower temperature than did Cu(tmhd)$_2$. These characteristics are desirable for successful ALD precursors.

Example 6

Thermogravimetric Analysis of Compounds Containing Saturated and Unsaturated N-heterocyclic Diaminocarbene Moieties TG analysis was performed on a TA Instruments Q50 thermogravimetric (TG) analyser located in an MBraun Labmaster 130 Dry box under a nitrogen atmosphere (99.999% at a flow rate of 100 mL/min). During testing the furnace was heated at 10° C./min from 30 to 600° C. Samples of the compounds to be studied were provided in platinum pans with diameters of 1 cm. The mass of each sample tested was within the range of from about 10 to about 30 mg. The mass ("weight") of the sample was obtained as the temperature was increased and plotted.

The results are provided in FIGS. 10-21. The residual mass (% mass that remains in the platinum pan after 600° C.) is displayed in bottom right corner of each graph.

Figure 10:
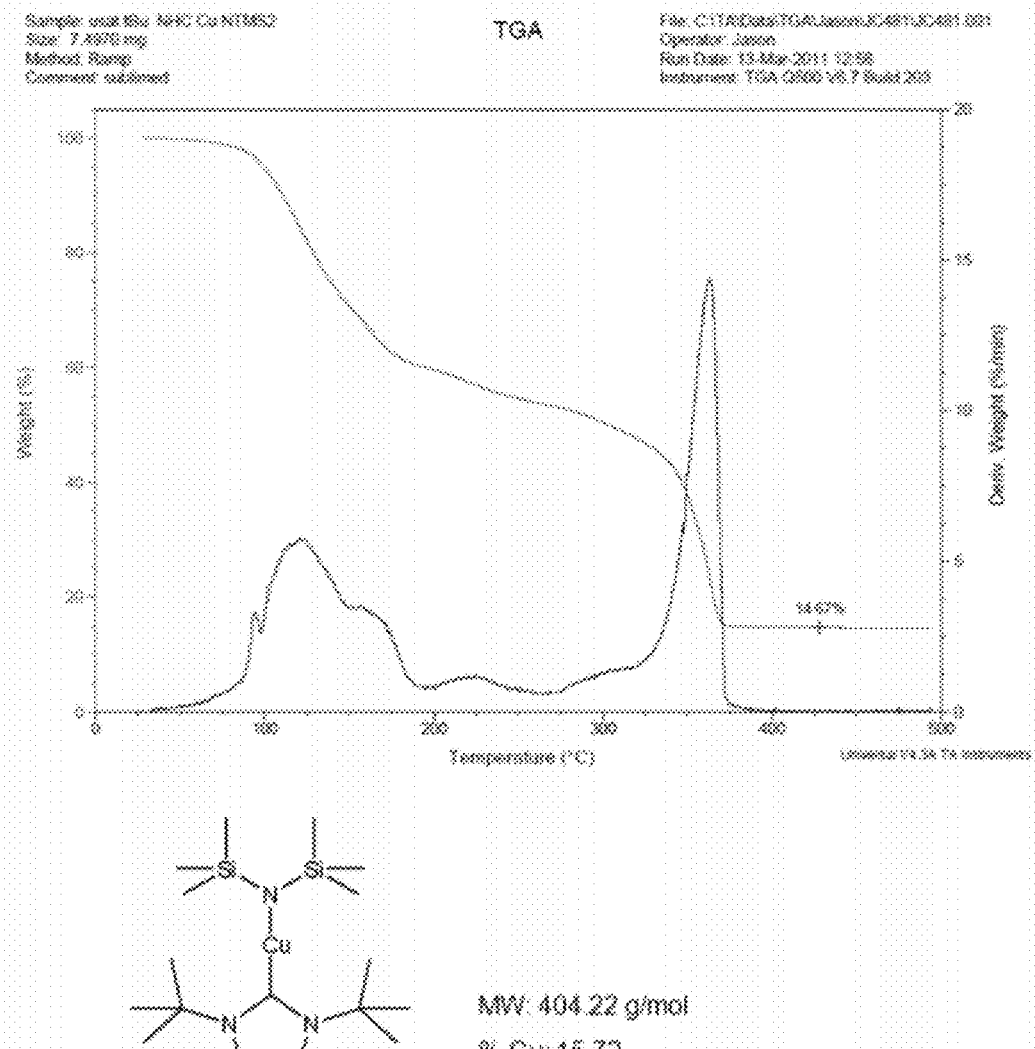
FIG. 10 is a weight loss curve for an unsaturated N-heterocyclic diaminocarbene-containing copper compound (1,3-di-tert-butyl-imidazol-2-ylidene copper hexamethyldisilazide)

FIG. 10 shows a weight loss curve for an unsaturated N-heterocyclic diaminocarbene-containing copper compound (1,3-di-tert-butyl-imidazol-2-ylidene copper hexamethyldisilazide). It is clear that this compound is thermally unstable since there are two weight loss events and a high residual mass of 14.7%, which indicate decomposition.

Figure 11:
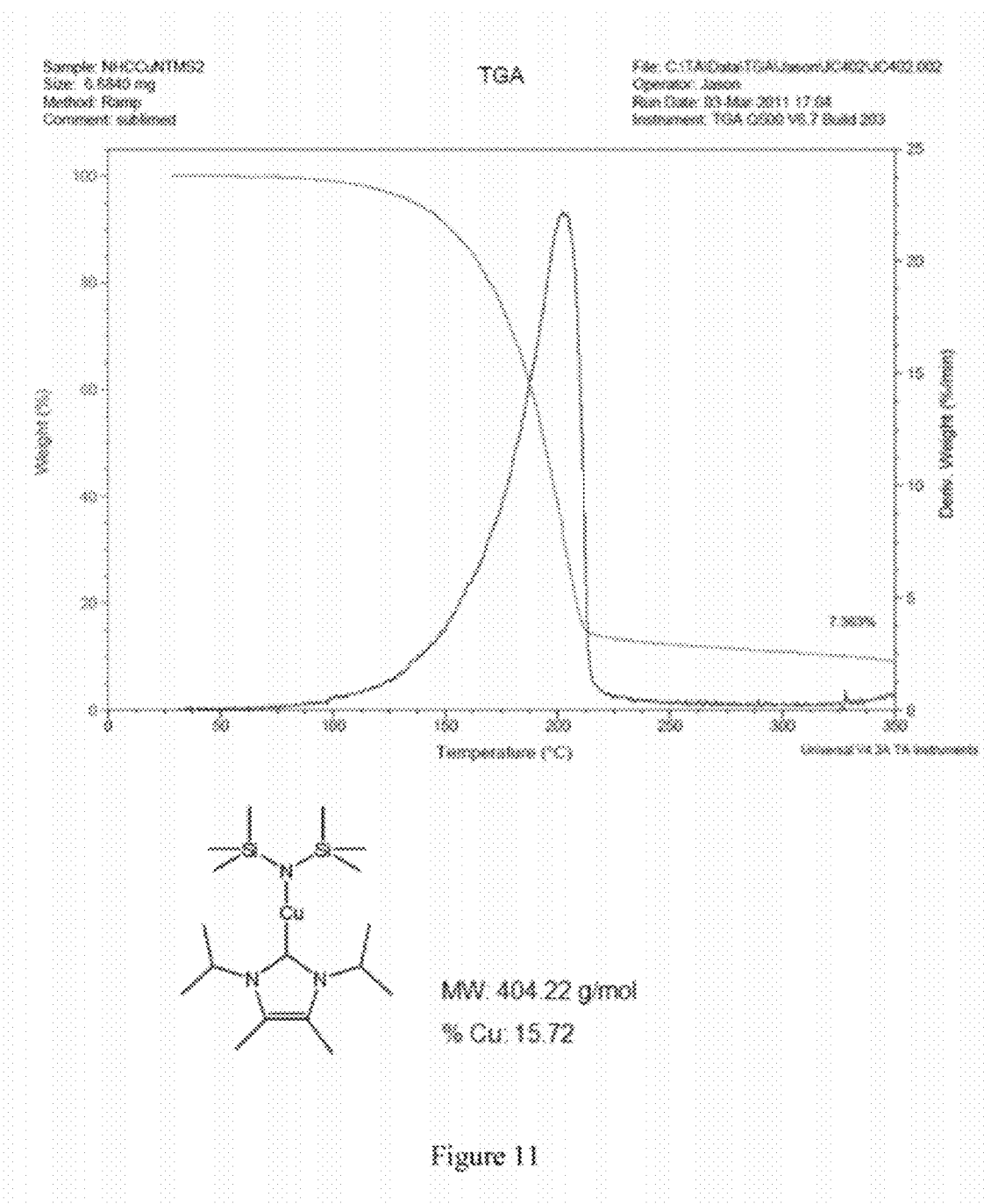
FIG. 11 is a weight loss curve for an unsaturated N-heterocyclic diaminocarbene-containing copper compound (1,3-diisopropyl-4,5-dimethyl-imidazol-2-ylidene copper hexamethyldisilazide)
Figure 12:
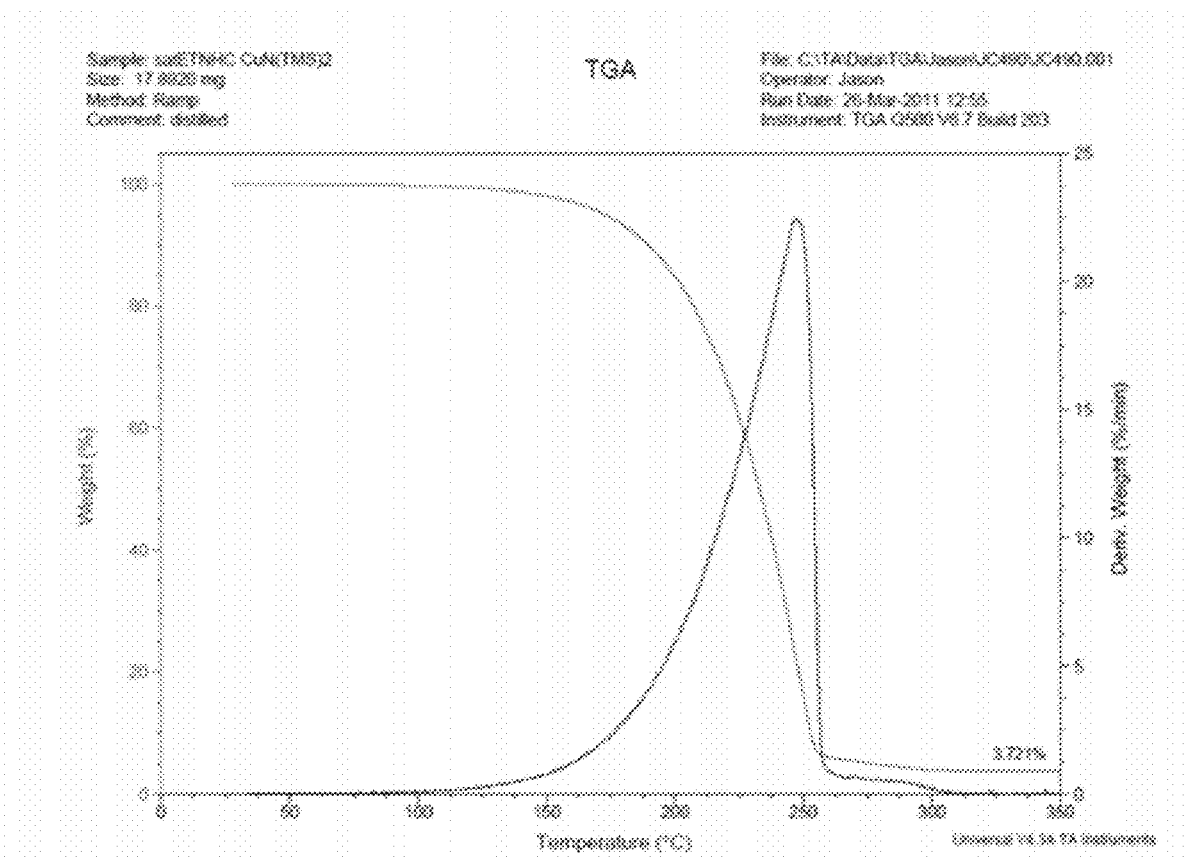
FIG. 12 is a weight loss curve for 1,3-diethyl-imidazolin-2-ylidene copper hexamethyldisilazide (1a)
Figure 12:
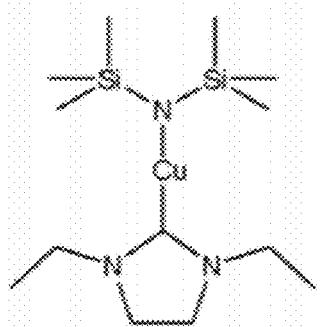

FIG. 11 shows an improvement of volatility and thermal stability of an unsaturated N-heterocyclic diaminocarbene-containing copper compound (1,3-diisopropyl-4,5-dimethyl-imidazol-2-ylidene copper hexamethyldisilazide; the compound of Formula III). This was achieved by chemically modifying the unsaturated bond with methyl groups. The residual mass was 7.4% which again indicates decomposition of the compound. This suggests that this compound will not be useful in ALD. The data obtained using the two unsaturated compounds suggested that the unsaturated bond is undesirable in an ALD precursor.

FIGS. 12-21 show weight loss curves for various sNHC-containing copper compounds.

Figure 14:
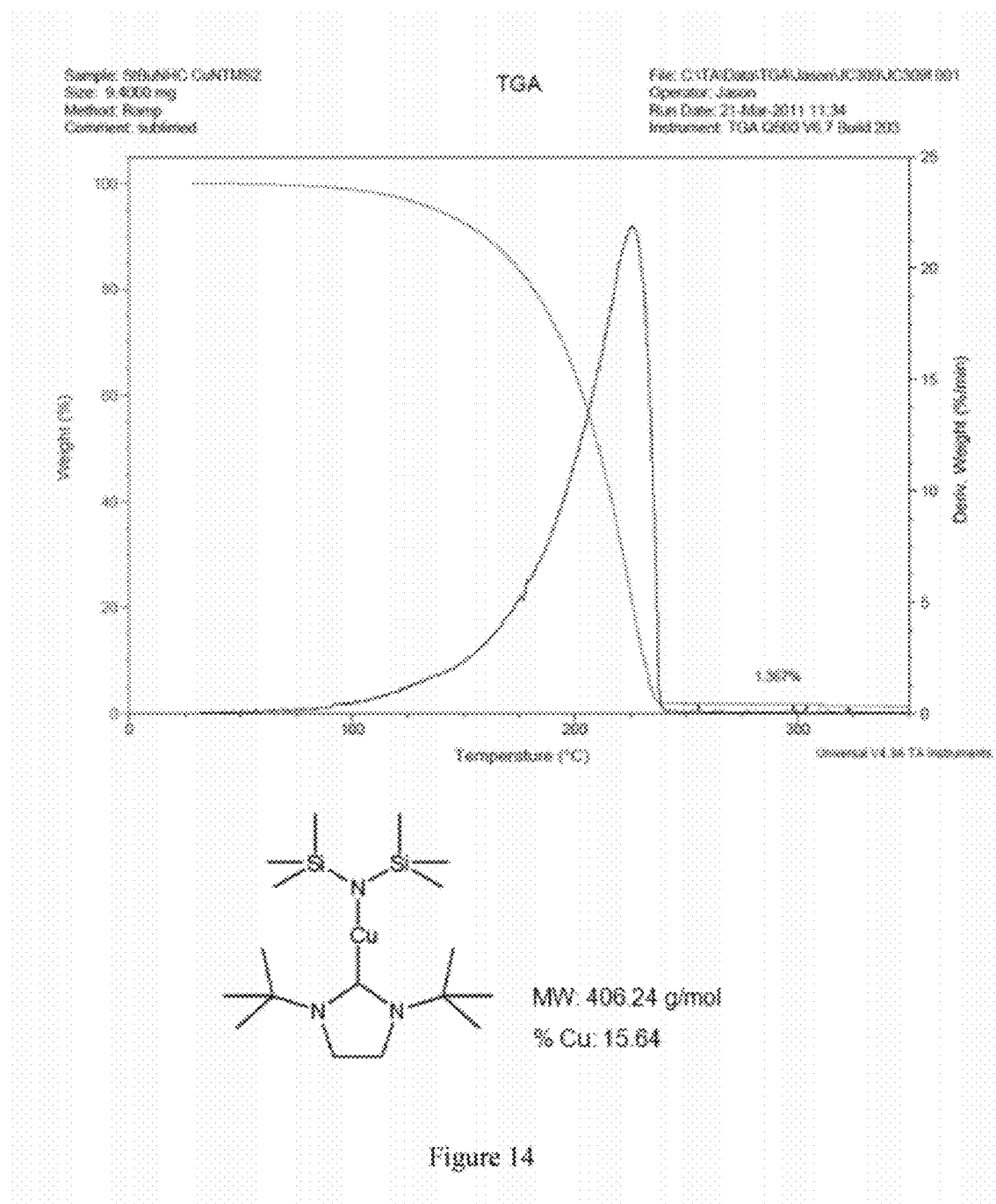
FIG. 14 is a weight loss curve for 1,3-di-tert-butyl-imidazolin-2-ylidene copper hexamethyldisilazide (3a)
Figure 15:
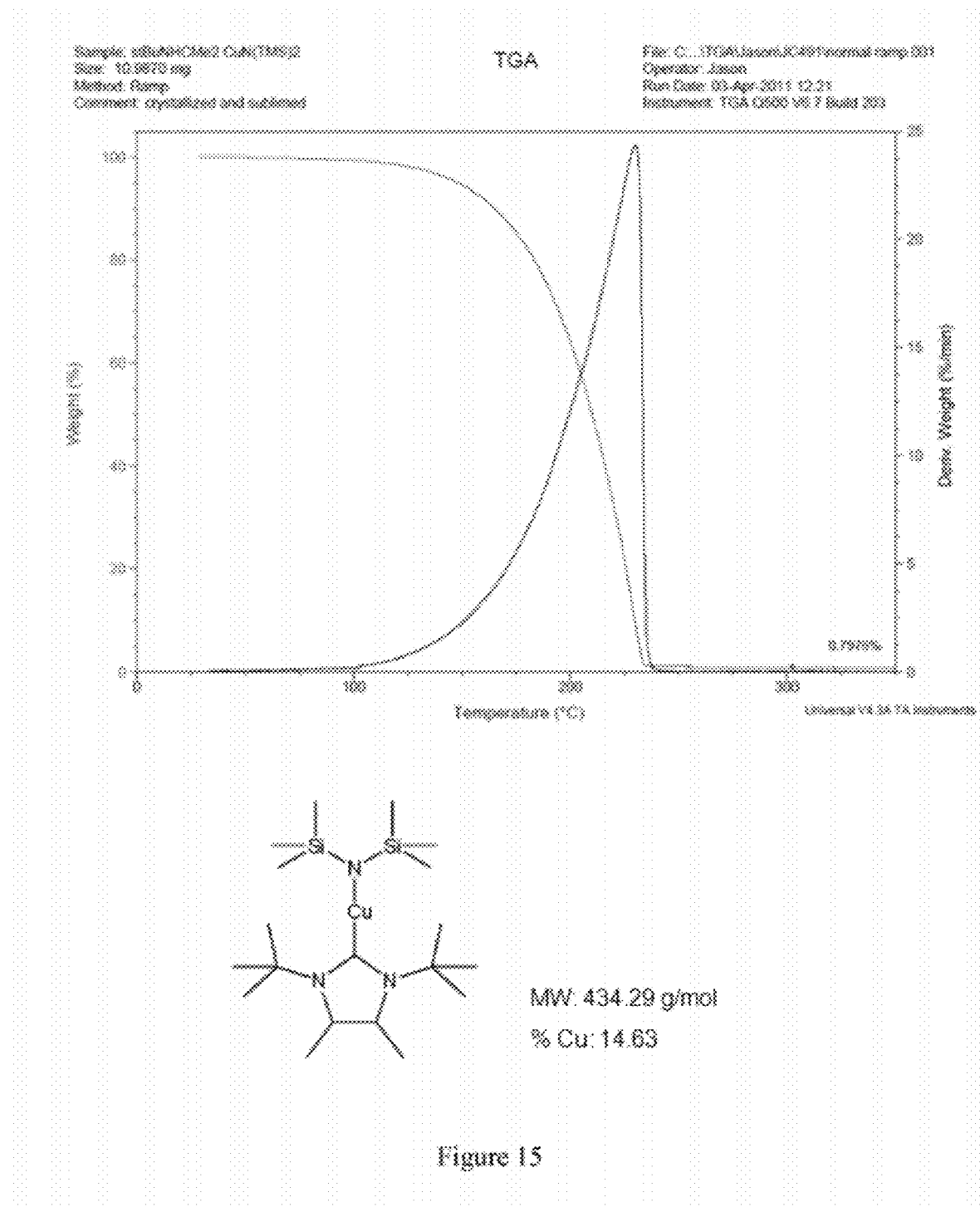
FIG. 15 is a weight loss curve for 1,3-di-tert-butyl-4,5-dimethyl-imidazolin-2-ylidene copper hexamethyldisilazide (4a)
Figure 16:
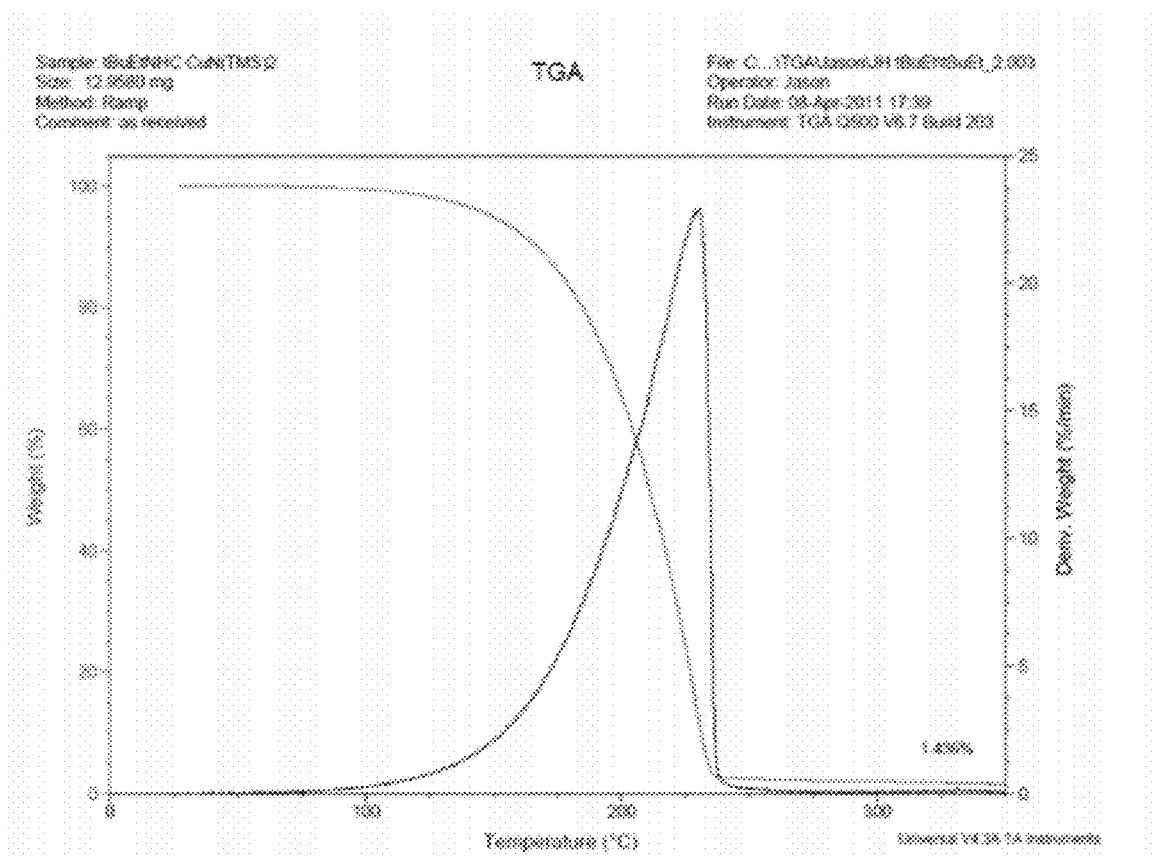
FIG. 16 is a weight loss curve for 1-tert-butyl-3-ethyl-imidazolin-2-ylidene copper hexamethyldisilazide (13a)
Figure 16:
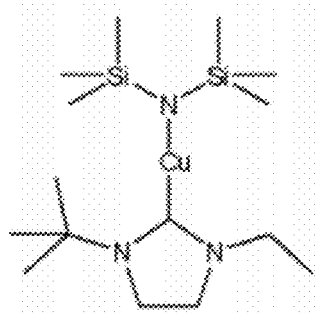
Figure 17:
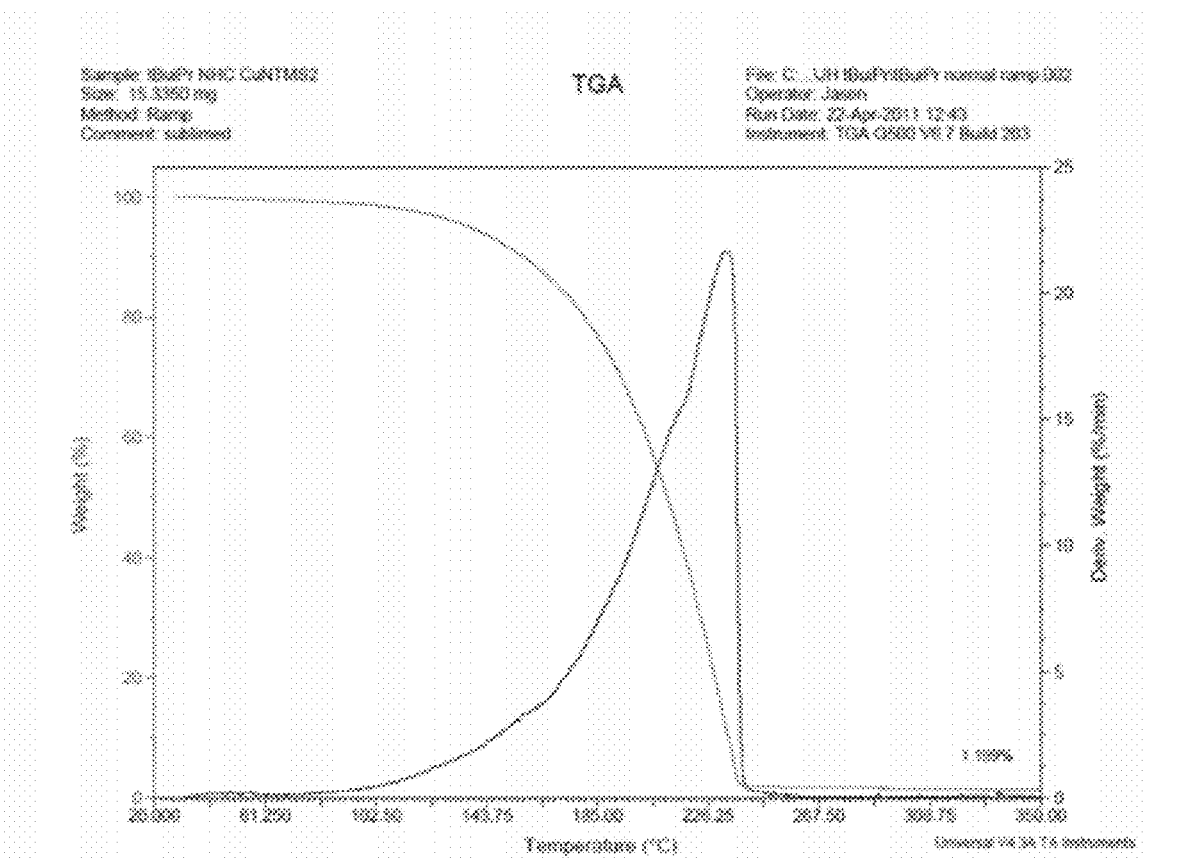
FIG. 17 is a weight loss curve for 1-tert-butyl-3-isopropyl-imidazolin-2-ylidene copper hexamethyldisilazide (14a)
Figure 17:
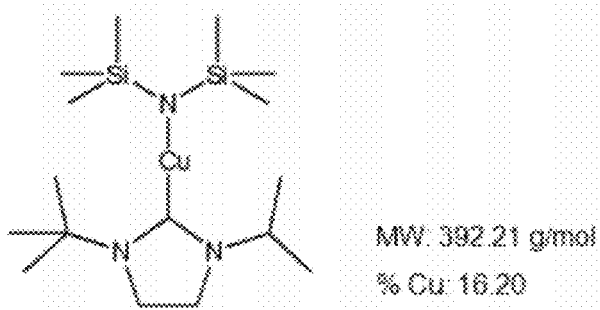
Figure 18:
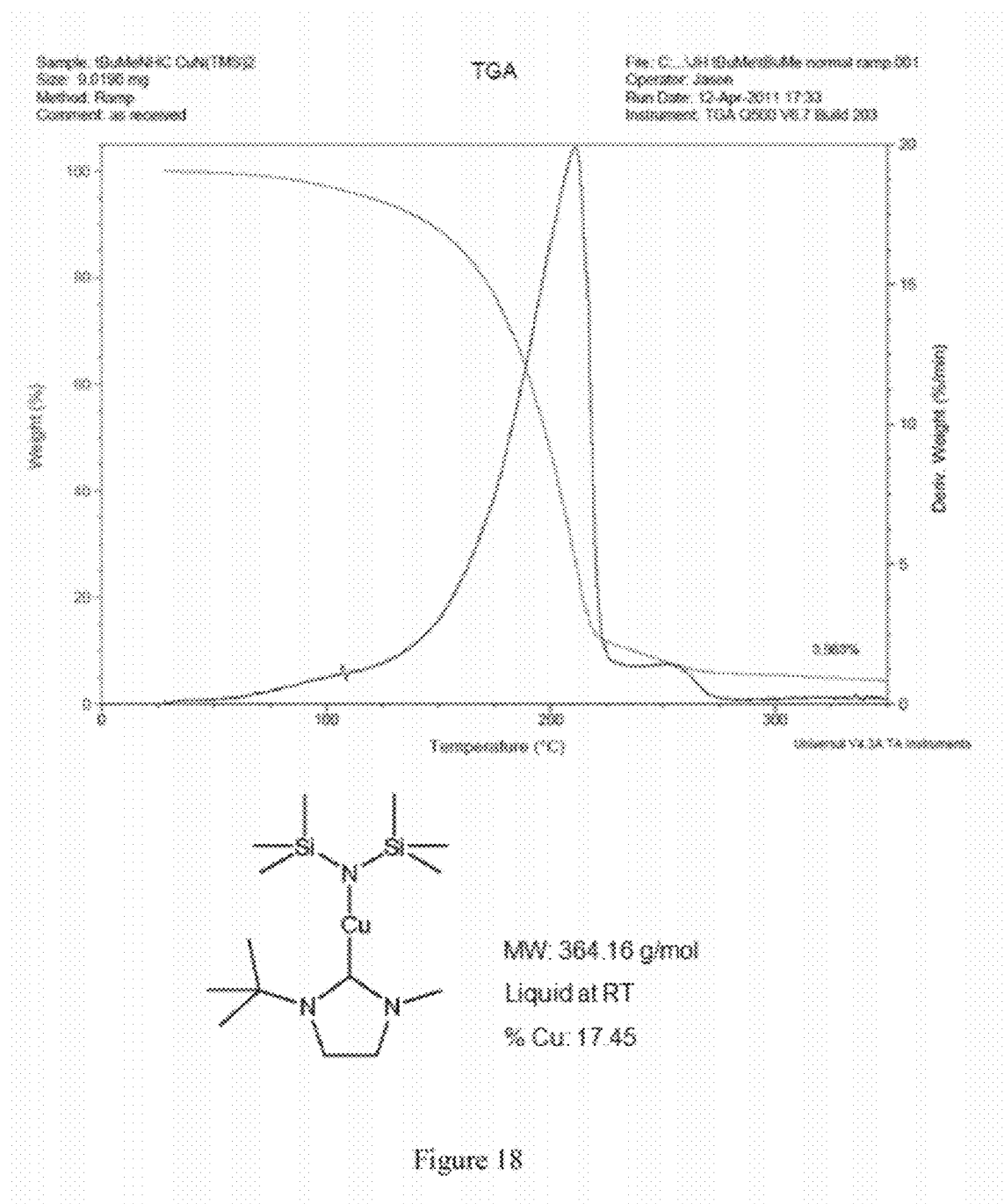
FIG. 18 is a weight loss curve for 1-tert-butyl-3-methyl-imidazolin-2-ylidene copper hexamethyldisilazide (12a)

The results obtained from the saturated analogue of 1,3-di-tert-butyl-imidazol-2-ylidene copper hexamethyldisilazide are depicted in FIG. 14. It is clear, from this direct comparison, that the sNHC-containing compound is volatile and has better thermal stability then the unsaturated analogue. The residual mass of 1.4% shows there was negligible decomposition of the compound during the experiment.

Figure 13:
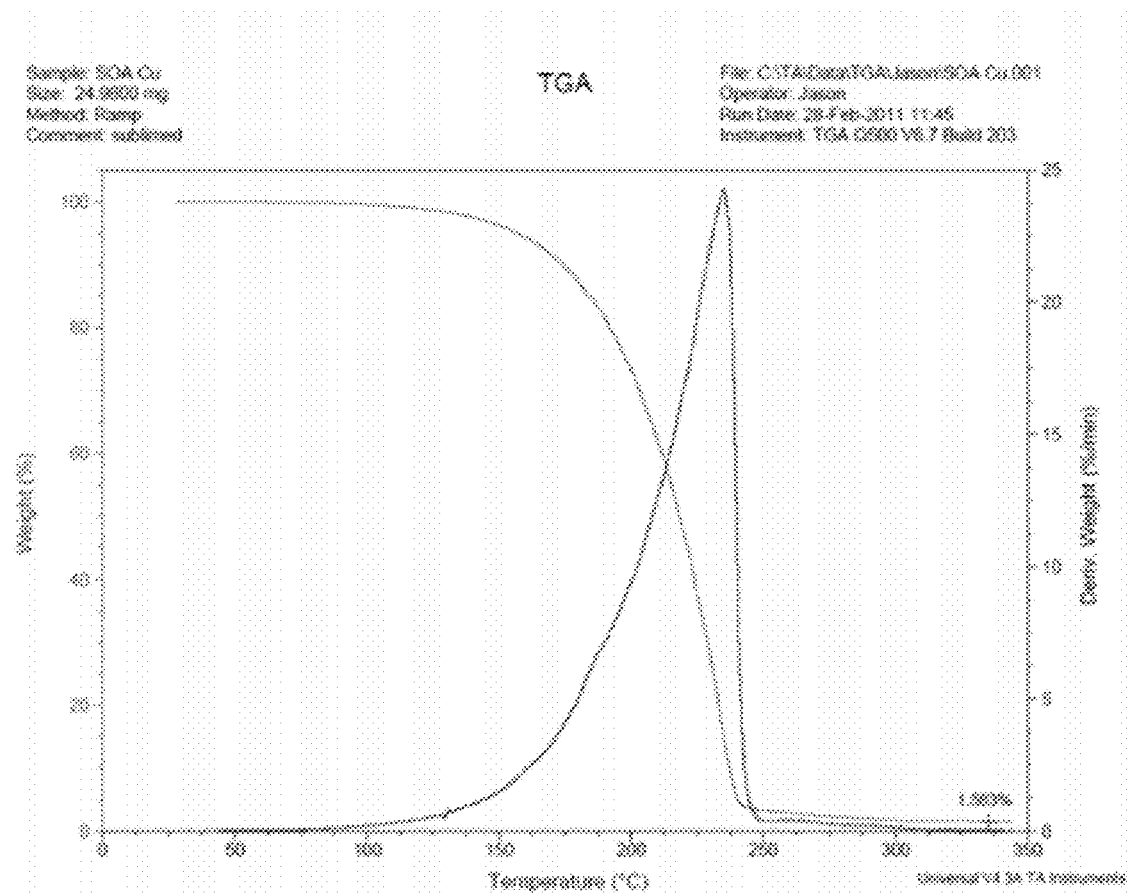
FIG. 13 is a weight loss curve for 1,3-diisopropyl-imidazolin-2-ylidene copper hexamethyldisilazide (2a)
Figure 13:
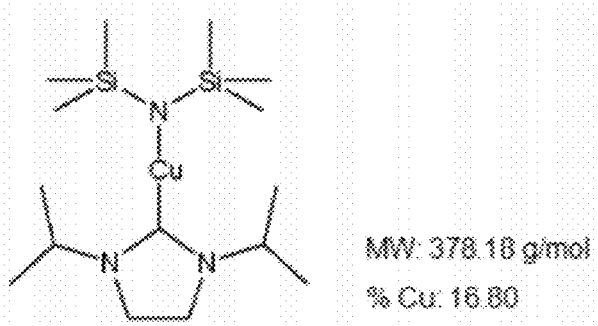

The results obtained from 1,3-diisopropyl-imidazolin-2-ylidene copper hexamethyldisilazide (2a) are depicted in FIG. 13. This compound is not a full analogue of the unsaturated 1,3-diisopropyl-imidazol-2-ylidene compound referred to above, since it does not comprise the 4,5-dimethyl substituents. However, even without these stabilizing substituents, the saturated analogue was found to exhibit better volatility and thermal stability. The residual mass of 1.6% shows there was negligible decomposition of the compound during the experiment.

These examples show that a saturated NHC Cu compound has superior behaviour with respect to volatility and thermal stability than an unsaturated NHC Cu compound. Furthermore, all the sNHC-containing copper compounds tested had a residual mass of less than 7.4% or, more particularly, less than 5%, which was indicative of good volatility.

Figure 19:
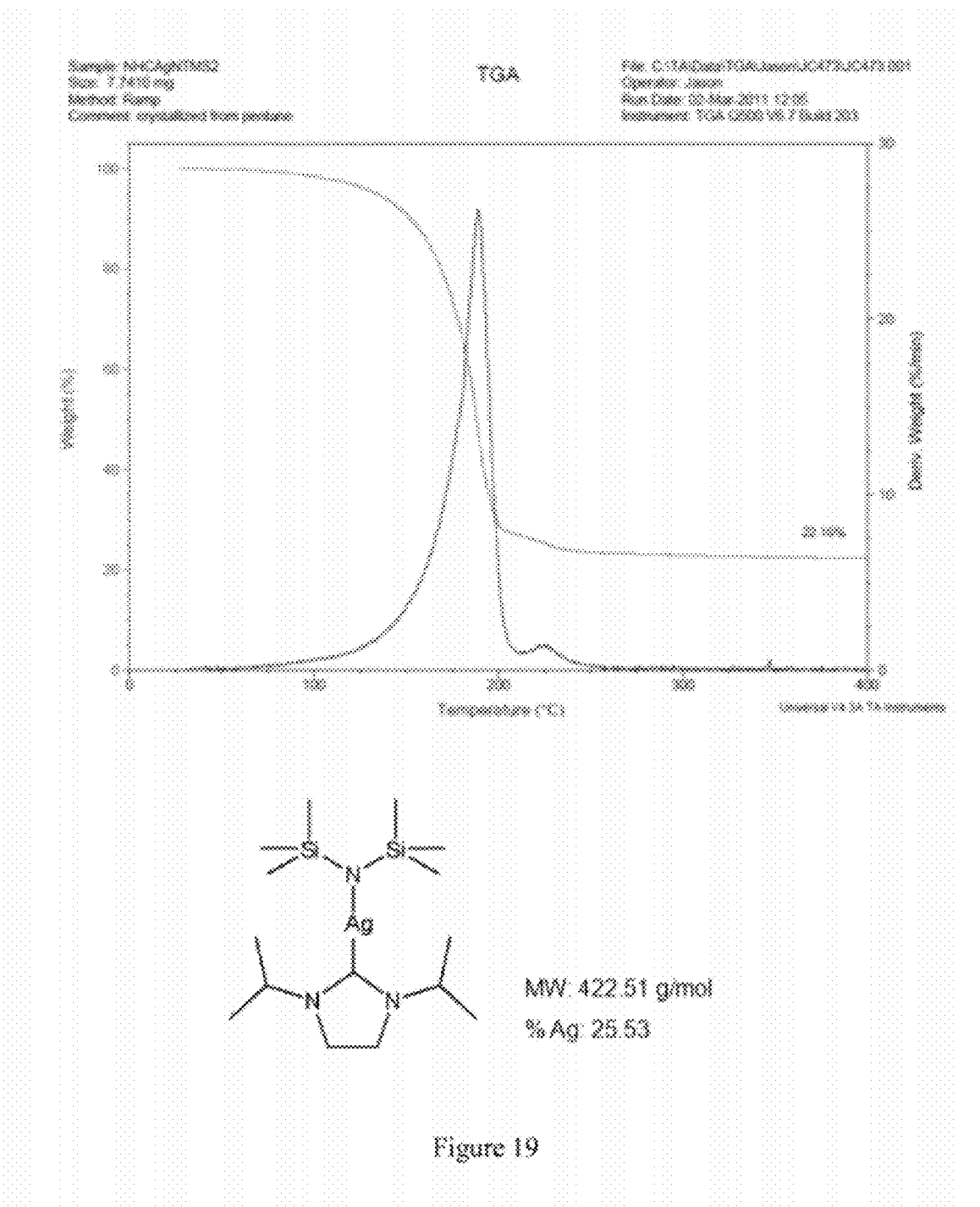
FIG. 19 is a weight loss curve for 1,3-disopropyl-imidazolin-2-ylidene silver hexamethyldisilazide (2b)
Figure 21:
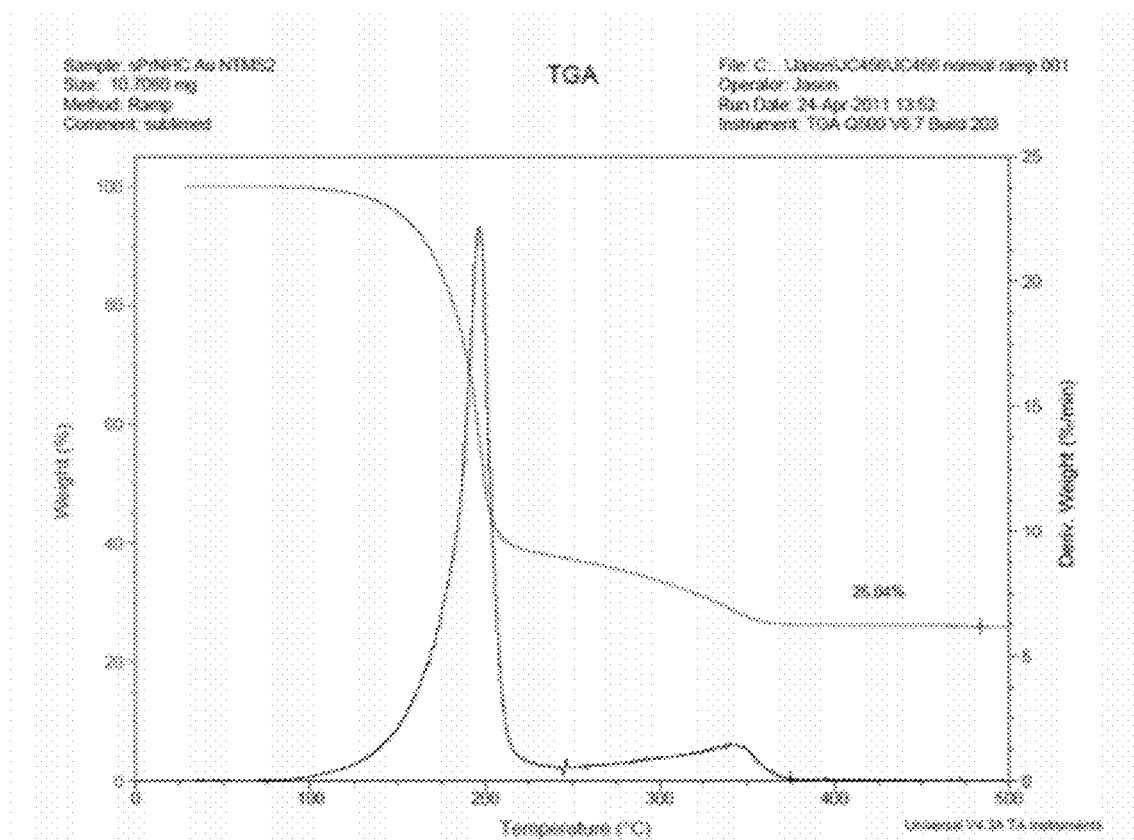
FIG. 21 is a weight loss curve for 1,3-disopropyl-imidazolin-2-ylidene gold hexamethyldisilazide (2c)
Figure 21:
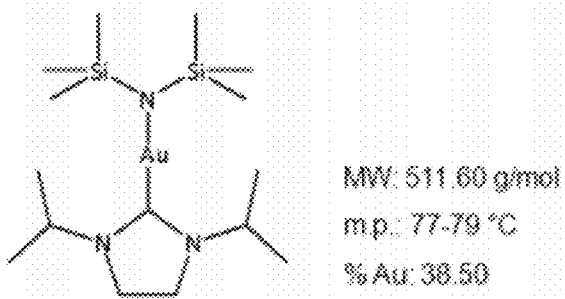

FIGS. 19 and 21 show weight loss curves for sNHC-containing silver and gold compounds, respectively. These compounds also show good volatility since the residual masses were lower than the metal content of the compound. In order to confirm the usefulness of these compounds in ALD, further tests were performed.

Figure 20A:
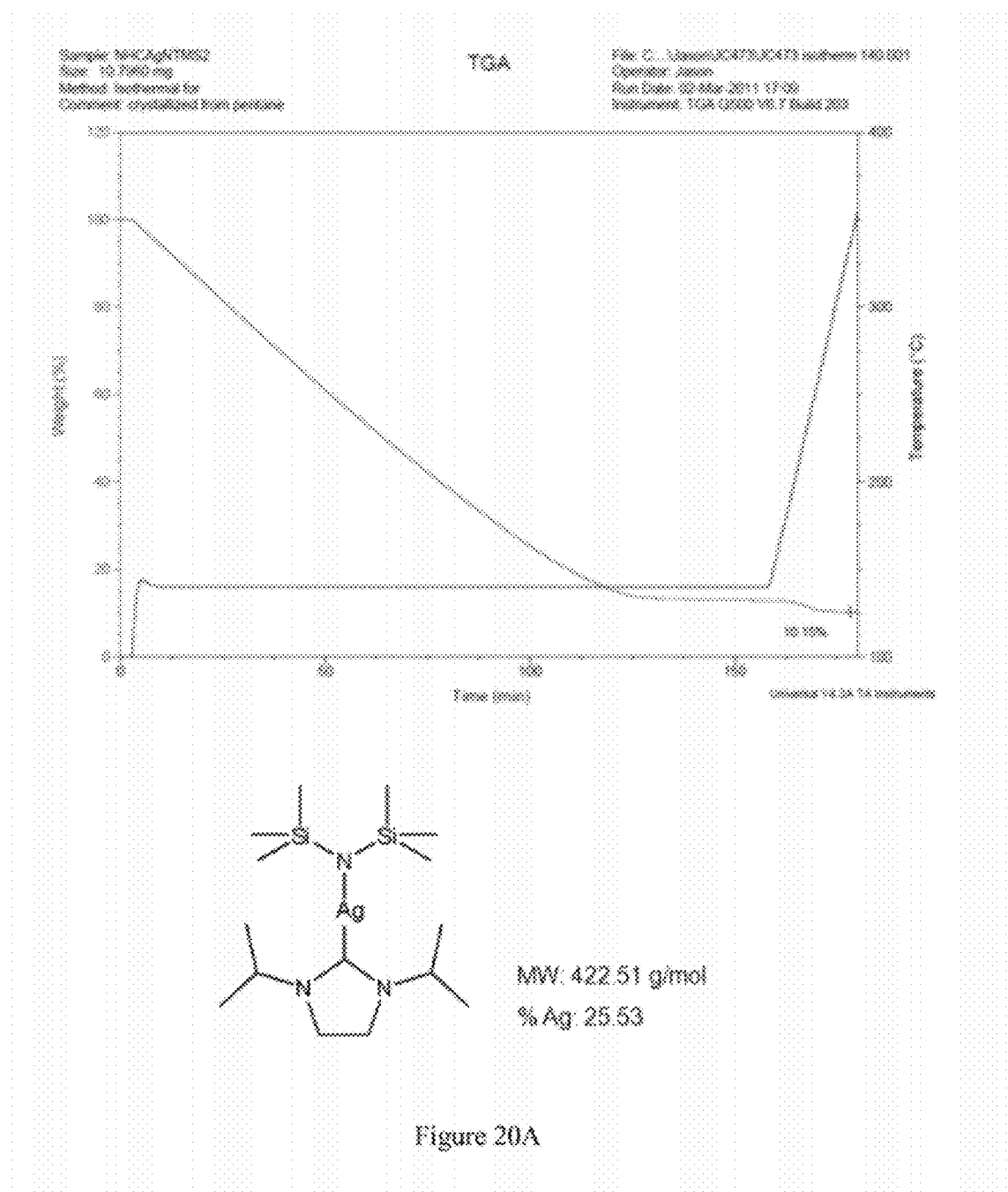
FIG. 20A is a weight loss curve from an isotherm study using 1,3-disopropyl-imidazolin-2-ylidene silver hexamethyldisilazide (2b)

A single isothermal experiment was performed using 1,3-diisopropyl-imidazolin-2-ylidene silver hexamethyldisilazide (2b) whereby the furnace was heated 10° C./min to a low temperature (140° C.) and held for several hours (see FIG. 20A). The residual mass from this experiment was 10.15%, less than half the residual mass observed in the weight loss curve analysis, demonstrating that more of the compound volatilised at hold temperature rather than decomposing in the pan.

With respect to 1,3-diisopropyl-imidazolin-2-ylidene gold hexamethyldisilazide (2c), 3 g of this compound was readily purified by sublimation, which also provides evidence of good volatility.

Figure 20B:
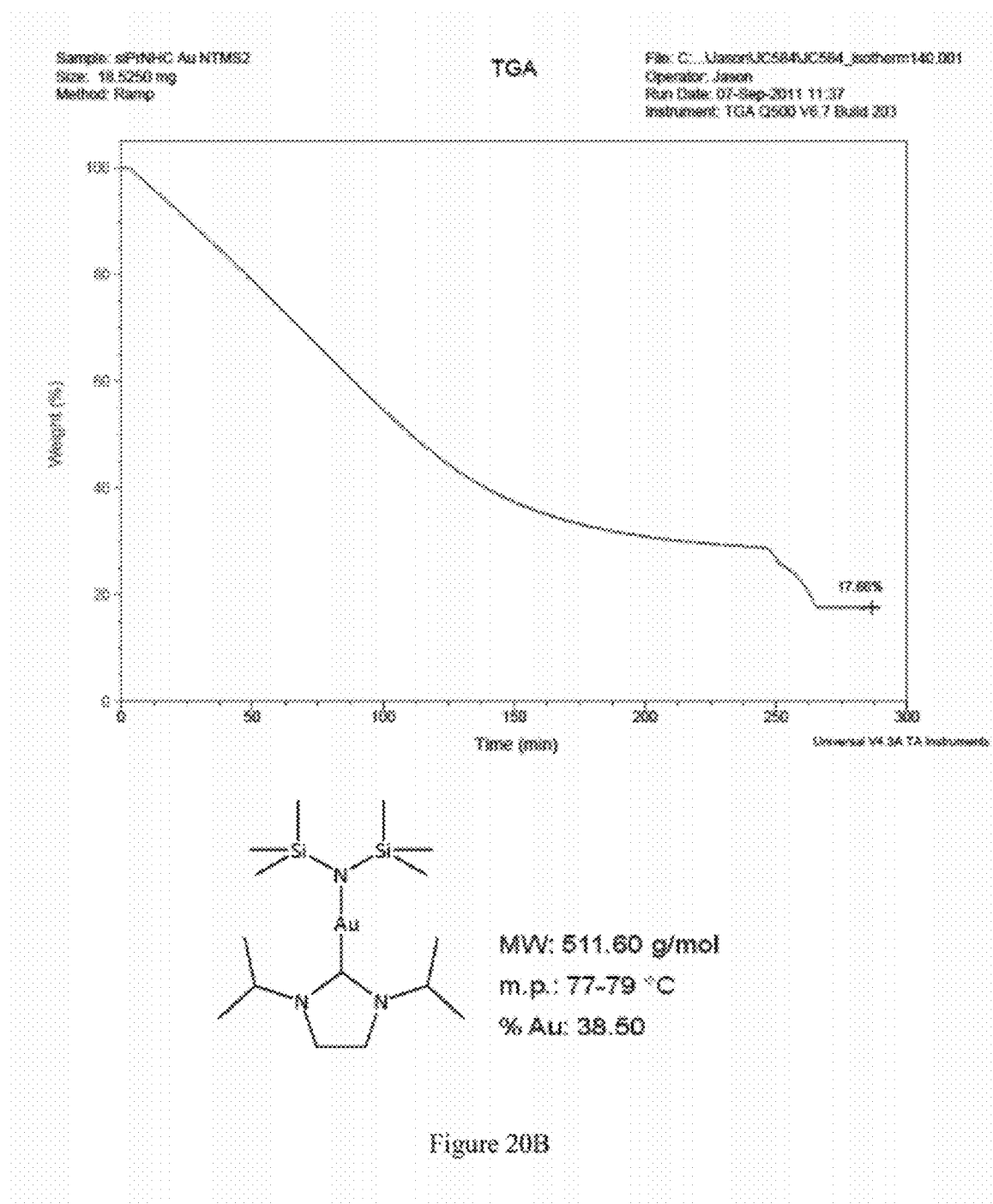
FIG. 20B is a weight loss curve from an isotherm study using 1,3-disopropyl-imidazolin-2-ylidene gold hexamethyldisilazide (2c)

Another single isothermal experiment was performed using 1,3-diisopropyl-imidazolin-2-ylidene gold hexamethyldisilazide (2c) whereby the furnace was heated 10° C./min to a low temperature (140° C.) and held for several hours (see FIG. 20B). The residual mass from this experiment was 17.66%, significantly less than the residual mass observed in the weight loss curve analysis, demonstrating that a significant amount of the compound volatilised at hold temperature rather than decomposing in the pan.

These studies, thus, provided additional evidence of thermal stability and volatility of the sNHC-containing silver and gold compounds at the lower temperatures.

Example 7

Metal Deposition Saturation Curve 1,3-Diisopropyl-4,5-dihydro-imidazolin-2-ylidene copper (I) hexamethyldisilazide (2a) was used in the preparation of a saturation curve to demonstrate an example of successful copper film deposition on a substrate.

In this example, the copper films were deposited by ALD using an ALD system TFS 200 (BENEQ, Finland) employing capacitively-coupled plasma.

A small amount of precursor (0.3-0.5 g) was loaded into an open-topped precursor boat. This boat was inserted into the source tube of the reactor. A flow of 20 sccm $H_2$ in 140 sccm argon was used as the plasma source. A silicon substrate with its native oxide intact was introduced on a 200 mm wafer plate through a load lock. The plasma used was a capacitively coupled plasma using screens to prevent ions from reaching the substrate. It should be noted that the reaction chamber always had 160 sccm of $H_2/N_2$ flowing through it, which was not pulsed.

Pulse length was determined by the ALD deposition experiment. Thus, each data point on the saturation curve can be considered a separate deposition experiment.

Figure 22:
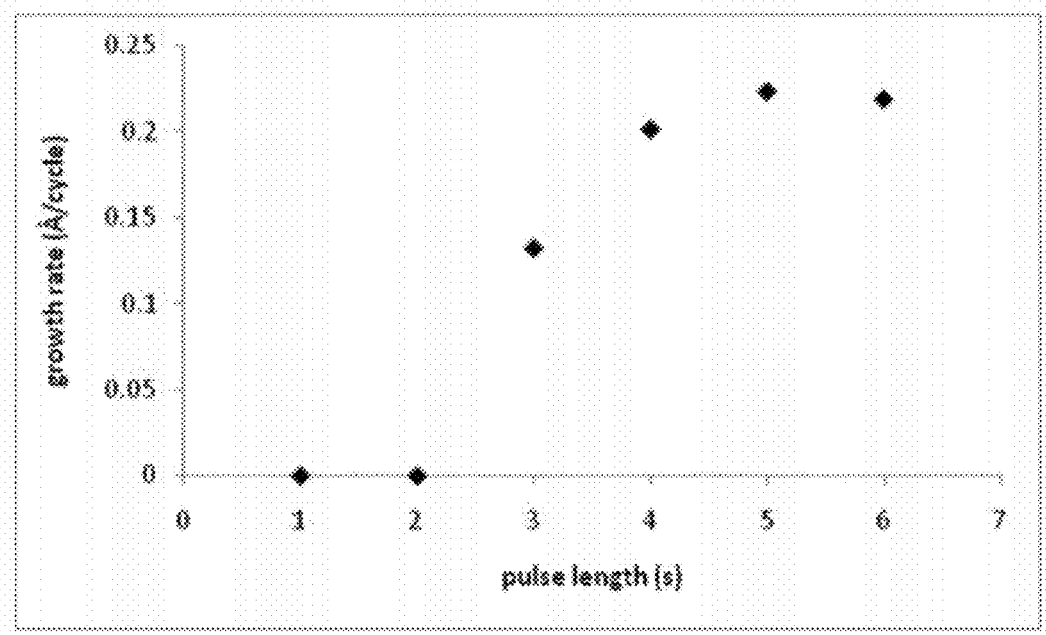
FIG. 22 is a metal deposition saturation curve obtained using 1,3-diisopropyl-imidazolin-2-ylidene copper hexamethyldisilazide (2a) as a precursor in ALD.

The saturation curve obtained using 1,3-isopropylimidazolin-2-ylidene copper(I) hexamethyldisilazide (2a) is shown in FIG. 22. A description of the process used for each point on the curve is provided below.

Film thickness was determined by modelling the K-ratios from the energy dispersive X-ray (EDS) spectrum measured using an Oxford INCA 350 energy dispersive X-ray microanalysis system equipped on the scanning electron microscope (SEM). Thickness was modelled using GMRFILM, a research grade, shareware DOS program for thin film analysis (created by Richard Waldo of General Motors Research Labs; Waldo, R. A., Militello, M. C. and Gaarenstroom, S. W., Surface and Interface Analysis 20: 111-114 (1993)). Growth rate was calculated by dividing the measured thickness by the number of cycles.

Figure 23:
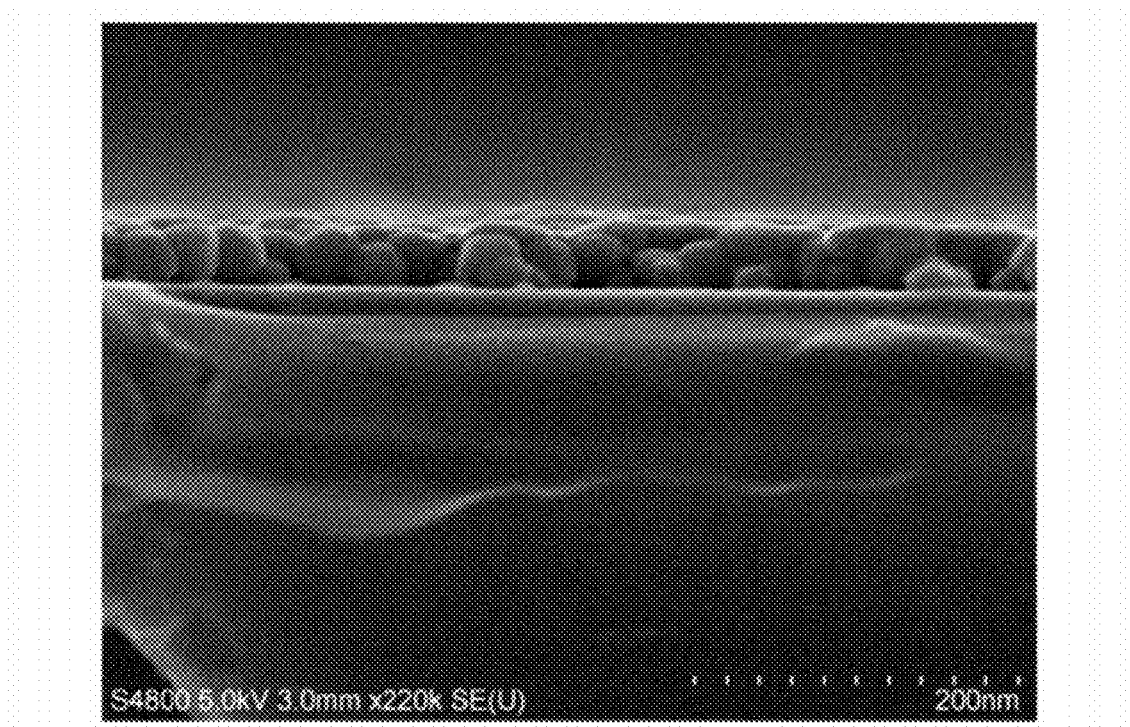
FIG. 23 is an electron micrograph of the thickest film profile of the film produced in obtaining the saturation curve of FIG. 22.

An image of the thickest film profile (FIG. 23) was collected using a Hitachi S-4800 field emission scanning electron microscope (SEM) and the following conditions:

Accelerating Voltage: 5000 Volt

Magnification: 220,000×

Working Distance: 3 mm

The film was measured at 35±2 nm thickness over nine images. The correction of 350/205.2=1.71 has been applied to the saturation curve values measured by EDS. This gives a film (mass) density of 5.24 $g \cdot cm^{-3}$ compared to 8.96 $g \cdot cm^{-3}$ for bulk copper.

At point 1 on the saturation curve the Beneq TFS 200 was employed using capacitively coupled plasma and the following conditions:

| Plasma: | 170 W power with 140 sccm argon carrier gas and 20 sccm hydrogen. |
| --- | --- |
| Temperatures: | 90° C. source temperature using a Beneq HS 500 hot source 225° C. reactor temperature. |
| Carrier gases: | 330 sccm nitrogen to the reactor<br>220 sccm nitrogen to the tool |
| Pulse sequence: | 600 cycles of: 1 seconds of precursor flow<br>3 seconds of nitrogen purge<br>6 seconds of hydrogen plasma<br>3 seconds of nitrogen purge |

At this point no copper could be detected by EDS or seen by SEM.

At point 2 on the saturation curve the Beneq TFS 200 was employed using capacitively coupled plasma and the following conditions:

| Plasma: | 170 W power with 140 sccm argon carrier gas and 20 sccm hydrogen. |
| --- | --- |
| Temperatures: | 90° C. source temperature using a Beneq HS 500 hot source 225° C. reactor temperature. |
| Carrier gases: | 330 sccm nitrogen to the reactor<br>220 sccm nitrogen to the tool |
| Pulse sequence: | 500 cycles of: 2 seconds of precursor flow<br>3 seconds of nitrogen purge<br>6 seconds of hydrogen plasma<br>3 seconds of nitrogen purge |

Following this run no copper could be detected by EDS. However, the SEM showed nanocrystals that were determined to be a heavy element by using backscattered electrons, which, given the reagents used, was considered to be copper.

Figure 24:
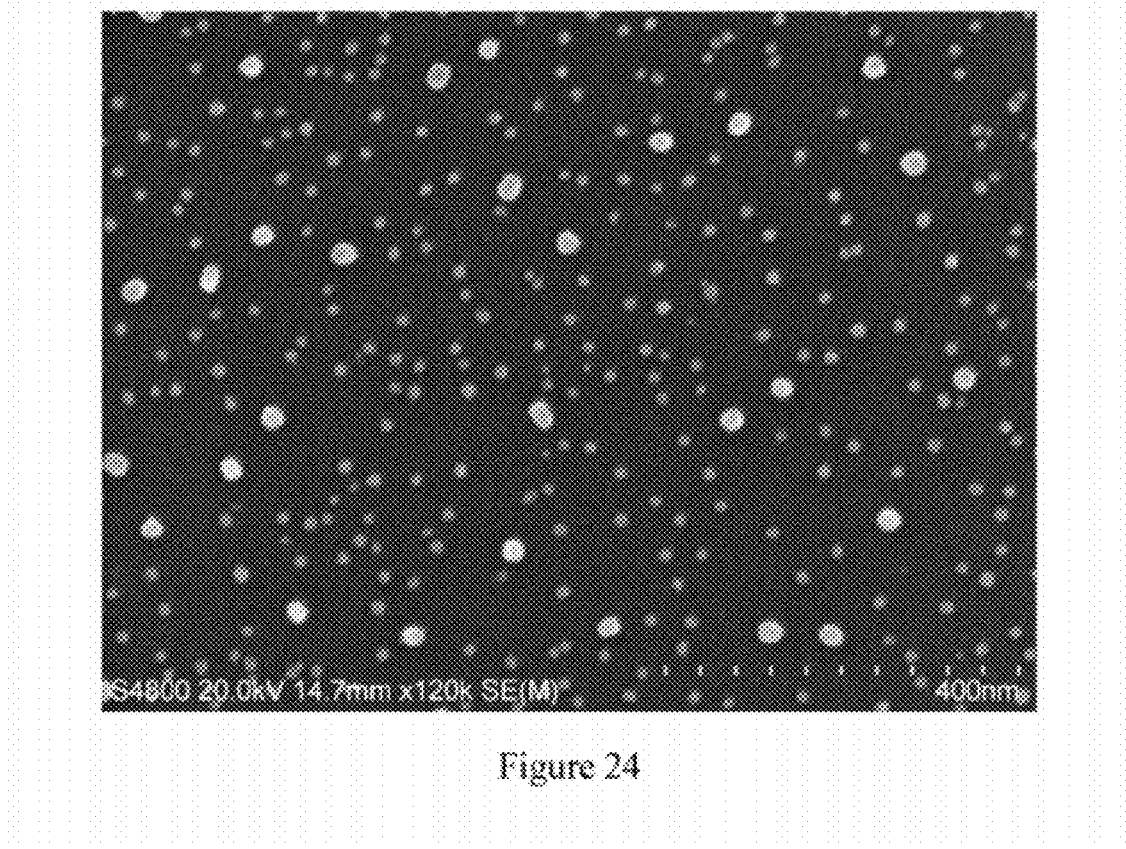
FIGS. 24 and 25 are electron micrographs of the 0 Å film produced at point 2 of the saturation curve of FIG. 22.
Figure 25:
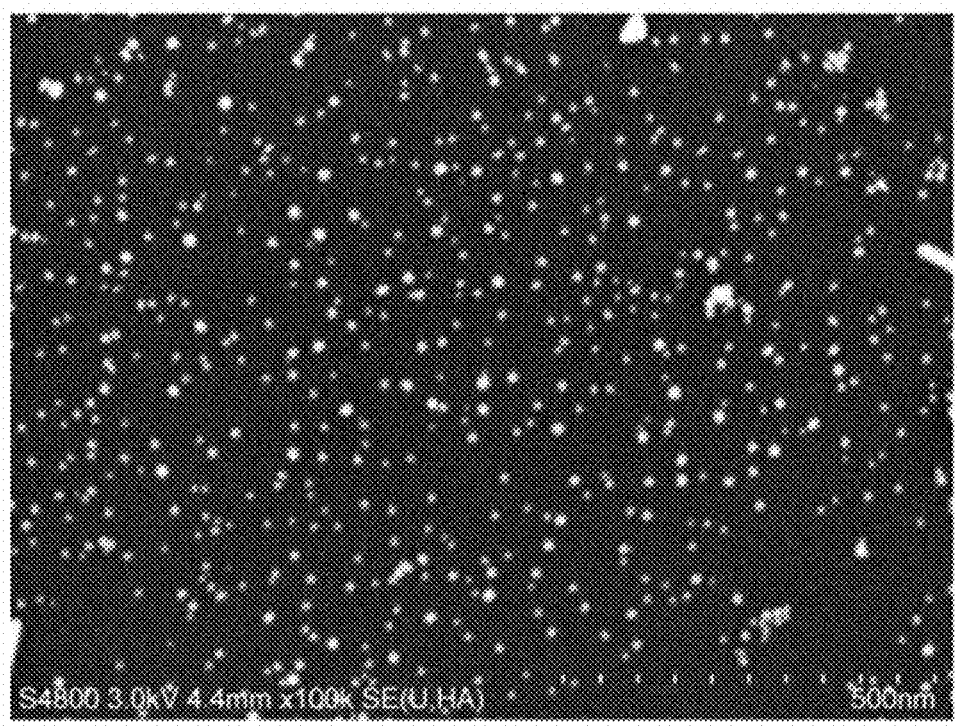

FIGS. 24 and 25 show micrographs of the 0 Å film produced at point 2. The image shown in FIG. 24 was obtained using a Hitachi S-4800 field emission SEM (Accelerating Voltage: 20000 Volt; Magnification: 120000×; Working Distance: 14.7 mm). The image shown in FIG. 25 was obtained using a Hitachi S-4800 field emission SEM (Accelerating Voltage: 3000 Volt; Magnification: 100000×; Working Distance: 4.4 mm). This image is made by backscattered electrons, and shows the nanocrystals to be composed of a heavy element.

At point 3 on the saturation curve the Beneq TFS 200 was employed using capacitively coupled plasma and the following conditions:

| Plasma: | 170 W power with 140 sccm argon carrier gas and 20 sccm hydrogen. |
| --- | --- |
| Temperatures: | 90° C. source temperature using a Beneq HS 500 hot source 225° C. reactor temperature. |
| Carrier gases: | 330 sccm nitrogen to the reactor<br>220 sccm nitrogen to the tool |
| Pulse sequence: | 800 cycles of: 3 seconds of precursor flow<br>3 seconds of nitrogen purge<br>6 seconds of hydrogen plasma<br>3 seconds of nitrogen purge |

The film at point 3 on the saturation curve was approximately 106 Å thick.

At point 4 on the saturation curve the Beneq TFS 200 was employed using capacitively coupled plasma and the following conditions:

| Plasma: | 170 W power with 140 sccm argon carrier gas and 20 sccm hydrogen. |
| --- | --- |
| Temperatures: | 90° C. source temperature using a Beneq HS 500 hot source 225° C. reactor temperature. |
| Carrier gases: | 330 sccm nitrogen to the reactor<br>220 sccm nitrogen to the tool |
| Pulse sequence: | 700 cycles of: 4 seconds of precursor flow<br>3 seconds of nitrogen purge<br>6 seconds of hydrogen plasma<br>3 seconds of nitrogen purge |

Figure 26:
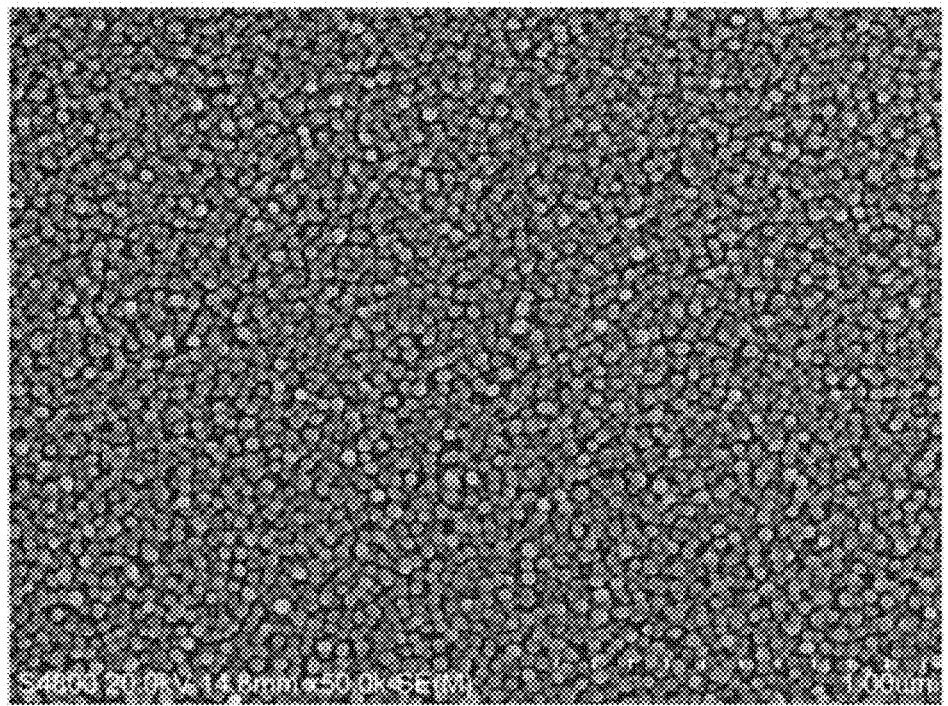
FIGS. 26 and 27 are electron micrographs of the approximately 141 Å film produced at point 4 of the saturation curve of FIG. 22.
Figure 27:
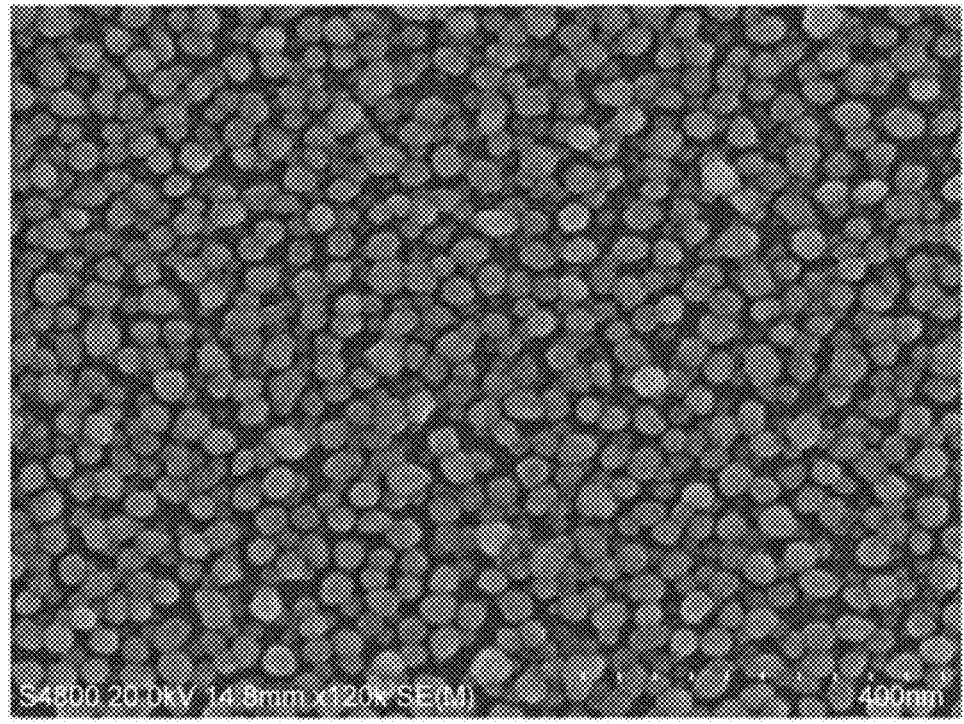

FIGS. 26 and 27 show micrographs of the approximately 141 Å film produced at point 4. The image shown in FIG. 26 was obtained using a Hitachi S-4800 field emission SEM (Accelerating Voltage: 20000 Volt; Magnification: 50000×; Working Distance: 14.8 mm). The image shown in FIG. 27 was obtained using a Hitachi S-4800 field emission SEM (Accelerating Voltage: 20000 Volt; Magnification: 120000×; Working Distance: 14.8 mm).

At point 5 on the saturation curve the Beneq TFS 200 was employed using capacitively coupled plasma and the following conditions:

| Plasma: | 170 W power with 140 sccm argon carrier gas and 20 sccm hydrogen. |
| --- | --- |
| Temperatures: | 90° C. source temperature using a Beneq HS 500 hot source 225° C. reactor temperature. |
| Carrier gases: | 330 sccm nitrogen to the reactor<br>220 sccm nitrogen to the tool |
| Pulse sequence: | 600 cycles of: 5 seconds of precursor flow<br>3 seconds of nitrogen purge<br>6 seconds of hydrogen plasma<br>3 seconds of nitrogen purge |

The film at point 5 on the saturation curve was approximately 134 Å thick.

At point 6 on the saturation curve the Beneq TFS 200 was employed using capacitively coupled plasma and the following conditions:

| Plasma: | 170 W power with 140 sccm argon carrier gas and 20 sccm hydrogen. |
| --- | --- |
| Temperatures: | 90° C. source temperature using a Beneq HS 500 hot source 225° C. reactor temperature. |
| Carrier gases: | 330 sccm nitrogen to the reactor<br>220 sccm nitrogen to the tool |
| Pulse sequence: | 1600 cycles of: 6 seconds of precursor flow<br>3 seconds of nitrogen purge<br>6 seconds of hydrogen plasma<br>3 seconds of nitrogen purge |

Figure 28:
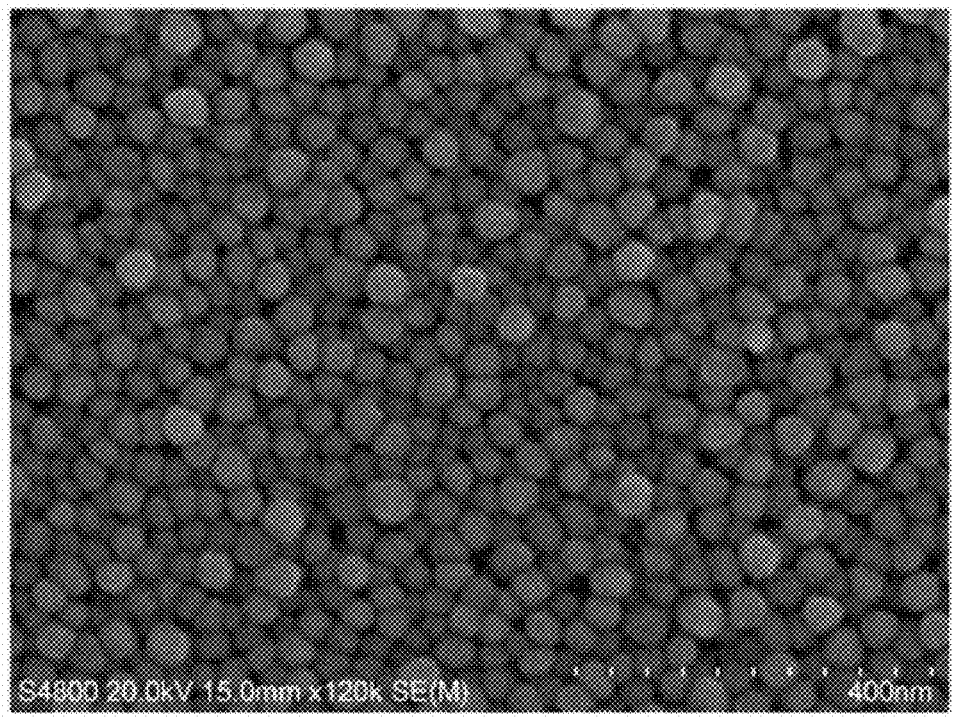
FIGS. 28 and 29 are electron micrographs of the approximately 350 Å film produced at point 6 of the saturation curve of FIG. 22.
Figure 29:
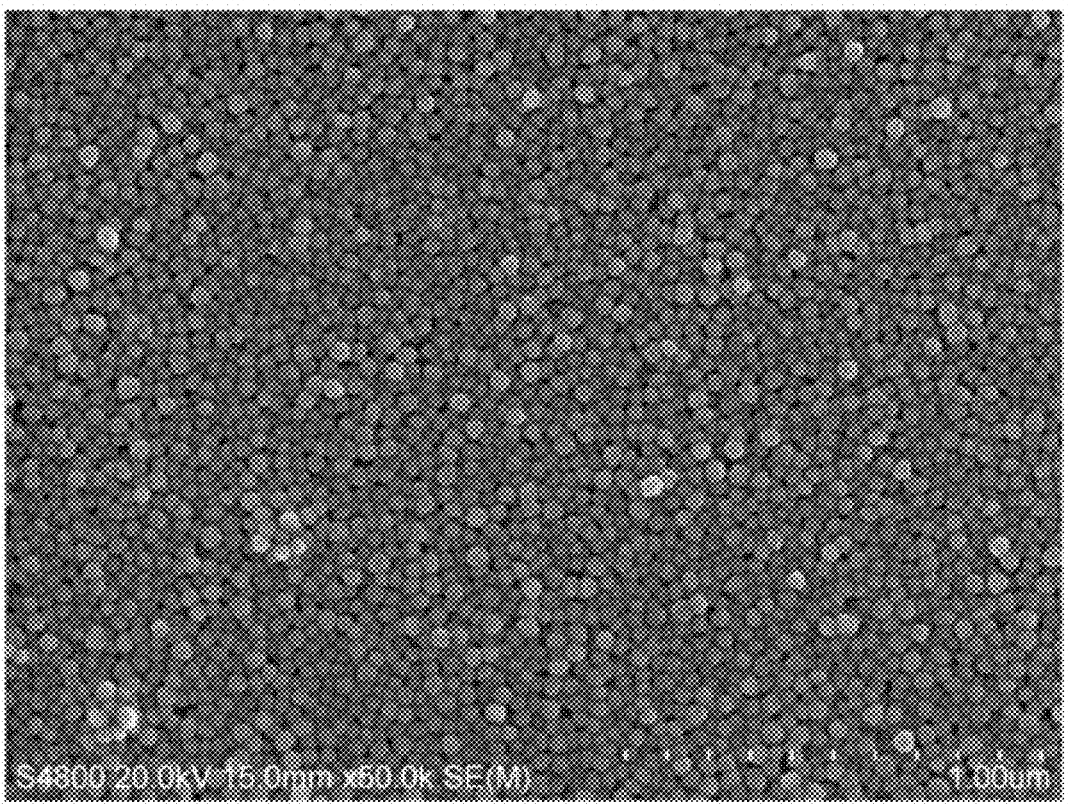

FIGS. 28 and 29 show micrographs of the approximately 350 Å film produced at point 6. The image shown in FIG. 28 was obtained using a Hitachi S-4800 field emission SEM (Accelerating Voltage: 20000 Volt; Magnification: 120000×; Working Distance: 15 mm). The image shown in FIG. 29 was obtained using a Hitachi S-4800 field emission SEM (Accelerating Voltage: 20000 Volt; Magnification: 50000×; Working Distance: 15 mm).

The results of this study demonstrate the successful use of an sNHC metal precursor in ALD. The compound tested was found to perform better than, or equivalent to, two known precursors when evaluated using the parameters listed in Table 2 below, where the "best" values are indicated in bold. The data from the above study are provided under the heading "Example 6".

TABLE 2

Comparison of ALD Parameters using sNHC Metal Precursor and Previously Known Alternatives

| Parameters | Gordon[1] | Eisenbraun[2] | Example 6 |
|---|---|---|---|
| ALD type | thermal | plasma | plasma |
| mp (C) | 77 | 101 | 45 |
| bubbler (C) | 100 | 100 | 90 |
| process (C)[†] | 150 | 100 | 225 |
| stability (C) | 225 | n/a | >300 |
| growth rate, varying Cu (Å) | 0.1 | 0.2 | 0.21 |
| plasma power (W) | n/a | 60 | 170 |
| plasma time (s) | n/a | 16 | 6 |

[1] Li, Z.; Rahtu, A.; Gordon, R. G. *J. Electrochem. Soc.* 2006, 153, C787.
[2] Mao, J.; Eisenbraun, E.; Omarjee, V.; Lansalot, C.; Dussarrat, C. *Mat. Res. Soc. Symp. Proc.* 2010, 1195, B12-05.
[†] There isn't a "best" value in this category.

Example 8

Copper Film Deposition at Ambient Temperature

Mono-metallic precursor compounds 13a and 14a have been shown to successfully deposit copper films from a solution of deuterated benzene. The deuterated benzene was previously dried by treating with sodium metal and benzophenone, degassing by a cycle of freeze-pump-thaw; and vacuum distilling in an air-free solvent storage flask. The dried, deuterated benzene was handled only in a dry, oxygen-free glovebox after distillation.

Samples of the precursor compounds 13a and 14a were prepared for $^1$H NMR analysis inside of the glovebox (under nitrogen atmosphere, 99.99%). Each sample was dissolved in dried $C_6D_6$ and transferred to an NMR tube. The NMR tube was capped inside the glovebox and heavily wrapped in Parafilm immediately after removing from the glovebox in order to avoid exposure of the solution to air.

Figure 30A:
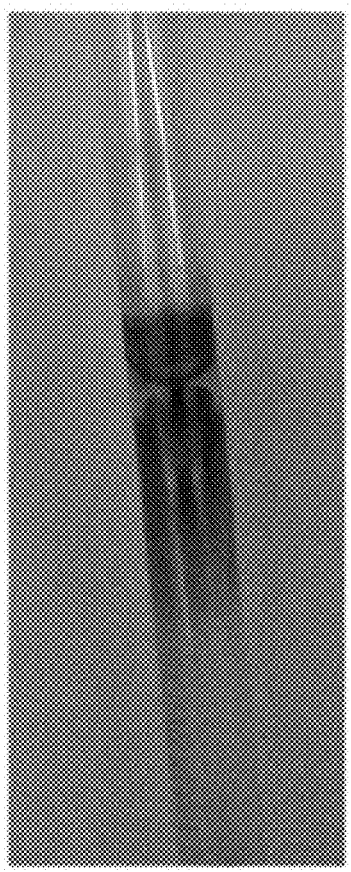
FIGS. 30A and B are photographs of NMR tubes showing copper deposition from mono-metallic precursor compounds on an interior surface of sealed NMR tubes.
Figure 30B:
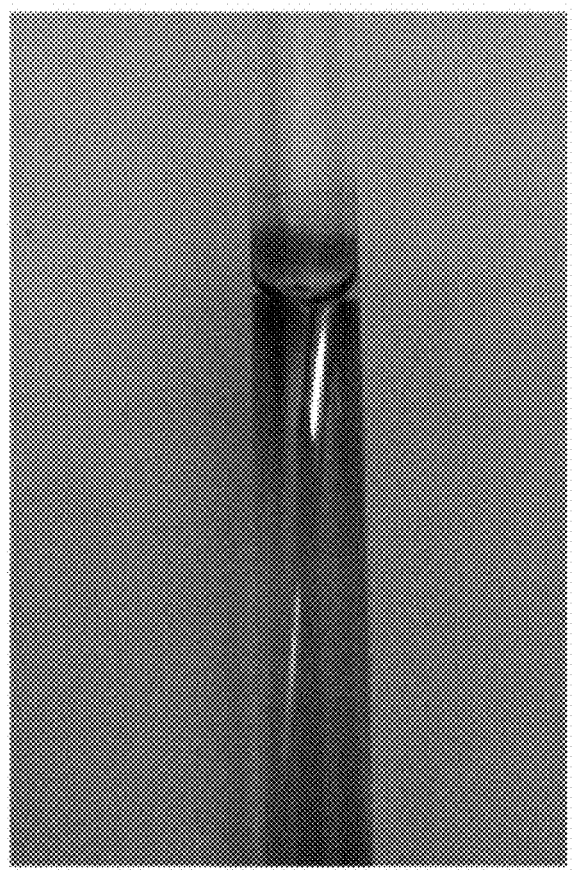

The solutions of the compounds were maintained as prepared (capped, heavily wrapped in Parafilm) under ambient conditions for 7 days. After 7 days a copper-coloured film was observed deposited on the wall of the NMR tubes. A small amount of precipitated green solid was also observed in solution in each case (see, FIGS. 30A and B).

These results indicated that precursor compounds 13a and 14a were able to successfully deposit copper metal films on a substrate.

Example 9

Metal Deposition on Silicon and TiN Substrates 1,3-Diisopropyl-4,5-dihydro-imidazolin-2-ylidene copper (I) hexamethyldisilazide (2a) was used to demonstrate successful copper film deposition to form composite materials comprising two different substrate materials.

In this example, copper films were deposited by ALD using, as the ALD tool, a Picosun SUNALE™ 8200 employing an inductively coupled plasma source. The metal depositions were performed as described above (Example 6), at three reactor temperatures, under the following conditions:

| | |
|---|---|
| Plasma: | 1600 W power, 100 sccm, 90% argon, 10% hydrogen |
| Temperatures: | 140° C. source temperature using a Picosun Picosolid booster; |
| | 150° C., 180° C., and 225° C. reactor temperature |

| | |
|---|---|
| Pulse sequence: | 1000 cycles of: 2 seconds of precursor flow |
| | 5 seconds of nitrogen purge |
| | 10 seconds of hydrogen plasma |
| | 5 seconds of nitrogen purge |

Film thickness was determined and modelled as described above in Example 6. Growth rate was calculated by dividing the thickness by the number of cycles. The results are provided in Table 3, below:

TABLE 3

ALD with Varying Reactor Temperatures

| Reactor Temperature (° C.) | Substrate | Thickness (Å) | GR (Å/cycle) |
|---|---|---|---|
| 225 | Si | 231 | 0.231 |
| | TiN | 164 | 0.164 |
| 180 | Si | 79 | 0.079 |
| | TiN | 107 | 0.107 |
| 150 | Si | 37 | 0.037 |
| | TiN | 32 | 0.032 |

Each of the composite materials formed by the above metal deposition process was subjected to a Scotch tape test, wherein a strip of Scotch tape was adhered to the copper film and then removed. The tape was then examined for evidence of copper film. No peeling of the copper film was observed from any of the composite materials. These results were indicative of good adhesion of the copper films to both substrates.

The results of this study demonstrate the successful use of an sNHC metal precursor in ALD copper metal deposition on an Si and a TiN substrate, using three different reactor temperatures.

Example 10

Synthesis and Characterization of Acyclic Diaminocarbenes

Materials and Methods

All manipulations were performed in an MBraun Labmaster™ 130 Dry box under a nitrogen atmosphere or in nitrogen filled Schlenk lines. NMR spectra were recorded on a 400 MHz Bruker AMX. NMR spectra that were measured in $CDCl_3$ were referenced against TMS. NMR spectra measured in $C_6D_6$ were referenced against residual protonated solvent. Diisopropylformamide, dimethylformamide, dimethylcarbamyl chloride, and phosphoryl chloride were purchased from Alfa Aesar (VWR, Mississauga, Ontario, Canada). Copper(I) chloride, sodium tert-butoxide, diisopropylamine and hexamethyldisilazane were purchased from Sigma Aldrich Inc. (Oakville, Ontario, Canada). The diethyl ether adduct of lithium hexamethyldisilazide was prepared according to Lappert et al. *JACS* 1983, 105, 302.

Diethyl ether and toluene were purchased from Calcdon Laboratories Ltd. (Georgetown, Ontario, Canada) as reagent grade and were purified from an MBraun Solvent Purifier System and stored over 3A molecular sieves. Anhydrous tetrahydrofuran, anhydrous pentane and anhydrous dichloromethane were purchased from Sigma Aldrich Inc. (Oakville, Ontario, Canada) and used as received.

N,N,N',N'-tetramethylformamidinium chloride was prepared according to Wasserman, H. H.; Ives, J. L. *J. Org. Chem.* 1985, 50(19), 3573-3579.

N,N,N',N'-tetraisopropylformamidinium chloride was prepared according to Alder, R. W.; Allen, P. R.; Murray, M.; Orpen, A. G. *Angew. Chem. Int. Ed. Engl.* 1996, 35(10), 1121-1123

Synthesis of N,N,N',N'-tetra isopropyl formamidinylidene copper(I) hexamethyldisilazide 19a

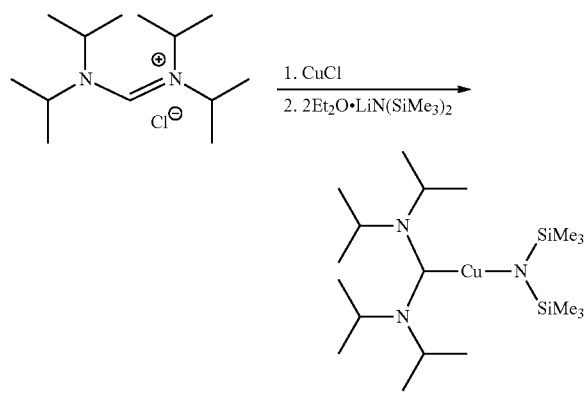

N,N,N',N'-tetraisopropylformamidinylidene copper (I) hexamethyldisilazide 19a

N,N,N',N'-Tetraisopropylformamidinium chloride (0.569 g, 2.29 mmol) was suspended in 30 ml of tetrahydrofuran and copper(I) chloride (0.233 g, 2.35 mmol) was added to the suspension. The suspension was stirred for 18 h. A light pink solid was collected by filtration, washed with 3×2 mL of tetrahydrofuran and then dried under vacuum. (This solid was presumed to be of equal ratio of the formamidinium chloride and copper(I) chloride). The solid was treated with 2 molar equivalents of the diethyl ether adduct of lithium hexamethyldisilazide. The pink solid (0.645 g, 1.85 mmol) was suspended in 30 ml of toluene and cooled to −35° C. The diethyl ether adduct of lithium hexamethyldisilazide (0.895 g, 3.71 mmol) was dissolved in 10 ml of toluene and 10 ml of diethyl ether and added dropwise. The resultant mixture was allowed to warm to room temperature and was stirred for 18 h. The cloudy solution was filtered and the insoluble fraction was washed with 2×2 ml of toluene. The clear filtrate was combined with the washings and concentrated under vacuum to 15 ml. The solution was chilled to −35° C. for 4 days to allow for the crystallization of a colourless solid. The solid was collected by decanting the solution and was dried under vacuum (0.598 g, 59.9%). $^1$H NMR($C_6D_6$): δ 3.28 (4H, sept), δ 1.20 (24H, d), δ 0.54 (s, 18H). $^{13}$C NMR($C_6D_6$): δ 220.95, δ 51.68, δ 24.04, δ 6.83.

An X-ray structure of compound 19a was obtained. The crystals of 19a were mounted on thin glass fibers using paraffin oil and the sample was cooled to 200° K prior to data collection. Data were collected on a Bruker AXS SMART single crystal diffractometer equipped with a sealed Mo tube source (wavelength 0.71073 Å) APEX II CCD detector. Raw data collection and processing were performed with APEX II software package from BRUKER AXS (APEX Software Suite v.2010; Bruker AXS: Madison, Wis., 2005). Diffraction data for 19a sample were collected with a sequence of 0.5° ω scans at 0, 90, 180, and 270° in ϕ. Initial unit cell parameters were determined from 60 data frames collected at the different sections of the Ewald sphere. Semi-empirical absorption corrections based on equivalent reflections were applied (Blessing, R. *Acta Cryst.* 1995, A51, 33).

Systematic absences in the diffraction data-set and unit-cell parameters were consistent with triclinic C2/c (No15) space group. Solutions in centrosymmetric space group yielded chemically reasonable and computationally stable results of refinement. The structure was solved by direct methods, completed with difference Fourier synthesis, and refined with full-matrix least-squares procedures based on $F^2$. In the structure, compound molecules were located on two fold symmetry operator. Molecular packing demonstrated positional disorder of $SiMe_3$ groups and $N(i-Pr)_2$ moieties. For the positions of $SiMe_3$ units, disorder was successfully modeled and computationally stable with the ratio of 50%:50%. However, for the bis-amino part of the structure disorder ration was refining to 55%:45%. All non-hydrogen atoms were refined anisotropically with satisfactory thermal parameter values. Positions of all hydrogen atoms were obtained from the Fourier map analysis. After initial positioning all hydrogen atoms were treated as idealized contributions. All scattering factors were contained in several versions of the SHELXTL program library, with the latest version used being v.6.12 (Sheldrick, G. M. *Acta Cryst.* 2008, A64, 112). Crystallographic data and selected data collection parameters are reported in Table 4a below.

TABLE 4a

Crystallographic data and selected data collection parameters.

| Compound | 19a |
|---|---|
| Empirical formula | $CuC_{19}H_{46}N_3Si_2$ |
| Formula weight | 436.31 |
| Crystal size, mm | 0.27 × 0.20 × 0.14 |
| Crystal system | Monoclinic |
| Space group | C2/c No15 |
| Z | 4 |
| a, Å | 15.3322(5) |
| b, Å | 12.6279(4) |
| c, Å | 14.4925(5) |
| α, ° | 90 |
| β, ° | 107.7560(10) |
| γ, ° | 90 |
| Volume, Å$^3$ | 2672.28(15) |
| Calculated density, Mg/m$^3$ | 1.084 |
| Absorption coefficient, mm$^{-1}$ | 0.914 |
| F(000) | 952 |
| Θ range for data collection, ° | 2.13 to 28.32 |
| Limiting indices | h = ±20, k = ±15, l = ±19 |
| Reflections collected/unique | 208365/3282 |
| R(int) | 0.0188 |
| Completeness to Θ = 28.32, % | 98.4 |
| Max. and min. transmission | 0.8827 and 0.7904 |
| Data/restraints/parameters | 3282/116/214 |
| Goodness-of-fit on F$^2$ | 1.059 |
| Final R indices [I > 2σ(I)] | $R_1$ = 0.0223, $wR_2$ = 0.0559 |
| R indices (all data) | $R_1$ = 0.0262, $wR_2$ = 0.0582 |
| Largest diff. peak/hole, e · Å$^{-3}$ | 0.268 and −0.152 |

Figure 31A:
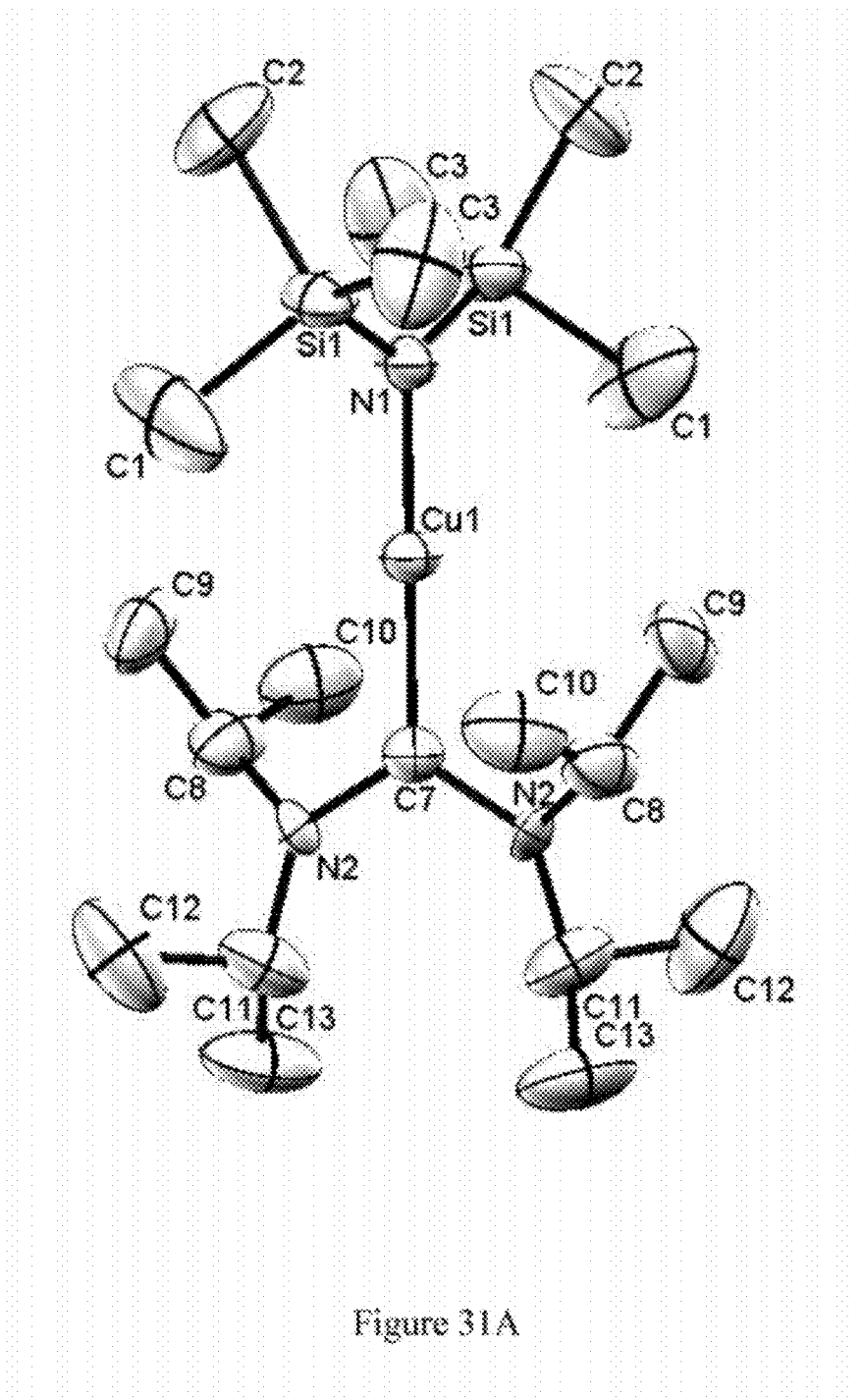
FIG. 31A is an ORTEP drawing of the X-ray crystal structure of N,N,N',N'-tetraisopropylformamidinylidene copper hexamethyldisilazide (19a)

An ORTEP drawing of the X-ray crystal structure of compound 19a is depicted in FIG. 31A.

Synthesis I of N,N,N',N'-tetramethylformamidinylidene copper(I) hexamethyldisilazide 17a

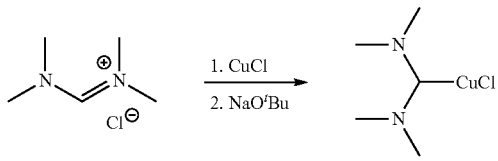

N,N,N',N'-tetramethylformamidinylidene copper(I) chloride

In 80 ml of tetrahydrofuran, N,N,N',N'-tetramethylformamidinium chloride (3.018 g, 22.1 mmol) was suspended and copper(I) chloride (2.255 g, 22.8 mmol) was added. The resultant mixture stirred for 15 min. A solution of sodium tert-butoxide (2.188 g, 22.8 mmol) was dissolved in 20 ml of tetrahydrofuran and added dropwise. The resultant mixture was stirred for 24 h. The product suspension was filtered through a pad of Celite™ and the insoluble fraction was washed with 3×10 ml of tetrahydrofuran. The filtrate and washings were combined and the volatiles were stripped under reduced pressure. The solid residue was dissolved in 15 ml of $CH_2Cl_2$ and concentrated under reduced pressure to 10 ml. The solution was chilled to −35° C. for 24 h. Light brown crystals were collected by decanting the solution and drying under vacuum (1.731 g, 39.3%). $^1$H NMR ($CDCl_3$): δ 3.24 (12H, s). $^{13}$C NMR ($CDCl_3$): δ 211.13, δ 45.07.

N,N,N',N'-tetramethylformamidinylidene copper(I) hexamethyldisilazide 17a

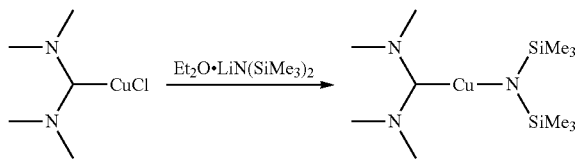

N,N,N',N'-tetramethylformamidinylidene copper(I) hexamethyldisilazide: N,N,N',N'-tetramethylformamidinylidene copper(I) chloride (0.369 g, 1.85 mmol) was suspended in 30 mL of toluene and chilled to −35° C. The diethyl ether adduct of lithium hexamethyldisilazide (0.447 g, 1.85 mmol) was dissolved in 10 ml of toluene and 5 ml of diethyl ether and added dropwise. The resultant mixture was allowed to warm to room temperature and was stirred for 24 h. The cloudy solution was filtered and the insoluble fraction was washed with 2×2 ml of toluene. The clear filtrate was combined with the washings and concentrated under vacuum to 1 ml. 6 ml of pentane was added and the solution was chilled to −35 for 2 h. Colourless needle crystals were collected by decanting the solution and drying under vacuum (0.298 g, 49.7%). $^1$H NMR($C_6D_6$): δ 2.43 (12H, s), δ 0.56 (18H, s). $^{13}$C NMR($C_6D_6$): δ 214.14, δ 44.01, δ 7.23.

Synthesis II of N,N,N',N'-tetramethylformamidinylidene copper(I) hexamethyldisilazide 17a This synthesis of compound 17a is similar to the Synthesis I above, except that in this procedure the intermediate carbene copper chloride was not isolated.

N,N,N',N'-tetramethylformamidinylidene copper(I) hexamethyldisilazide

N,N,N',N'-tetramethylformamidinium chloride (4.21 g, 30.8 mmol) was suspended in 100 mL of tetrahydrofuran. Copper(I) chloride (3.15 g, 31.8 mmol) was added to the suspension. The diethyl ether adduct of lithium hexamethyldisilazide (14.90 g, 61.7 mmol) was dissolved in 60 ml of tetrahydrofuran and added dropwise to the suspension. The resultant mixture was stirred for 15 h. Volatiles were stripped under reduced pressure. The residue was extracted with 30 ml of pentane and then filtered through a medium porosity frit. The insoluble fraction was washed with 3×10 ml of pentane. The filtrate and washings were combined and the solution was stripped to dryness under reduced pressure. The solid residue was sublimed (20 mtorr, 90° C.) to afford a product yield of 8.746 g, 87.5%. $^1$H NMR($C_6D_6$): δ 2.43 (12H, s), δ 0.56 (18H, s). $^{13}$C NMR ($C_6D_6$): δ 214.14, δ 44.01, δ 7.23.

An X-ray structure of compound 17a was obtained. A crystal of compound 17a was mounted on thin glass fibers using paraffin oil and the sample was cooled to 200° K prior to data collection. Data were collected on a Bruker AXS SMART single crystal diffractometer equipped with a sealed Mo tube source (wavelength 0.71073 Å) APEX II CCD detector. Raw data collection and processing were performed with APEX II software package from BRUKER AXS (APEX Software Suite v.2010; Bruker AXS: Madison, Wis., 2005.). Diffraction data for the compound 17a sample were collected with a sequence of 0.5° ω scans at 0, 90, 180, and 270° in φ. Initial unit cell parameters were determined from 36 data frames collected at the different sections of the Ewald sphere. Semi-empirical absorption corrections based on equivalent reflections were applied (Blessing, R. *Acta Cryst.* 1995, A51, 33). Systematic absences in the diffraction data-set and unit-cell parameters were consistent with triclinic P-1 (No2) space group. Solutions in centrosymmetric space group yielded chemically reasonable and computationally stable results of refinement. The structure was solved by direct methods, completed with difference Fourier synthesis, and refined with full-matrix least-squares procedures based on $F^2$. In the structure compound molecules are situated in the general position. All non-hydrogen atoms were refined anisotropically with satisfactory thermal parameters values. Positions of all hydrogen atoms were obtained from the Fourier map analysis. After initial positioning all hydrogen atoms were treated as idealized contributions. All scattering factors are contained in several versions of the SHELXTL program library, with the latest version used being v.6.12 (Sheldrick, G. M. *Cell_Now*, 2004, Bruker-AXS, Inc., Madison, Wis.). Crystallographic data and selected data collection parameters are reported in Table 4b below.

TABLE 4b

Crystallographic data and selected data collection parameters.

| Compound | 17a |
|---|---|
| Empirical formula | $CuC_{11}H_{30}N_3Si_2$ |
| Formula weight | 324.10 |
| Crystal size, mm | 0.19 × 0.17 × 0.13 |
| Crystal system | Triclinic |
| Space group | P-1 No2 |
| Z | 2 |
| a, Å | 8.6287(5) |
| b, Å | 9.6320(5) |
| c, Å | 11.7862(6) |
| α, ° | 80.207(2) |
| β, ° | 82.472(2) |
| γ, ° | 67.289(2) |
| Volume, Å$^3$ | 888.15(8) |
| Calculated density, Mg/m$^3$ | 1.212 |
| Absorption coefficient, mm$^{-1}$ | 1.352 |
| F(000) | 348 |
| Θ range for data collection, ° | 2.31 to 28.30 |
| Limiting indices | h = ±10, k = ±11, l = ±15 |
| Reflections collected/unique | 8286/4305 |
| R(int) | 0.0131 |
| Completeness to Θ = 28.34, % | 97.2 |
| Max. and min. transmission | 0.8438 and 0.7832 |
| Data/restraints/parameters | 4305/0/154 |
| Goodness-of-fit on F$^2$ | 1.042 |
| Final R indices [I > 2σ(I)] | $R_1$ = 0.0232, w$R_2$ = 0.0642 |
| R indices (all data) | $R_1$ = 0.0265, w$R_2$ = 0.0664 |
| Largest diff. peak/hole, e · Å$^{-3}$ | 0.354 and −0.266 |

Figure 31B:
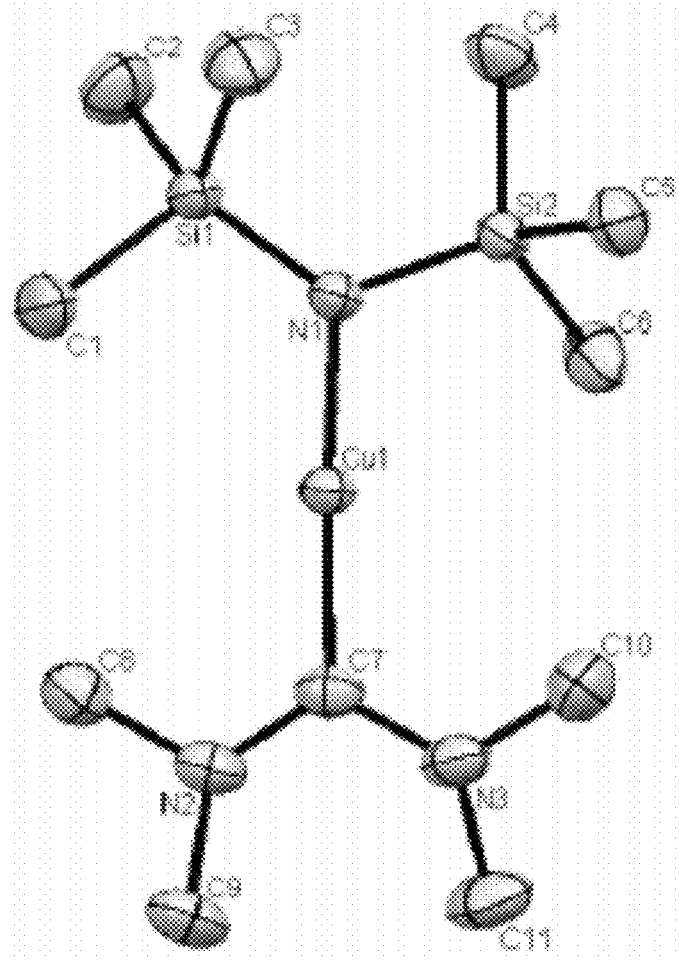
FIG. 31B is an ORTEP drawing of the X-ray crystal structure of N,N,N',N'-tetramethylformamidinylidene copper(I) hexamethyldisilazide (17a)

An ORTEP drawing of the X-ray crystal structure of compound 17a is depicted in FIG. 31B.

Example 11

Thermogravimetric Analysis of Compounds Containing Acyclic Diaminocarbenes

Vapour pressures of a two acyclic diaminocarbene-containing copper precursor compounds were measured on a TA Instruments Q50 thermogravimetric (TG) analyser located in an MBraun Labmaster 130 Dry box under a nitrogen atmosphere. The TG analyzer was run in a stepped isotherm as set out below.

Ramp program for N,N,N',N'-tetramethylformamidinylidene copper(I) hexamethyldisilazide 17a:
1: Ramp 40.00° C./min to 110.00° C.
2: Isothermal for 15.00 min
3: Ramp 40.00° C./min to 120.00° C.
4: Isothermal for 15.00 min
5: Ramp 40.00° C./min to 130.00° C.
6: Isothermal for 15.00 min
7: Ramp 40.00° C./min to 140.00° C.
8: Isothermal for 15.00 min
9: Ramp 40.00° C./min to 150.00° C.
10: Isothermal for 15.00 min
11: Ramp 40.00° C./min to 160.00° C.
12: Isothermal for 15.00 min
13: Ramp 40.00° C./min to 170.00° C.
14: Isothermal for 15.00 min
15: Ramp 40.00° C./min to 180.00° C.
16: Isothermal for 120.00 min
17: Ramp 40.00° C./min to 600.00° C.

Ramp program for N,N,N',N'-tetra isopropyl formamidinylidene copper(I) hexamethyldisilazide 19a:
1: Ramp 40.00° C./min to 110.00° C.
2: Isothermal for 15.00 min
3: Ramp 40.00° C./min to 120.00° C.
4: Isothermal for 10.00 min
5: Ramp 40.00° C./min to 130.00° C.
6: Isothermal for 10.00 min
7: Ramp 40.00° C./min to 140.00° C.
8: Isothermal for 10.00 min
9: Ramp 40.00° C./min to 150.00° C.
10: Isothermal for 10.00 min
11: Ramp 40.00° C./min to 160.00° C.
12: Isothermal for 10.00 min
13: Ramp 40.00° C./min to 170.00° C.
14: Isothermal for 10.00 min
15: Ramp 40.00° C./min to 180.00° C.
16: Isothermal for 10.00 min
17: Ramp 40.00° C./min to 190.00° C.
18: Isothermal for 10.00 min
19: Ramp 40.00° C./min to 200.00° C.
20: Isothermal for 10.00 min
21: Ramp 10.00° C./min to 600.00° C.

As in Example 5, the slope was determined for each isotherm interval, and if the data was linear for that interval, that was used as the "Δm/Δt" value for that temperature. The pressure was calculated using the Langmuir equation following the method of Umarji [G. V. Kunte, S. A. Shivashanker, A. M. Umarji Meas. Sci. Tech. 2008, 19, 025704] for estimation of vapour pressure. Benzoic acid was used as a standard to determine the a coefficient of the Langmuir equation (i.e., the Langmuir adsorption constant), and Cu(tmhd)$_2$ was used as a benchmark.

Figure 32:
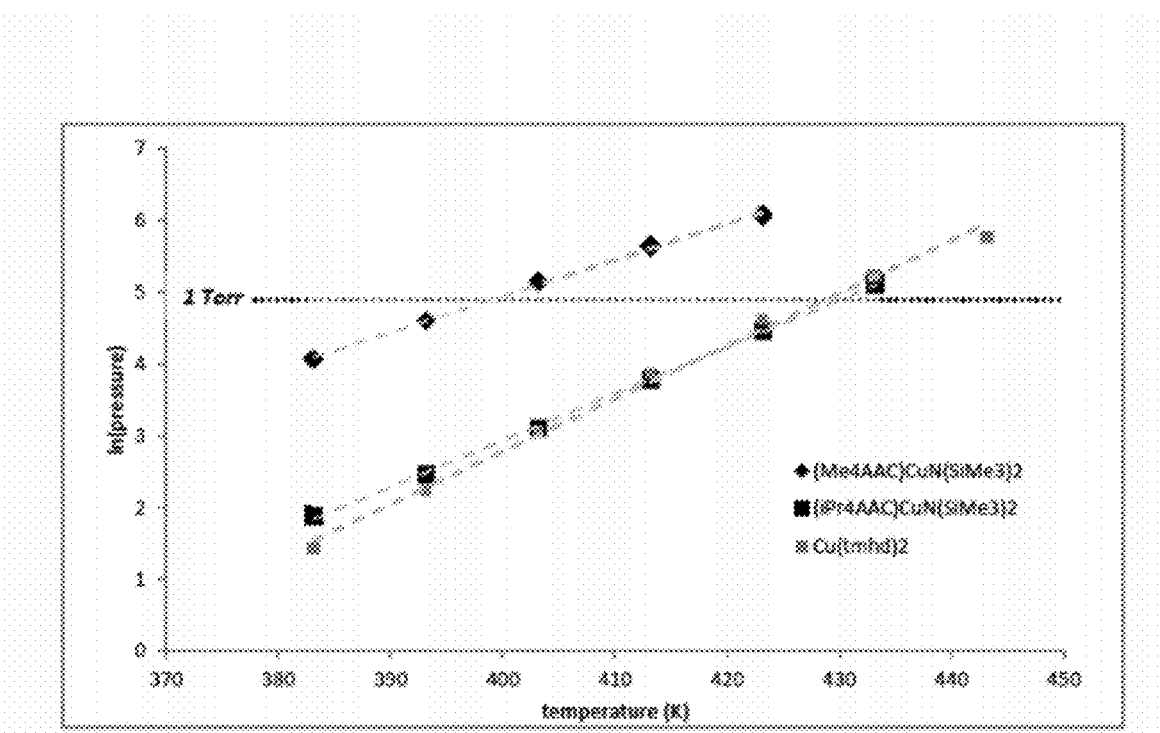
FIG. 32 is a graph of vapour pressure plots for two acyclic diaminocarbene-containing mono-metallic precursor compounds in comparison to a control (copper bis-(2,2,6,6-tetramethyl-3,5-heptadionate)

The results from vapour testing of the two acyclic diaminocarbene-containing copper precursor compounds are depicted in FIG. 32. The compound, Cu(tmhd)$_2$, was used as a control. The temperatures at which compounds 17a and 19a have a vapour pressure of 1 torr were 126° C. and 157° C., respectively.

Further TG analysis was performed on the TA Instruments Q50 thermogravimetric (TG) analyser located in an MBraun Labmaster 130 Dry box under a nitrogen atmosphere (99.999% at a flow rate of 100 mL/min) to obtain weight loss curves. During testing the furnace was heated at 10° C./min from 30 to 600° C. Samples of the compounds to be studied were provided in platinum pans with diameters of 1 cm. The mass of each sample tested was within the range of from about 10 to about 30 mg. The mass ("weight") of the sample was obtained as the temperature was increased and plotted.

Figure 33:
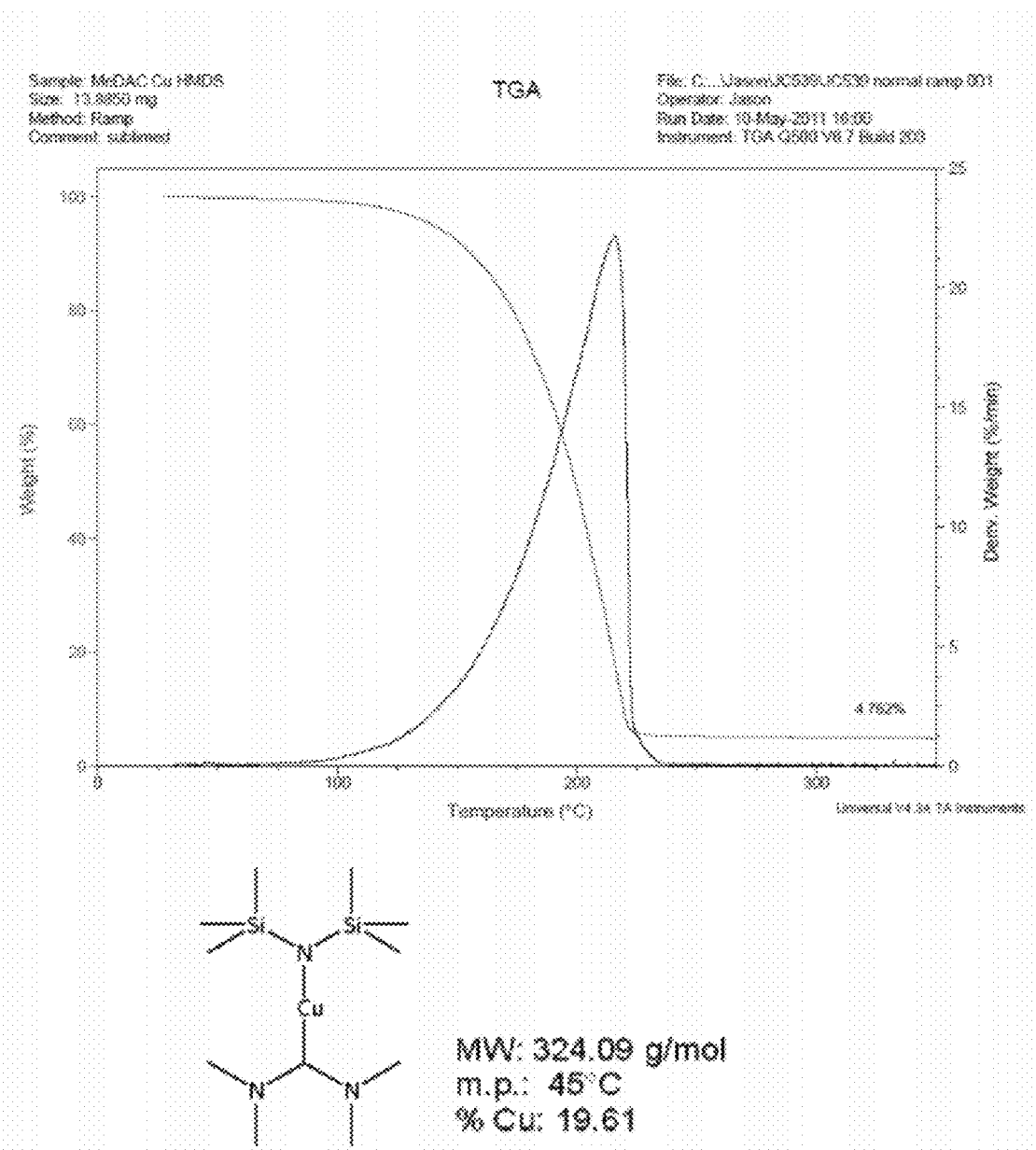
FIG. 33 is a weight loss curve for N,N, N', N'-tetramethylformamidinylidene copper hexamethyldisilazide (17a)
Figure 34:
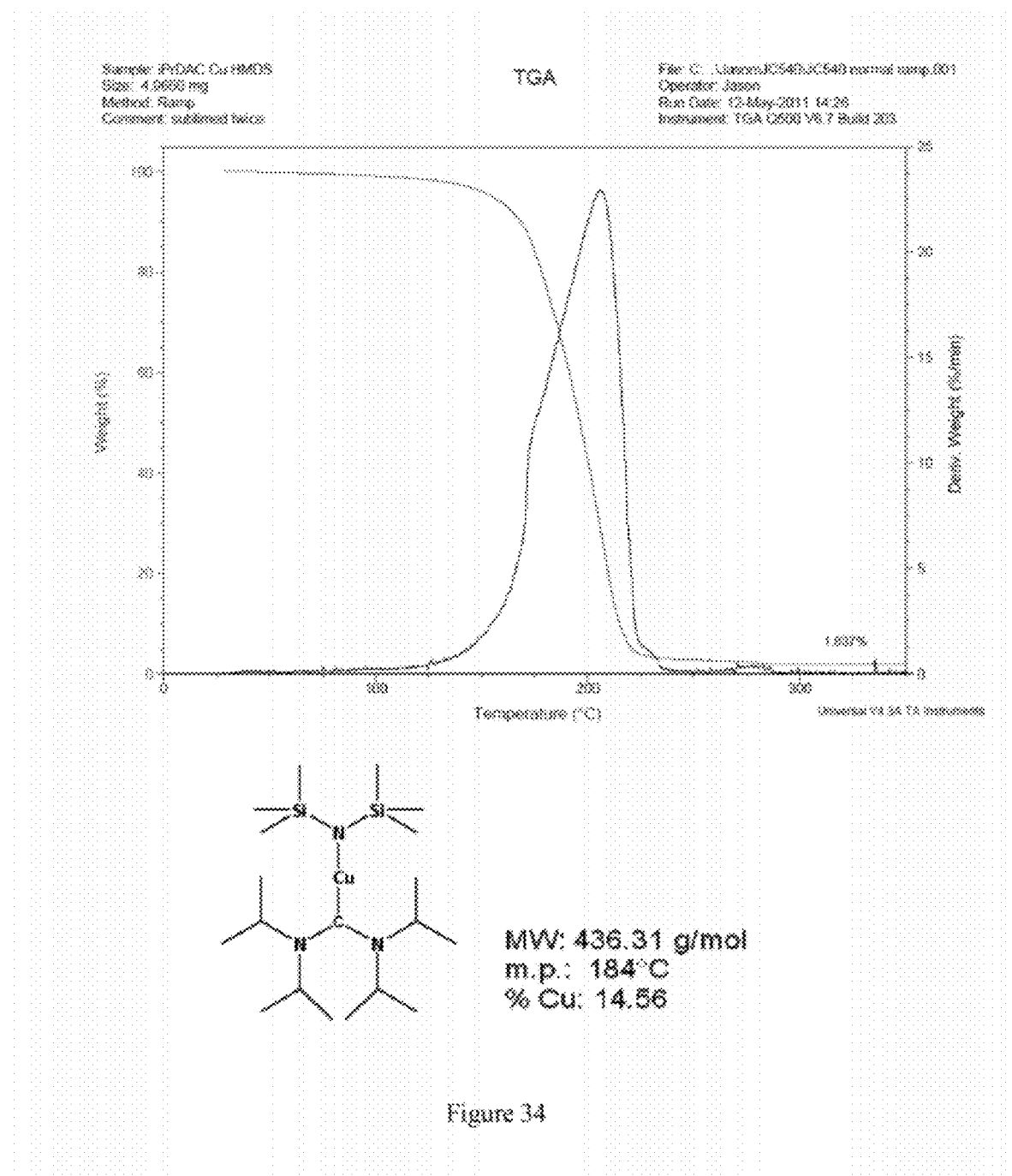
FIG. 34 is a weight loss curve for N,N,N',N'-tetraisopropylformamidinylidene copper hexamethyldisilazide (19a)

The results are provided in FIGS. 33 and 34. The residual mass (% mass that remains in the platinum pan after 600° C.) is displayed in bottom right corner of each graph. These results demonstrated that the acyclic diaminocarbene-containing copper precursors tested had good volatility and thermal stability. The residual masses of less than 5% was indicative of good volatility and negligible decomposition.

Example 12

Synthesis and Characterization of Silver and Gold sNHC Precursors

Materials and Methods

All manipulations were performed in an MBraun Labmaster™ 130 Dry box under a nitrogen atmosphere or in nitrogen filled Schlenk lines. All reaction vessels were wrapped in aluminum foil to exclude light. NMR spectra were recorded on a 400 MHz Bruker AMX. NMR spectra that were measured in CDCl$_3$ were referenced against TMS. NMR spectra measured in C$_6$D$_6$ were referenced against residual protonated solvent. Hydrogen tetrachloroaurate (III) hydrate and silver(I) chloride were purchased from Strem Chemicals (NewburyPort, Mass., USA). Tetrahydrothiophene and hexamethyldisilazane were purchased from Sigma Aldrich Inc. (Oakville, Ontario, Canada). The diethyl ether adduct of lithium hexamethyldisilazide was prepared according to Lappert et al. *JACS* 1983, 105, 302.

Diethyl ether, and toluene were purchased from Calcdon Laboratories Ltd. (Georgetown, Ontario, Canada) as reagent grade and were purified from an MBraun Solvent Purifier System and stored over 3 Å molecular sieves. Anhydrous tetrahydrofuran, anhydrous pentane and anhydrous dichloromethane were purchased from Sigma Aldrich Inc. (Oakville, Ontario, Canada) and used as received.

Tetrahydrothiophene gold(I) chloride

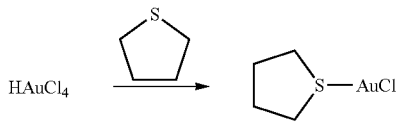

Au(THT)Cl (THT=tetrahydrothiophene) was prepared according to a literature procedure with small modifications (Melgarejo, D. Y.; Chiarella, G. M.; Fackler, J. P. Jr.; Perez, L. M.; Rodrigue-Witchel, A.; Reber, C. *Inorg. Chem.* 2011, 4238-4240).

Hydrogen tetrachloroaurate (III) hydrate (8.22 g, 49% Au, 20.45 mmol of Au) was dissolved in 20 mL of water and 100 mL of ethanol (approx. a 1:5 mixture) in a 400 mL beaker. The colour of the solution was orange. Tetrahydrothiophene (4.2 mL, 47.64 mmol) was added dropwise while the solution was stirred. A deep red colour occurred with each drop of THT, but quickly dissipated. A colourless precipitate gradually formed and the solution cleared to a pale yellow. The suspension was stirred for 1 hour. The white solid was filtered off and washed 3 times with 20 mL of ethanol and then 3 times with 20 mL of diethyl ether. The solid was dried under high vacuum overnight to obtain 6.36 g, 97.1%.

1,3-diisopropyl-imidazolidin-2-ylidene gold(I) chloride and 1,3-diisopropyl-imidazolidin-2-ylidene silver(I) chloride

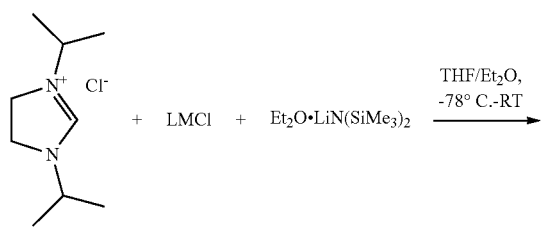

M = Au, L = THT
M = Ag, L = nothing

1,3-Diisopropyl-imidazolidin-2-ylidene gold(I) chloride 1,3-Diisopropyl-4,5-dihydro-3H-imidazol-1-ium chloride (1.654 g, 8.08 mmol) was suspended in 100 mL of THF to which a solution of the diethyl ether adduct of lithium hexamethyldisilazide (1.951 g, 8.08 mmol) in 80 mL of $Et_2O$ was added dropwise. The suspension was stirred for 1 hour during which a clear solution formed. This solution was then cooled in a dry ice/acetone bath to −78° C. and Au(THT)Cl (2.590 g, 8.08 mmol), was added as a solid in 5 portions five minutes apart. Stirring proceeded for 4 h at −78° C. The cooling bath was then removed and the reaction was warmed in an ice water bath. Volatiles were then stripped under high vacuum at 0° C. When the solid residue appeared dry, the reaction vessel was allowed to warm to r.t and drying under vacuum continued for 1 h. The solid was extracted 3 times with 20 mL of $CH_2Cl_2$. The combined $CH_2Cl_2$ extractions were filtered and volatiles were stripped under vacuum.

The solid residue was washed with pentane until the washings were colourless. 3.03 g, 97.0%, of an off white solid was obtained. $^1$H NMR ($CDCl_3$): δ 4.76 (sept, 2H), δ 3.54 (s, 4H), δ 1.23 (d, 12H) $^{13}$C NMR ($CDCl_3$): δ 190.41, δ 81.82, δ 42.23, δ 20.52.

1,3-Diisopropyl-imidazolidin-2-ylidene silver(I) chloride 1,3-Diisopropyl-4,5-dihydro-3H-imidazol-1-ium chloride (0.266 g, 1.39 mmol) was suspended in 10 ml of THF. A solution of the diethyl ether adduct of lithium hexamethyldisilazide (0.333 g, 1.38 mmol) dissolved in 20 ml of toluene was added and the mixture was stirred for 1 h. The solution was cooled in a dry ice/acetone bath to −78° C. and silver(I) chloride (0.180 g, 1.26 mmol) was added. Stirring proceeded for 2.5 h as the solution gradually warmed from −78° C. to 0° C. Volatiles were stripped under reduced pressure to afford a pale yellow solid. The solid was extracted with 15 ml of $CH_2Cl_2$ and then filtered. The filtrate was concentrated to 4 ml and 15 ml of $Et_2O$ was added. The solution was kept at −35° C. for 24 h. Colourless needles were collected by decanting the solution and drying the crystals under vacuum; obtained 0.282 g, 78%. $^1$H NMR ($CDCl_3$): δ 4.32 (sept, 2H), δ 3.55 (s, 4H), δ 1.22 (d, 12H) $^{13}$C($CDCl_3$): δ 52.52, δ 42.69, δ 21.00, carbenic carbon not observed.

Synthesis of 1,3-diisopropyl-imidazolidin-2-ylidene gold(I) hexamethyldisilazide 2c and 1,3-diisopropyl-imidazolidin-2-ylidene silver(I) 2b hexamethyldisilazide

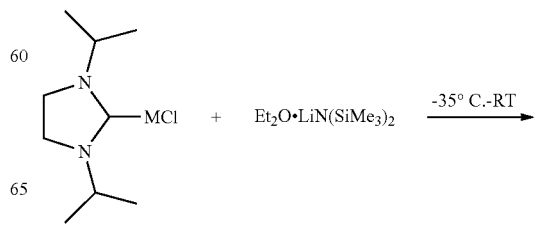

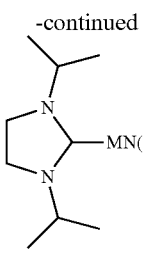

—MN(SiMe₃)₂ + Et₂O + LiCl

M = Au, Ag 1,3-Diisopropyl-imidazolidin-2-ylidene gold(I) hexamethyldisilazide, 2c 1,3-diisopropyl-imidazolidin-2-ylidene gold(I) chloride (3.011 g, 7.79 mmol) was suspended in 150 mL of toluene and cooled to −35° C. in a freezer. The suspension was removed from the freezer and a solution of the diethyl ether adduct of lithium hexamethyldisilazide (1.951 g 8.08 mmol) in 70 mL of toluene was added dropwise. The reaction vessel was allowed to warm to room temperature and stirring was continued for 18 h. The obtained cloudy solution was filtered and volatiles were stripped from the filtrate under high vacuum. The crude solid was sublimed at 90° C. at 40 mtorr employing a −78° C. cold finger. 3.55 g, 89.1%, of a pale yellow solid was obtained. $^1$H NMR($C_6D_6$): δ 4.81 (sept, 2H), δ 2.38 (s, 4H), δ 0.77 (d, 12H), δ 0.62 (s, 18H). $^{13}$C NMR($C_6D_6$): δ 197.68, δ 50.70, δ 41.55, δ 20.04, δ 6.90.

1,3-Diisopropyl-imidazolidin-2-ylidene silver(I) hexamethyldisilazide, 2b 1,3-Diisopropyl-imidazolidin-2-ylidene silver(I) chloride (0.278 g, 0.99 mmol) was stirred in 20 ml of a 1:1 mixture of toluene to THF and cooled to −35° C. in a freezer. The solution was removed from the freezer and a solution of the diethyl ether adduct of lithium hexamethyldisilazide (0.226 g, 0.94 mmol) dissolved in 10 ml of $Et_2O$ was added dropwise. The solution was allowed to warm to room temperature and stirring was continued for 18 h. Volatiles were stripped under reduced pressure and the residue was stirred with 10 ml of pentane and then filtered. The pentane solution was concentrated to 2 ml under vacuum and kept in a −35° C. freezer for several days. Colourless needle crystals (0.261 g, 66%) were collected by decanting the solution and drying the crystals under vacuum. $^1$H NMR($C_6D_6$): δ 4.25 (sept, 2H), δ 2.43 (s, 4H), δ 0.72 (d, 12H), δ 0.61 (s, 18H). $^{13}$C NMR($C_6D_6$): δ 204.80, δ 204.66, δ 202.88, δ 202.75, 651.80, δ 42.00, δ 41.94, δ 20.52, δ 7.42.

Example 13

Thermogravimetric Analysis of Silver and Gold Precursor Compounds

Vapour pressures of a silver and a gold precursor compound were measured on a TA Instruments Q50 thermogravimetric (TG) analyser located in an MBraun Labmaster 130 Dry box under a nitrogen atmosphere. The TG analyzer was run in a stepped isotherm as set out below, using lower temperatures than used in the Examples above in order to minimize the amount of decomposition of the silver and gold precursor compounds.

Ramp program for 1,3-diisopropyl-imidazolidin-2-ylidene gold(I) hexamethyldisilazide 2c:
1: Ramp 40.00° C./min to 80.00° C.
2: Isothermal for 20.00 min
3: Ramp 40.00° C./min to 90.00° C.
4: Isothermal for 15.00 min
5: Ramp 40.00° C./min to 100.00° C.
6: Isothermal for 15.00 min
7: Ramp 40.00° C./min to 110.00° C.
8: Isothermal for 15.00 min
9: Ramp 40.00° C./min to 120.00° C.
10: Isothermal for 15.00 min
11: Ramp 40.00° C./min to 130.00° C.
12: Isothermal for 15.00 min
13: Ramp 40.00° C./min to 140.00° C.
14: Isothermal for 15.00 min
15: Ramp 40.00° C./min to 150.00° C.
16: Isothermal for 15.00 min
17: Ramp 40.00° C./min to 160.00° C.
18: Isothermal for 240.00 min
19: Ramp 40.00° C./min to 600.00° C.

Ramp program for 1,3-diisopropyl-imidazolidin-2-ylidene silver(I) hex amethyldisilazide 2b:
1: Ramp 40.00° C./min to 70.00° C.
2: Isothermal for 40.00 min
3: Ramp 40.00° C./min to 80.00° C.
4: Isothermal for 20.00 min
5: Ramp 40.00° C./min to 90.00° C.
6: Isothermal for 20.00 min
7: Ramp 40.00° C./min to 100.00° C.
8: Isothermal for 20.00 min
9: Ramp 40.00° C./min to 110.00° C.
10: Isothermal for 20.00 min
11: Ramp 40.00° C./min to 120.00° C.
12: Isothermal for 20.00 min
13: Ramp 40.00° C./min to 130.00° C.
14: Isothermal for 20.00 min
15: Ramp 40.00° C./min to 140.00° C.
16: Isothermal for 20.00 min
17: Ramp 40.00° C./min to 150.00° C.
18: Isothermal for 20.00 min
19: Ramp 10.00° C./min to 600.00° C.

As in Example 5, the slope was determined for each isotherm interval, and if the data was linear for that interval, that was used as the "Δm/Δt" value for that temperature. The pressure was calculated using the Langmuir equation following the method of Umarji [G. V. Kunte, S. A. Shivashanker, A. M. Umarji Meas. Sci. Tech. 2008, 19, 025704] for estimation of vapour pressure. Benzoic acid was used as a standard to determine the a coefficient of the Langmuir equation (i.e., the Langmuir adsorption constant), and Cu(tmhd)₂ was used as a benchmark.

Figure 35:
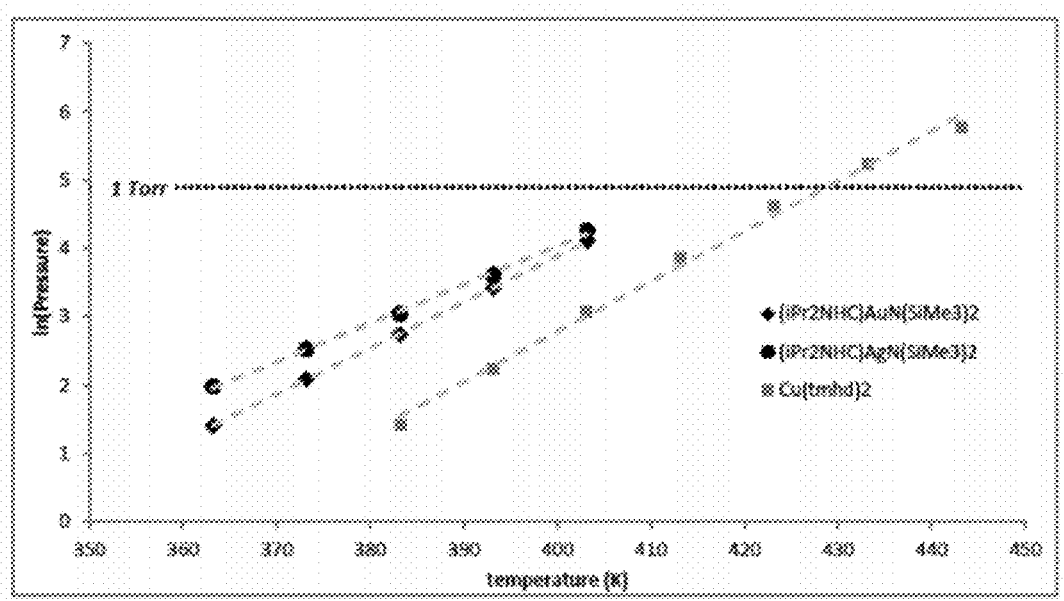
FIG. 35 is a graph of vapour pressure plots for 1,3-diisopropyl-imidazolin-2-ylidene silver hexamethyldisilazide (2b) and 1,3-disopropyl-imidazolin-2-ylidene gold hexamethyldisilazide (2c) precursor compounds in comparison to a control (copper bis-(2,2,6,6-tetramethyl-3,5-heptadionate)

The results from vapour testing of the sNHC-containing silver and gold precursor compounds are depicted in FIG. 35. The compound, Cu(tmhd)₂, was used as a control. The temperature at which both compounds 2b and 2c have a vapour pressure of 1 torr was 142° C.

Example 14

ALD of Gold Using a Gold Precursor Compound 1,3-Diisopropyl-4,5-dihydro-imidazolin-2-ylidene gold (I) hexamethyldisilazide (2c) was used to demonstrate successful gold film deposition to form composite materials from two substrate materials.

In this example, gold films were deposited by ALD using, as the ALD tool, a Picosun SUNALE™ 8200 employing an inductively coupled plasma source. A small amount of precursor (0.3-0.5 g) was loaded into a bubbler and attached to the ALD tool. A mixture of 10% $H_2$ in Ar (balance) was used as the plasma source. A 200 mm silicon substrate with a previously-deposited ruthenium film was introduced to the deposition chamber. The plasma used was a capacitively coupled plasma using screens to prevent ions from reaching the substrate. The conditions used for ALD were as follows:

Plasma: 2500W power, 20 sccm, 90% argon, 10% hydrogen

Temperatures: 100° C. source temperature using a Picosun Picosolid™ booster with 80 sccm of nitrogen; 200° C. reactor temperature Pulse sequence: 2000 cycles of:
 3 seconds of precursor flow
 5 seconds of nitrogen purge
 10 seconds of hydrogen plasma
 4 seconds of nitrogen purge Under the above conditions, gold was successfully deposited by ALD to form a thin gold film on the ruthenium-silicon substrate.

Example 15

Thermal Stress Study of (1,3-diisopropyl-4,5-dihydro-1H-imidazolin-2-ylidene) copper hexamethyldisilazide (2a)

A 0.8 g sample of (1,3-diisopropyl-4,5-dihydro-1H-imidazolin-2-ylidene) copper hexamethyldisilazide (2a) was loaded into a stainless steel vessel, which was inlet capped with a VCR® gasket. The vessel was then heated in an oven at 92° C. and maintained in the oven for two weeks. Every two days, a sample of the compound was removed and tested. In order to obtain a sample for testing, the vessel was removed from the oven and cooled to room temperature in a glovebox. Following removal of the sample, the vessel was returned to the 92° C. oven.

Approximately twenty milligrams of each two-day sample was tested by thermogravimetric analysis. In each case, the approximately 20 mg sample was loaded onto a 1 cm platinum pan and heated at a heating rate of 10° C./min up to 500° C. In addition, 5-10 mg of the initial sample (i.e., prior to heating) and the final sample (i.e., tested on day 15 of heating) were tested using $^1$H NMR.

Figure 36:
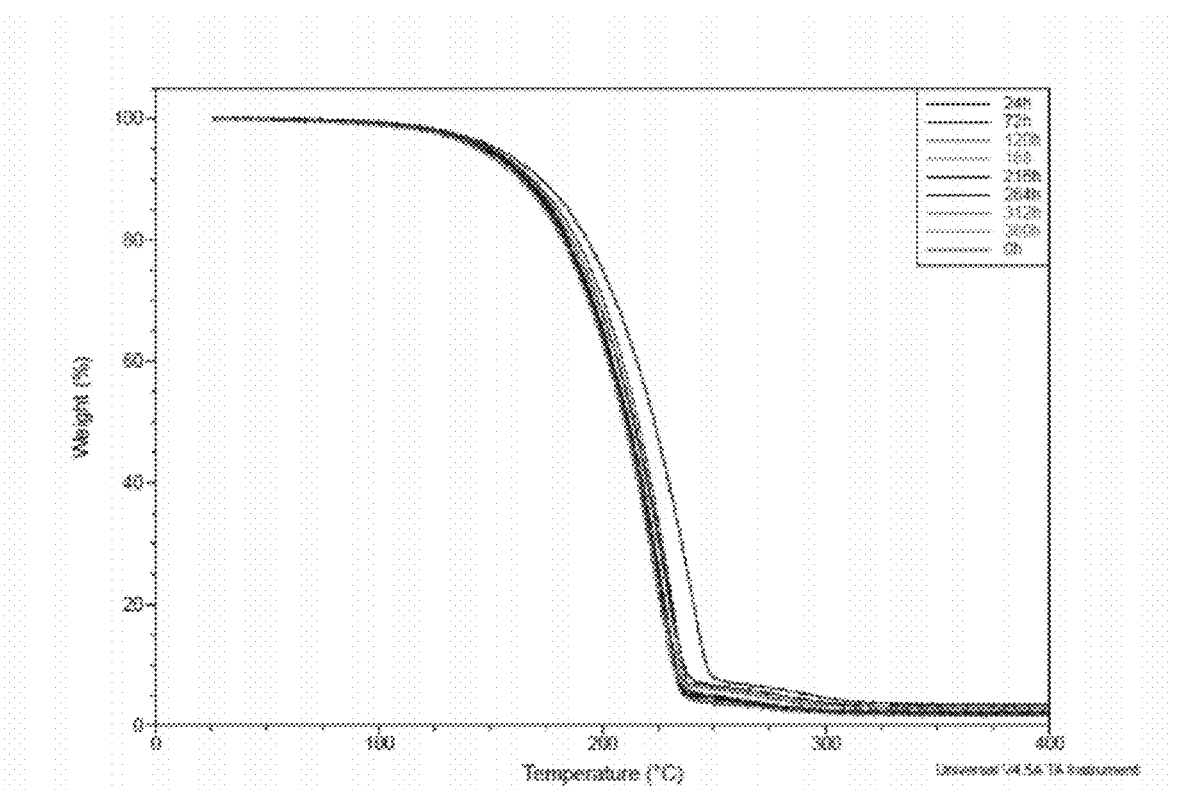
FIG. 36 depicts weight loss curves for (1,3-diisopropyl-4,5-dihydro-1H-imidazolin-2-ylidene) copper hexamethyldisilazide (2a) with heating.

The results of the thermogravimetric analysis are shown in FIG. 36 and summarized in Table 5 below.

TABLE 5

Thermal Stress results

| Time (h) | Sample Mass (mg) | Residual Mass (%) |
|---|---|---|
| 0 | 20.97 | 2.11 |
| 24 | 20.44 | 3.03 |
| 72 | 27.00 | 3.45 |
| 120 | 21.59 | 1.69 |
| 168 | 21.13 | 2.11 |
| 216 | 20.33 | 2.01 |
| 264 | 21.52 | 2.23 |
| 312 | 20.49 | 2.57 |
| 360 | 20.26 | 2.96 |

These results showed that the residual mass varied between 2-3.5%, with no clear increase in residual mass observed from the compound following heating for two weeks.

Figure 37:
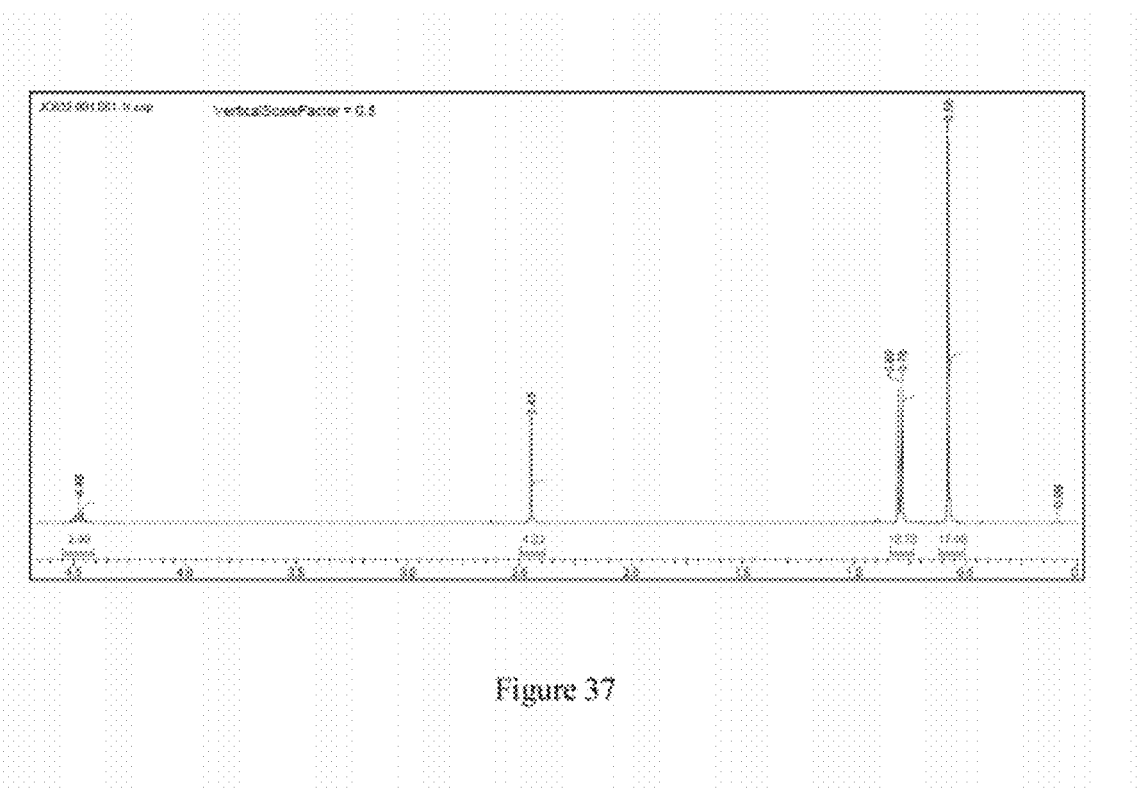
FIG. 37 is a $^1$H NMR spectrum of (1,3-diisopropyl-4,5-dihydro-1H-imidazolin-2-ylidene) copper hexamethyldisilazide (2a) prior to heating.
Figure 38:
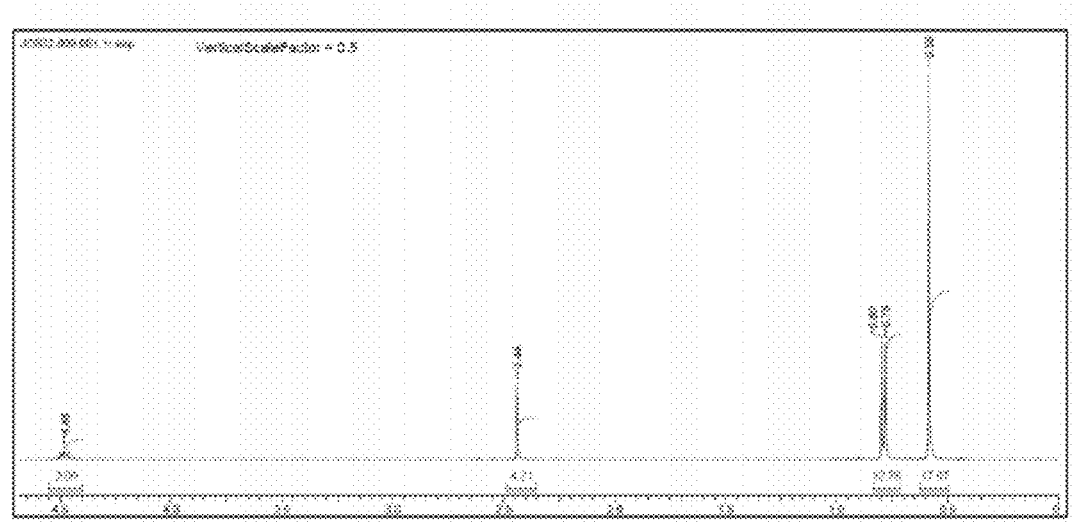
FIG. 38 is a $^1$H NMR spectrum of (1,3-diisopropyl-4,5-dihydro-1H-imidazolin-2-ylidene) copper hexamethyldisilazide (2a) after heating at 92° C. for 15 days.

FIG. 37 shows the $^1$H NMR spectrum of (1,3-diisopropyl-4,5-dihydro-1H-imidazolin-2-ylidene) copper hexamethyldisilazide (2a) prior to heating. FIG. 38 shows the $^1$H NMR spectrum of (1,3-diisopropyl-4,5-dihydro-1H-imidazolin-2-ylidene) copper hexamethyldisilazide (2a) after heating at 92° C. for 360 hours (15 days). The spectrum from the sample following heating for 15 days was identical to the starting spectrum. The minor peaks in the spectra were from impurities present in the initial sample (they are visible in both spectra).

The results of the thermogravimetric analysis and the $^1$H NMR studies demonstrated that there was no detectable decomposition of (1,3-diisopropyl-4,5-dihydro-1H-imidazolin-2-ylidene) copper hexamethyldisilazide (2a) following heating at 92° C. for two weeks.

All publications, patents and patent applications mentioned in this Specification are herein incorporated by reference to the same extent as if each individual publication, patent, or patent application was specifically and individually indicated to be incorporated by reference.

Modifications and improvements to the above-described embodiments of the present invention may become apparent to those skilled in the art. The foregoing description is intended to be exemplary rather than limiting. The scope of the present invention is therefore intended to be limited solely by the scope of the appended claims.

What is claimed is:

1. A compound of Formula I:

DAC-M-X      I wherein
 DAC is a diaminocarbene that is an optionally substituted, saturated N-heterocyclic diaminocarbene (sNHC) or an optionally substituted acyclic diaminocarbene;
 M is a group 11 metal bound to the DAC component at the carbenic atom; and
 X is an anionic ligand,
 wherein the compound does not comprise an aryl or heteroaryl group, and M is bound to a non-halogenic atom of X,
 and wherein the compound will achieve a vapour pressure of at least about 1 torr at 160° C. or less and will remain stable for at least one day at a temperature of at least about 100° C.

2. The compound of claim 1, which is a compound of Formula Ia:

sNHC-M-X      Ia.

3. The compound of claim 2, which is a compound of Formula IIa:

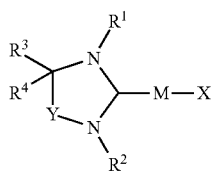

IIa wherein

Y is CR⁵R⁶, (CR⁵R⁶)₂, or NR⁹;

R¹ and R² are each independently H, or an optionally substituted, branched, straight or cyclic aliphatic group, wherein R¹ and R² do not comprise a halo substituent;

R³, R⁴, R⁵ and R⁶ are each independently H, or an optionally substituted, branched, straight or cyclic aliphatic group; and R⁹ is H, or an optionally substituted, branched, straight or cyclic aliphatic group.

4. The compound of claim 1, which is a compound of Formula IIb

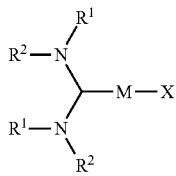

IIb wherein each R¹ R² is independently H, or an optionally substituted, branched, straight or cyclic aliphatic group, wherein R¹ and R² do not comprise a halo substituent.

5. The compound of claim 1, wherein X is not bound to M via an oxygen—metal bond.

6. The compound of claim 1, wherein X is heterocycle, piperidinyl, pyrrolidinyl, alkoxide, alkyl, hydride, hydroxide, diketonate, diketiminate, amidinate or guanidinate or is an amide having the following structure:

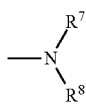

where R⁷ and R⁸ are each independently an optionally substituted branched, straight or cyclic aliphatic group, an optionally substituted branched or straight C₁ to C₁₂ alkylsilyl, or R⁷ and R⁸ together with the amide nitrogen form an optionally substituted heterocycle.

7. The compound of claim 6, wherein R⁷ and R⁸ are each independently H, a C₁ to C₁₂ alkyl or heteroalkyl, or a C₃ to C₁₂ cycloalkyl or cyclic heteroalkyl.

8. The compound of claim 7, wherein X is —N(SiMe₃)₂.

9. The compound of claim 3, wherein R¹, R², R³, R⁴, R⁵ and R⁶ are each independently H, a C₁ to C₁₂ alkyl, or heteroalkyl or a C₃ to C₁₂ cycloalkyl or cyclic heteroalkyl.

10. The compound of claim 3, wherein R¹R², R³, R⁴, R⁵ and R⁶ are each independently H, a C₁ to C₆ alkyl or heteroalkyl, or a C₃ to C₈ cycloalkyl or cyclic heteroalkyl.

11. The compound of claim 10, wherein R¹ and R² are each independently methyl, ethyl, propyl, isopropyl, butyl, 1-methylpropyl, or t-butyl.

12. The compound of claim 1, wherein M is copper, silver, or gold.

13. The compound of claim 1, which is:

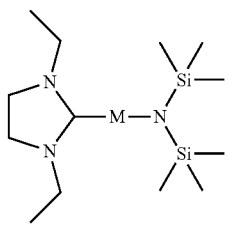 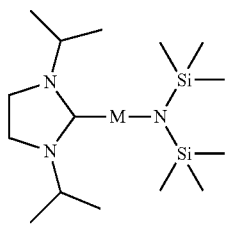

1a, M = Cu
1b, M = Ag
1c, M = Au

2a, M = Cu
2b, M = Ag
2c, M = Au

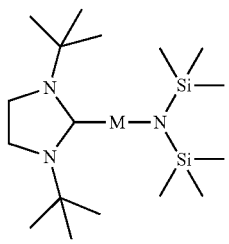 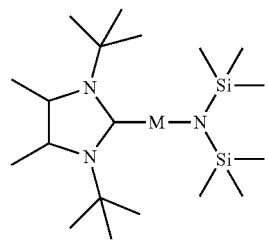

3a, M = Cu
3b, M = Ag
3c, M = Au

4a, M = Cu
4b, M = Ag
4c, M = Au

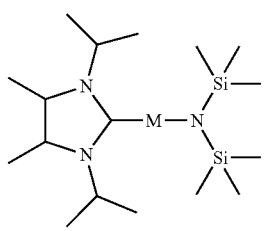

5a, M = Cu
5b, M = Ag
5c, M = Au

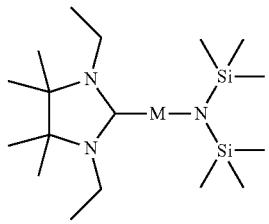

6a, M = Cu
6b, M = Ag
6c, M = Au

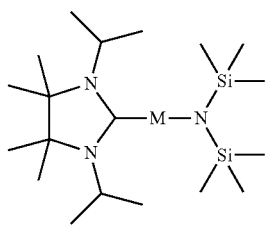

7a, M = Cu
7b, M = Ag
7c, M = Au

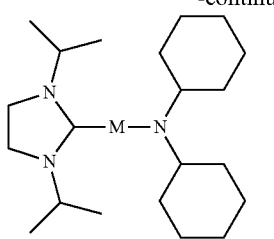

8a, M = Cu
8b, M = Ag
8c, M = Au

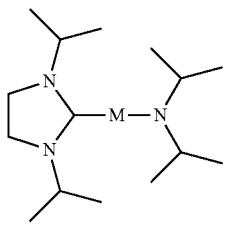

9a, M = Cu
9b, M = Ag
9c, M = Au

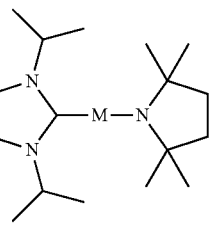

10a, M = Cu
10b, M = Ag
10c, M = Au

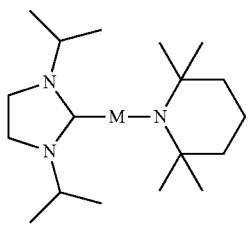

11a, M = Cu
11b, M = Ag
11c, M = Au

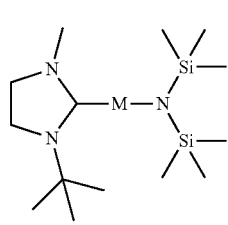

12a, M = Cu
12b, M = Ag
12c, M = Au

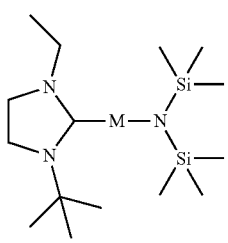

13a, M = Cu
13b, M = Ag
13c, M = Au

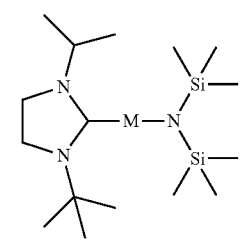

14a, M = Cu
14b, M = Ag
14c, M = Au

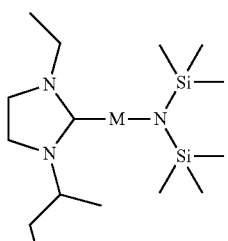

15a, M = Cu
15b, M = Ag
15c, M = Au

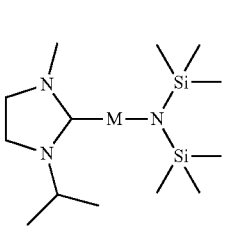

16a, M = Cu
16b, M = Ag
16c, M = Au

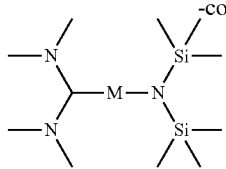

17a, M = Cu
17b, M = Ag
17c, M = Au

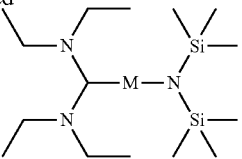

18a, M = Cu
18b, M = Ag
18c, M = Au

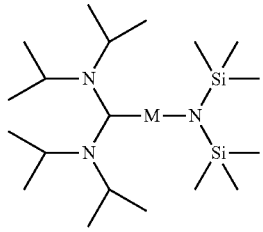

19a, M = Cu
19b, M = Ag
19c, M = Au

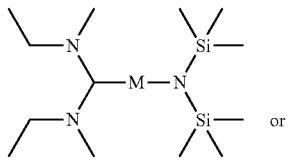

20a, M = Cu
20b, M = Ag
20c, M = Au or

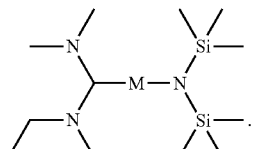

21a, M = Cu
21b, M = Ag
21c, M = Au

14. The compound of claim 3, which is 1,3-diisopropyl-imidazolin-2-ylidene copper hexamethyldisilazide.

15. The compound of claim 1, wherein the compound remains stable at a temperature of at least about 150° C. for an extended period.

16. The compound of claim 1, which is at least 95% pure.

17. The compound of claim 1, which is at least 98% pure.

18. A process for depositing a metal film on a substrate, comprising chemical vapour deposition (CVD), atomic layer deposition (ALD), plasma enhanced chemical vapour deposition (PE-CVD) or plasma enhanced atomic layer deposition (PE-ALD) using a compound of claim 1, wherein M is a group 11 metal, as a precursor compound.

19. A process for forming a thin film comprising a metal, said process comprising the following step:
    (a) exposing a substrate to vapour comprising a precursor compound of Formula I:

$$DAC-M-X \qquad I$$

wherein
  DAC is a diaminocarbene that is an optionally substituted, saturated N-heterocyclic diaminocarbene (sNHC) or an optionally substituted acyclic diaminocarbene;

M is a group 11 metal bound to the sNHC component at the carbenic atom; and

X is an anionic ligand, and wherein the precursor compound does not comprise an aryl or heteroaryl group, and M is bound to a non-halogenic atom of X.

20. The process of claim 19, wherein in the step of exposing a substrate to vapour comprising a precursor compound, the substrate is exposed to a vapour comprising the precursor compound and a reactive gas to form a metal film on the surface of the substrate.

21. The process of claim 19 additionally comprising:
volatilizing the precursor compound to form a precursor vapour prior to exposing the substrate to the precursor vapour.

22. The process of claim 19, wherein the precursor compound is:

a compound of Formula Ia:

sNHC-M-X      Ia;

or a compound of Formula IIa:

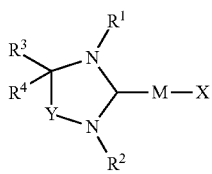

IIa wherein

Y is CR5R6, (CR5R6)2, or NR9;

R$^1$ and R$^2$ are each independently H, or an optionally substituted, branched, straight or cyclic aliphatic group, wherein R$^1$ and R$^2$ do not comprise a halo substituent;

R$^3$, R$^4$, R$^5$ and R$^6$ are each independently H, or an optionally substituted, branched, straight or cyclic aliphatic group; and R$^9$ is H, or an optionally substituted, branched, straight or cyclic aliphatic group; or a compound of Formula IIb:

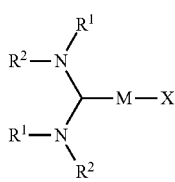

IIb wherein each R$^1$ and R$^2$ is independently H, or an optionally substituted, branched, straight or cyclic aliphatic group, wherein R$^1$ and R$^2$ do not comprise a halo substituent.

23. The process of claim 19, wherein the temperature of vaporization of the compound is above 50° C.

24. The process of claim 19, further comprising heating the substrate.

25. The process of claim 19, wherein the substrate comprises: glass; TaN; TiN; sapphire; indium tin oxide (ITO); SiO$_2$; silicon; silicon nitride; silicon oxy nitride; silicon oxycarbide; fused silica; polymeric material; tungsten; tantalum; ruthenium; organic materials; another metal or alloy used as a barrier layer in semiconductor manufacturing; or any combination thereof.

26. The process of claim 19, wherein M is Cu, Ag, or Au.

27. A system for use in metal deposition to form a thin film on a substrate, comprising a precursor compound according to claim 1.

28. The system of claim 27, wherein said precursor compound is in an air-tight container.

29. The system of claim 28, wherein said air-tight container is a bubbler configured for use with an ALD tool, a flame sealed ampule, or a vial or tube having a cap that is removably attached to said vial or tube to produce an air-tight seal.

30. The system claim 27, wherein the precursor compound is packaged under an inert atmosphere.

31. The system of claim 27, additionally comprising a desiccant, an anti-oxidant or an additive for inhibiting spontaneous decomposition of said precursor compound.

32. The system of claim 27, additionally comprising means for volatilizing said precursor compound.

33. The system of claim 32, wherein said means for volatilizing said precursor compound is comprised within an atomic layer deposition (ALD) or chemical vapour deposition (CVD) tool.

34. An atomic layer deposition (ALD) precursor formulation comprising a mono-metallic precursor compound of claim 1.

35. The ALD precursor formulation of claim 34, packaged in an air-tight container under an inert atmosphere.

36. A method of synthesizing a metal precursor compound of Formula Ia

DAC-M-X      Ia wherein

DAC is a diaminocarbene that is an optionally substituted, saturated N-heterocyclic diaminocarbene (sNHC) or an optionally substituted acyclic diaminocarbene;

M is a group 11 metal bound to the sNHC component at the carbenic atom; and

X is an anionic ligand, and wherein DAC and X do not comprise an aryl or heteroaryl group, said method comprising:

reacting an DAC metal halide with a salt of the anionic ligand such that a bond is formed between M and a non-halogenic atom of X.

37. The method of claim 36, comprising reacting a metal halide of Formula IV:

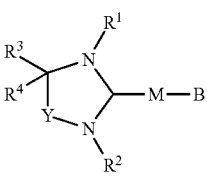

IVa wherein B is a halide;

Y is CR$^5$R$^6$, (CR$^5$R$^6$)$_2$, or NR$^5$;

R$^1$ and R$^2$ are each independently H, or an optionally substituted branched, straight or cyclic aliphatic group, wherein R$^1$ and R$^2$ do not comprise any halide atoms; and $R^3$, $R^4$, $R^5$ and $R^6$ are each independently H, or an optionally substituted, branched, straight or cyclic aliphatic group;

with a salt of the anionic ligand X to produce a compound of Formula IIa:

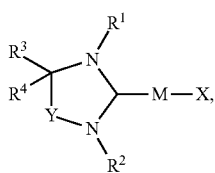

IIa wherein the precursor compound does not comprise an aryl or heteroaryl group, and M is bound to a non-halogenic atom of X.

38. The method of claim 36, comprising reacting a metal halide of Formula IVb:

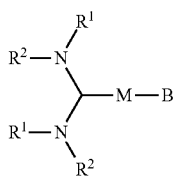

IVb wherein B is a halide;

Y is $CR^5R^6$, $(CR^5R^6)_2$, or $NR^5$;

$R^1$ and $R^2$ are each independently H, or an optionally substituted branched, straight or cyclic aliphatic group, wherein $R^1$ and $R^2$ do not comprise any halide atoms; and $R^3$, $R^4$, $R^5$ and $R^6$ are each independently H, or an optionally substituted, branched, straight or cyclic aliphatic group;

with a salt of the anionic ligand X to produce a compound of Formula IIb:

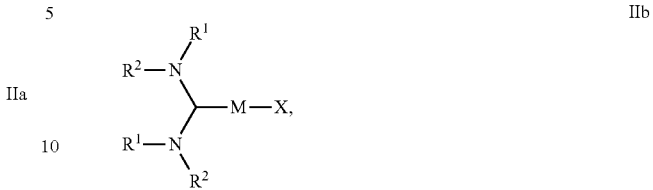

wherein the precursor compound does not comprise an aryl or heteroaryl group, and M is bound to a non-halogenic atom of X.

39. The method of claim 36, wherein the salt of the anionic ligand X is a lithium, sodium, or potassium salt.

40. The process of claim 19, wherein the process is carried out under conditions that permit adsorption of the precursor compound to form a monolayer on the substrate and the process additionally comprises:

(b) purging excess precursor compound;

(c) exposing the adsorbed precursor monolayer formed in step (a) to a reactant precursor compound to reduce the precursor monolayer to form a metal layer; and (d) repeating steps (a)-(c) until the thin film reaches a desired thickness.

41. The process of claim 40, wherein the reactant precursor is:

plasma;

an oxidizing gas, such as oxygen, ozone, water, hydrogen peroxide, nitric oxide, nitrogen dioxide, a radical species thereof, or a mixture of any two or more of the oxidizing gases; or a reducing agent such as one of hydrogen, a forming gas (i.e., ~5% hydrogen, ~95% nitrogen mixture), ammonia, a silane, a borane, an amino borane, an alane, formic acid, a hydrazine (e.g., dimethylhydrazine), a radical species thereof, or a mixture of any two or more of the reducing agents.

* * * * *